US006670357B2

(12) United States Patent
Leftheris et al.

(10) Patent No.: US 6,670,357 B2
(45) Date of Patent: Dec. 30, 2003

(54) METHODS OF TREATING P38 KINASE-ASSOCIATED CONDITIONS AND PYRROLOTRIAZINE COMPOUNDS USEFUL AS KINASE INHIBITORS

(75) Inventors: Katerina Leftheris, Skillman, NJ (US); John Hynes, Washington Crossing, PA (US); Stephen T. Wrobleski, Whitehouse Station, NJ (US); Joel Barrish, Richboro, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 27 days.

(21) Appl. No.: 10/036,293

(22) Filed: Nov. 7, 2001

(65) Prior Publication Data

US 2003/0069244 A1 Apr. 10, 2003

Related U.S. Application Data

(60) Provisional application No. 60/249,877, filed on Nov. 17, 2000, and provisional application No. 60/310,561, filed on Aug. 7, 2001.

(51) Int. Cl.[7] .................. C07D 487/04; A61K 31/53; A61P 11/06; A61P 19/02; A61P 19/10
(52) U.S. Cl. .................. 514/218; 544/183; 544/112; 540/553; 540/575; 514/243; 514/233.2
(58) Field of Search ................... 544/183, 112; 514/243, 233.2, 218; 540/553, 575

(56) References Cited

U.S. PATENT DOCUMENTS

| | | | |
|---|---|---|---|
| 5,658,903 A | 8/1997 | Adams et al. | 514/235.8 |
| 5,932,576 A | 8/1999 | Anantanarayan et al. | 514/235.5 |
| 5,945,418 A | 8/1999 | Bemis et al. | 514/258 |
| 5,977,103 A | 11/1999 | Adams et al. | 514/235.2 |
| 6,087,496 A | 7/2000 | Anantanarayan et al. | 514/124 |
| 6,130,235 A | 10/2000 | Mavunkel et al. | 514/322 |
| 6,147,080 A | 11/2000 | Bemis et al. | 514/248 |
| 6,251,914 B1 | 6/2001 | Adams et al. | 514/274 |
| 6,277,989 B1 | 8/2001 | Chakravarty et al. | 544/393 |

FOREIGN PATENT DOCUMENTS

| | | |
|---|---|---|
| EP | 0713876 | 5/1996 |
| EP | 0778277 A1 * | 11/1997 |
| WO | WO9924033 | 5/1999 |
| WO | WO 00/12074 | 3/2000 |
| WO | WO 00/12497 | 3/2000 |
| WO | WO 00/56738 | 9/2000 |
| WO | WO 00/71129 A1 * | 11/2000 |
| WO | WO 01/14378 A1 * | 3/2001 |
| WO | WO 01/27089 A1 | 4/2001 |
| WO | WO 01/34605 A1 | 5/2001 |
| WO | WO01/47897 | 7/2001 |

OTHER PUBLICATIONS

Moreland et al.; American College of Physicians—Am. Soc. of Internal Medicine; vol. 130; pp. 478–486 (1999).
Henry et al.; Drugs of the Future 24(12) pp. 1345–1354 (1999).
Rankin et al.; British Journal of Rhematology, 34, pp. 334–342 (1995).
Salituro et al., Current Medicinal Chemistry; 6 pp. 807–823 (1999).*

* cited by examiner

Primary Examiner—Mark L. Berch
Assistant Examiner—Kahsay Habte
(74) Attorney, Agent, or Firm—Anastasia P. Winslow

(57) ABSTRACT

Methods of treating one or more conditions associated with p38 kinase activity are disclosed comprising administering to a patient in need thereof at least one compound having the formula (I):

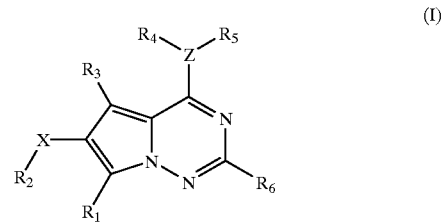

or a pharmaceutically acceptable salt, prodrug, or solvate thereof, wherein $R_3$ is hydrogen, methyl, perfluoromethyl, methoxy, halogen, cyano, or $NH_2$, preferably methyl, and X, $R_1$ through $R_6$, and Z are as described in the specification. Advantageously the groups —$ZR_4R_5$ taken together comprise an —NH-substituted aryl.

24 Claims, No Drawings

METHODS OF TREATING P38 KINASE-ASSOCIATED CONDITIONS AND PYRROLOTRIAZINE COMPOUNDS USEFUL AS KINASE INHIBITORS

RELATED INVENTIONS

This application claims the benefit of U.S. Provisional Application No. 60/249,877, filed Nov. 17, 2000, and U.S. Provisional Application No. 60/310,561, filed Aug. 7, 2001, both of which are incorporated herein by reference.

FIELD OF THE INVENTION

This invention relates to methods of treating conditions associated with p38α and β kinases and to pyrrolotriazine compounds, more particularly, to pyrrolotriazine carboxamide and benzamide compounds useful for treating p38 kinase-associated conditions.

BACKGROUND OF THE INVENTION

A large number of cytokines participate in the inflammatory response, including IL-1, IL-6, IL-8 and TNF-α. Overproduction of cytokines such as IL-1 and TNF α are implicated in a wide variety of diseases, including inflammatory bowel disease, rheumatoid arthritis, psoriasis, multiple sclerosis, endotoxin shock, osteoporosis, Alzheimer's disease, and congestive heart failure, among others [Henry et al., *Drugs Fut.*, 24:1345–1354 (1999); Salituro et al., *Curr. Med. Chem.*, 6:807–823 (1999)]. Evidence in human patients indicates that protein antagonists of cytokines are effective in treating chronic inflammatory diseases, such as, for example, monoclonal antibody to TNF-α (Enbrel) [Rankin et al., *Br. J. Rheumatol.*, 34:334–342 (1995)], and soluble TNF-α receptor-Fc fusion protein (Etanercept) [Moreland et al., *Ann. Intern. Med.*, 130:478–486 (1999)].

The biosynthesis of TNF-α occurs in many cell types in response to an external stimulus, such as, for example, a mitogen, an infectious organism, or trauma. Important mediators of TNF-α production are the mitogen-activated protein (MAP) kinases, and in particular, p38 kinase. These kinases are activated in response to various stress stimuli, including but not limited to proinflammatory cytokines, endotoxin, ultraviolet light, and osmotic shock. Activation of p38 requires dual phosphorylation by upstream MAP kinase kinases (MKK3 and MKK6) on threonine and tyrosine within a Thr-Gly-Tyr motif characteristic of p38 isozymes.

There are four known isoforms of p38, i.e., p38α, p38β, p38γ, and p38δ. The α and β isoforms are expressed in inflammatory cells and are key mediators of TNF-α production. Inhibiting the p38α and β enzymes in cells results in reduced levels of TNF-α expression. Also, administering p38α and β inhibitors in animal models of inflammatory disease has proven that such inhibitors are effective in treating those diseases. Accordingly, the p38 enzymes serve an important role in inflammatory processes mediated by IL-1 and TNF-α. Compounds that reportedly inhibit p38 kinase and cytokines such as IL-1 and TNF-α for use in treating inflammatory diseases are disclosed in U.S. Pat. Nos. 6,277,989 and 6,130,235 to Scios, inc; U.S. Pat. Nos. 6,147,080 and 5,945,418 to Vertex Pharmaceuticals Inc; U.S. Pat. Nos. 6,251,914, 5,977,103 and 5,658,903 to Smith-Kline Beecham Corp.; U.S. Pat. Nos. 5,932,576 and 6,087,496 to G.D. Searle & Co.; WO 00/56738 and WO 01/27089 to Astra Zeneca; WO 01/34605 to Johnson & Johnson; WO 00/12497 (quinazoline derivatives as p38 kinase inhibitors); WO 00/56738 (pyridine and pyrimidine derivatives for the same purpose); WO 00/12497 (discusses the relationship between p38 kinase inhibitors); and WO 00/12074 (piperazine and piperidine compounds useful as p38 inhibitors).

The present invention provides methods of treating conditions associated with p38 kinase activity comprising administering to a patient in need thereof certain pyrrolotriazine compounds. The invention further provides select pyrrolotriazine compounds, including 5-methyl and 5-trifluoromethyl pyrrolotriazine-6-carboxamide compounds useful as kinase inhibitors, particularly kinases p38α and β. Pyrrolotriazine compounds useful as tyrosine kinase inhibitors are disclosed in U.S. patent application Ser. No. 09/573,829 filed May 18, 2000, assigned to the present assignee. Pyrrolotriazine compounds substituted with an acidic group reportedly having sPLA$_2$-inhibitory activity are disclosed in WO 01/14378 A1 to Shionogi & Co., Ltd, published Mar. 1, 2001 in Japanese. Each of the patent applications, patents, and publications referred to herein is incorporated herein by reference.

SUMMARY OF THE INVENTION

The instant invention is directed to methods of treating one or more conditions associated with p38 kinase activity comprising administering to a patient in need thereof one or more pharmaceutically-active compounds having the Formula (I):

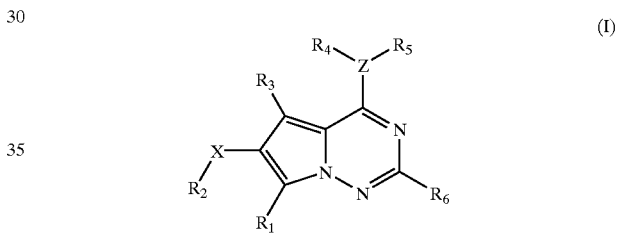

or a pharmaceutically acceptable salt, prodrug, or solvate thereof, wherein:

R$_3$ is hydrogen, methyl, perfluoromethyl, methoxy, halogen, cyano, or NH$_2$;

X is selected from —O—, —OC(=O)—, —S—, —S(=O)—, —SO$_2$—, —C(=O)—, —CO$_2$—, —NR$_{10}$—, —NR$_{10}$C(=O)—, —NR$_{10}$C(=O)NR$_{11}$—, —NR$_{10}$CO$_2$—, —NR$_{10}$SO$_2$—, —NR$_{10}$SO$_2$NR$_{11}$—, —SO$_2$NR$_{10}$—, —C(=O)NR$_{10}$—, halogen, nitro, and cyano, or X is absent;

Z is selected from O, S, N, and CR$_{20}$, wherein when Z is CR$_{20}$, said carbon atom may form an optionally-substituted bicyclic aryl or heteroaryl with R$_4$ and R$_5$;

R$_1$ is hydrogen, —CH$_3$, —OH, —OCH$_3$, —SH, —SCH$_3$, —OC(=O)R$_{21}$, —S(=O)R$_{22}$, —SO$_2$R$_{22}$, —SO$_2$NR$_{24}$R$_{25}$, —CO$_2$R$_{21}$, —C(=O)NR$_{24}$R$_{25}$, —NH$_2$, —NR$_{24}$R$_{25}$, —NR$_{21}$SO$_2$NR$_{24}$R$_{25}$, —NR$_{21}$SO$_2$R$_{22}$, —NR$_{24}$C(=O)R$_{25}$, —NR$_{24}$CO$_2$R$_{25}$, —NR$_{21}$C(=O)NR$_{24}$R$_{25}$, halogen, nitro, or cyano;

R$_2$ is selected from:
 a) hydrogen, provided that R$_2$ is not hydrogen if X is —S(=O)—, —SO$_2$—, —NR$_{10}$CO$_2$—, or —NR$_{10}$SO$_2$—;
 b) alkyl, alkenyl, and alkynyl optionally substituted with up to four R$_{26}$;
 c) aryl and heteroaryl optionally substituted with up to three R$_{27}$; and d) heterocyclo and cycloalkyl optionally substituted with keto (═O), up to three R$_{27}$, and/or having a carbon—carbon bridge of 3 to 4 carbon atoms; or e) R$_2$ is absent if X is halogen, nitro, or cyano;

(i) R$_4$ is substituted aryl, aryl substituted with NHSO$_2$alkyl, substituted heteroaryl, or an optionally-substituted bicyclic 7–11 membered saturated or unsaturated carbocyclic or heterocyclic ring, and R$_5$ is hydrogen, alkyl, or substituted alkyl, except when Z is O or S, R$_5$ is absent, or alternatively, (ii) R$_4$ and R$_5$ taken together with Z form an optionally-substituted bicyclic 7–11 membered aryl or heteroaryl;

R$_6$ is hydrogen, alkyl, substituted alkyl, aryl, substituted aryl, heterocyclo, substituted heterocyclo, —NR$_7$R$_8$, —OR$_7$, or halogen;

R$_{10}$ and R$_{11}$ are independently selected from hydrogen, alkyl, substituted alkyl, aryl, substituted aryl, cycloalkyl, substituted cycloalkyl, heterocyclo, and substituted heterocyclo;

R$_7$, R$_8$, R$_{21}$, R$_{24}$, and R$_{25}$ are independently selected from hydrogen, alkyl, substituted alkyl, aryl, substituted aryl, heterocylco, and substituted heterocyclo;

R$_{20}$ is hydrogen, lower alkyl, or substituted alkyl, or R$_{20}$ may be absent if the carbon atom to which it is attached together with R$_4$ and R$_5$ is part of an unsaturated bicyclic aryl or heteroaryl;

R$_{22}$ is alkyl, substituted alkyl, aryl, substituted aryl, heterocyclo, or substituted heterocyclo;

R$_{26}$ is selected from halogen, trifluoromethyl, haloalkoxy, keto (═O), nitro, cyano, —SR$_{28}$, —OR$_{28}$, —NR$_{28}$R$_{29}$, —NR$_{28}$SO$_2$, —NR$_{28}$SO$_2$R$_{29}$, —SO$_2$R$_{28}$, —SO$_2$NR$_{28}$R$_{29}$, —CO$_2$R$_{28}$, —C(═O)R$_{28}$, —C(═O) NR$_{28}$R$_{29}$, —OC(═O)R$_{28}$, —OC(═O)NR$_{28}$R$_{29}$, —NR$_{28}$C(═O)R$_{29}$, —NR$_{28}$CO$_2$R$_{29}$, ═N—OH, ═N—O-alkyl; aryl optionally substituted with one to three R$_{27}$; cycloalkyl optionally substituted with keto (═O), one to three R$_{27}$, or having a carbon—carbon bridge of 3 to 4 carbon atoms; and heterocyclo optionally substituted with keto (═O), one to three R$_{27}$, or having a carbon—carbon bridge of 3 to 4 carbon atoms; wherein R$_{28}$ and R$_{29}$ are each independently selected from hydrogen, alkyl, alkenyl, aryl, aralkyl, C$_{3-7}$ cycloalkyl, and C$_{3-7}$ heterocycle, or may be taken together to form a C$_{3-7}$ heterocycle; and wherein each R$_{28}$ and R$_{29}$ in turn is optionally substituted with up to two of alkyl, alkenyl, halogen, haloalkyl, haloalkoxy, cyano, nitro, amino, hydroxy, alkoxy, alkylthio, phenyl, benzyl, phenyloxy, and benzyloxy; and R$_{27}$ is selected from alkyl, R$_{32}$, and C$_{1-4}$ alkyl substituted with one to three R$_{32}$, wherein each R$_{32}$ group is independently selected from halogen, haloalkyl, haloalkoxy, nitro, cyano, —SR$_{30}$, —OR$_{30}$, —NR$_{30}$R$_{31}$, —NR$_{30}$SO$_2$, —NR$_{30}$SO$_2$R$_{31}$, —SO$_2$R$_{30}$, —SO$_2$NR$_{30}$R$_{31}$, —CO$_2$R$_{30}$, —C(═O)R$_{30}$, —C(═O) NR$_{30}$R$_{31}$, —OC(═O)R$_{30}$, —OC(═O)NR$_{30}$R$_{31}$, —NR$_{30}$C(═O)R$_{31}$, —NR$_{30}$CO$_2$R$_{31}$, and a 3 to 7 membered carbocyclic or heterocyclic ring optionally substituted with alkyl, halogen, hydroxy, alkoxy, haloalkyl, haloalkoxy, nitro, amino, or cyano, wherein R$_{30}$ and R$_{31}$ are each independently selected from hydrogen, alkyl, alkenyl, aryl, aralkyl, C$_{3-7}$cycloalkyl, and heterocycle, or may be taken together to form a C$_{3-7}$heterocycle.

The invention is further directed to compounds having surprisingly advantageous activity as inhibitors of p38 kinases α and β and TNF-α comprising compounds of Formula (II):

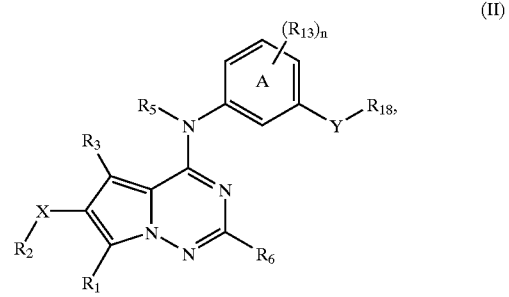

and pharmaceutically acceptable salts, prodrugs or solvates thereof, wherein:

R$_3$ is methyl or CF$_3$;

R$_5$ is hydrogen or alkyl;

Y is —C(═O)NR$_{23}$—, —NR$_{23}$C(═O)NR$_{23}$—, —NR$_{23}$SO$_2$—, or —SO$_2$NR$_{23}$—;

R$_{18}$ and R$_{23}$ are selected from hydrogen, alkyl, alkoxy, aryl, and aryl substituted with one to three R$_{19}$, except when Y is —NR$_{23}$SO$_2$—, R$_{18}$ is C$_{1-4}$alkyl or aryl optionally substituted with one to three R$_{19}$;

R$_{13}$ and R$_{19}$ at each occurrence are independently selected from alkyl, halo, trifluoromethoxy, trifluoromethyl, hydroxy, alkoxy, alkanoyl, alkanoyloxy, thiol, alkylthio, ureido, nitro, cyano, carboxy, carboxyalkyl, carbamyl, alkoxycarbonyl, alkylthiono, arylthiono, arylsulfonylamine, alkylsulfonylamine, sulfonic acid, alkysulfonyl, sulfonamido, and aryloxy, wherein each R$_{13}$ and/or R$_{19}$ group may be further substituted by hydroxy, alkyl, alkoxy, aryl, or aralkyl; and X, R$_1$, R$_2$, and R$_6$ are as defined above for compounds of Formula (I).

DESCRIPTION OF THE INVENTION

Listed below are definitions of various terms used to describe this invention. These definitions apply to the terms as they are used throughout this specification, unless otherwise limited in specific instances, either individually or as part of a larger group.

The term "alkyl" refers to straight or branched chain unsubstituted hydrocarbon groups of 1 to 20 carbon atoms, preferably 1 to 7 carbon atoms. The expression "lower alkyl" refers to unsubstituted alkyl groups of 1 to 4 carbon atoms. When a subscript is used with reference to an alkyl or other group, the subscript refers to the number of carbon atoms that the group may contain. The term "C$_{0-4}$alkyl" includes a bond and alkyl groups of 1 to 4 carbon atoms.

The term "substituted alkyl" refers to an alkyl group substituted by one to four substituents selected from halo, hydroxy, alkoxy, oxo (═O), alkanoyl, aryloxy, alkanoyloxy, amino, alkylamino, arylamino, aralkylamino, disubstituted amines in which the 2 amino substituents are selected from alkyl, aryl or aralkyl; alkanoylamino, aroylamino, aralkanoylamino, substituted alkanoylamino, substituted arylamino, substituted aralkanoylamino, thiol, alkylthio, arylthio, aralkylthio, alkylthiono, arylthiono, aralkylthiono, alkylsulfonyl, arylsulfonyl, aralkylsulfonyl, sulfonamido, e.g. SO$_2$NH$_2$, substituted sulfonamido, nitro, cyano, carboxy, carbamyl, e.g. CONH$_2$, substituted carbamyl e.g.

CONHalkyl, CONHaryl, CONHaralkyl or cases where there are two substituents on the nitrogen selected from alkyl, aryl or aralkyl; alkoxycarbonyl, aryl, substituted aryl, guanidino and substituted or unsubstituted heterocyclos, such as indolyl, imidazolyl, furyl, thienyl, thiazolyl, pyrrolidyl, pyridyl, pyrimidyl and the like. Where the substituent on the alkyl is further substituted, it will be with alkyl, alkoxy, aryl, or aralkyl.

When the term alkyl is used in connection with another group, as in heterocycloalkyl or cycloalkylalkyl, this means the identified group is bonded directly through an alkyl group which may be branched or straight chain. In the case of substituents, as in "substituted cycloalkylalkyl," the alkyl portion of the group may, besides being branched or straight chain, be substituted as recited above for substituted alkyl groups and/or the connected group may be substituted as recited herein for that group.

The term "halogen" or "halo" refers to fluorine, chlorine, bromine and iodine.

The term "aryl" refers to monocyclic or bicyclic aromatic hydrocarbon groups having 6 to 12 carbon atoms in the ring portion, such as phenyl, naphthyl, biphenyl and diphenyl groups. When the aryl is substituted, each ring of the aryl may be substituted.

The term "substituted aryl" refers to an aryl group substituted by one to four substituents selected from alkyl, substituted alkyl, halo, trifluoromethoxy, trifluoromethyl, hydroxy, alkoxy, alkanoyl, alkanoyloxy, amino, alkylamino, aralkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfonic acid, alkysulfonyl, sulfonamido, and aryloxy. The substituent may be further substituted by hydroxy, alkyl, alkoxy, aryl, substituted aryl, substituted alkyl or aralkyl.

The term "aralkyl" refers to an aryl group bonded directly through an alkyl group, such as benzyl, wherein the alkyl group may be branched or straight chain. In the case of a "substituted aralkyl," the alkyl portion of the group may, besides being branched or straight chain, be substituted as recited above for substituted alkyl groups and/or the aryl portion may be substituted as recited for substituted aryl. Thus, the term "optionally substituted benzyl" refers to the group

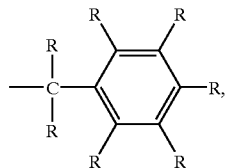

wherein each R group may be hydrogen or may also be selected from alkyl, halogen, cyano, nitro, amino, hydroxy, alkoxy, alkylthio, phenyl, benzyl, phenyloxy, and benzyloxy, and other groups recited above. At least two of these "R" groups should be hydrogen and preferably at least five of the "R" groups is hydrogen. A preferred benzyl group involves the alkyl-portion being branched to define

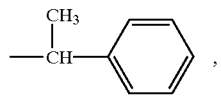

The term "heteroaryl" refers to an aromatic group for example, which is a 4 to 7 membered monocyclic, 7 to 11 membered bicyclic, or 10 to 15 membered tricyclic ring system, which has at least one heteroatom and at least one carbon atom-containing ring. Each ring of the heteroaryl group containing a heteroatom can contain one or two oxygen or sulfur atoms and/or from one to four nitrogen atoms, provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring.

A "substituted heteroaryl" has one to four substituents on any one or more of the rings comprising the heteraryl group. The substituents may be selected from those recited below for heterocycle groups.

Exemplary monocyclic heteroaryl groups include pyrrolyl, pyrazolyl, pyrazolinyl, imidazolyl, oxazolyl, isoxazolyl, thiazolyl (i.e., 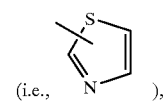 ), thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxaxolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "substituted alkenyl" refers to an alkenyl group substituted by one to two substituents selected from halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino, and substituted and unsubstituted heterocycles, including indolyl, imidazolyl, furyl, thienyl, thiazolyl, pyrrolidyl, pyridyl, pyrimidyl and the like.

The term "alkynyl" refers to straight or branched chain hydrocarbon groups of 2 to 20 carbon atoms, preferably 2 to 15 carbon atoms, and most preferably 2 to 8 carbon atoms, having one to four triple bonds.

The term "substituted alkynyl" refers to an alkynyl group substituted by a substituent selected from halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and substituted or unsubstituted heterocyclo, e.g. imidazolyl, furyl, thienyl, thiazolyl, pyrrolidyl, pyridyl, pyrimidyl and the like.

The term "cycloalkyl" refers to a saturated or partially unsaturated non-aromatic cyclic hydrocarbon ring system, preferably containing 1 to 3 rings and 3 to 7 carbons per ring which may be further fused with an unsaturated $C_3$–$C_7$ carbocylic ring. Exemplary groups include cyclopropyl, cyclobutyl, cyclopentyl, cyclohexyl, cycloheptyl, cycloctyl, cyclodecyl, cyclododecyl, and adamantyl. A "substituted cycloalkyl" is substituted with one or more alkyl or substituted alkyl groups as described above, or one or more groups described above as alkyl substituents.

The terms "heterocycle", "heterocyclic" and "heterocyclo" each refer to a fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Thus, the term "heterocycle" includes heteroaryl groups as described above. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, dioxanyl, isothiazolidinyl, thietanyl, thiiranyl, triazinyl, and triazolyl, and the like.

Exemplary bicyclic hetrocyclic groups include 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Also included are smaller heterocyclos, such as epoxides and aziridines.

A "substituted heterocycle" will be substituted with one or more alkyl or aralkyl groups as described above, and/or one or more groups described above as alkyl substituents.

Unless otherwise indicated, when reference is made to a specifically-named heterocyclo or heteroaryl, the reference is intended to include those systems having the maximum number of non-cumulative double bonds or less than that maximum number of double bonds. Thus, for example, the term "isoquinoline" refers to isoquinoline and tetrahydroisoquinoline. The term "diazepine" refers to a heterocyclo ring having at least one seven atom ring with two nitrogen atoms in the seven membered ring, including a fully saturated or unsaturated diazepine.

The term "heteroatoms" shall include oxygen, sulfur and nitrogen.

The term "haloalkyl" means an alkyl having one or more halo substituents

The term "perfluoromethyl" means a methyl group substituted by one, two, or three fluoro atoms, i.e., $CH_2F$, $CHF_2$ and $CF_3$. The term "perfluoroalkyl" means an alkyl group having from one to five fluoro atoms, such as pentafluoroethyl.

The term "haloalkoxy" means an alkoxy group having one or more halo substituents. For example, "haloalkoxy" includes —$OCF_3$.

The term "carbocyclic" means a saturated or unsaturated unsaturated monocyclic or bicyclic ring in which all atoms of all rings are carbon. Thus, the term includes cycloalkyl and aryl rings. The carbocyclic ring may be substituted in which case the substituents are selected from those recited above for cycloalkyl and aryl groups.

When the term "unsaturated" is used herein to refer to a ring or group, the ring or group may be fully unsaturated or partially unsaturated.

Definitions for the various other groups that are recited above in connection with substituted alkyl, substituted alkenyl, substituted alkynyl, substituted aryl, substituted heterocycle, substituted cycloalkyl, and so forth, are as follows: alkoxy is —$OR^a$, alkanoyl is —$C(=O)R^a$, aryloxy is —OAr, alkanoyloxy is —$OC(=O)R^a$, amino is —$NH_2$, alkylamino is —$NHR^a$, arylamino is —NHAr, aralkylamino is —NH—$R^b$—Ar, disubstituted amine or dialkylamino is —$NR^cR^d$, alkanoylamino is —NH—$C(=O)R^a$, aroylamino is —NH—$C(=O)$Ar, aralkanoylamino is —NH—$C(=O)R^b$—Ar, thiol is —SH, alkylthio is —$SR^a$, arylthio is —SAr, aralkylthio is —S—$R^b$—Ar, alkylthiono is —$S(=O)R^a$, arylthiono is —$S(=O)$Ar, aralkylthiono is —$S(=O)R^b$—Ar, alkylsulfonyl is —$SO_{(q)}R^a$, arylsulfonyl is —$SO_{(q)}$Ar, arylsulfonylamine is —$NHSO_{(q)}$Ar, alkylsulfonylamine is —$NHSO_2R^a$, aralkylsulfonyl is —$SO_{(q)}R^b$Ar, sulfonamido is —$SO_2NH_2$, nitro is —$NO_2$, carboxy is —$CO_2H$, carbamyl is —$CONH_2$, substituted carbamyl is —$C(=O)NHR^c$ or —$C(=O)NR^cR^d$, alkoxycarbonyl is —$C(=O)OR^a$, carboxyalkyl is —$R^b$—$CO_2H$, sulfonic acid is —$SO_3H$, arylsulfonylamine is —$NHSO_{(q)}$Ar, guanidino is

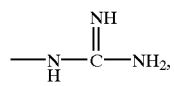

and ureido is

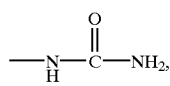

wherein $R^a$ is alkyl as defined above, $R^b$ is alkylene as defined above, $R^c$ and $R^d$ are selected from alkyl, aryl, and aralkyl, Ar is an aryl as defined above, and q is 2 or 3.

Throughout the specification, groups and substituents thereof may be chosen by one skilled in the field to provide stable moieties and compounds.

The compounds of Formula (I) may form salts which are also within the scope of this invention. Pharmaceutically acceptable (i.e. non-toxic, physiologically acceptable) salts are preferred, although other salts are also useful, e.g., in isolating or purifying the compounds of this invention. All references to compounds of Formula (I) herein are intended to include without limitation compounds of Formulae (Ia) to (Ii) as well as compounds of Formula (II and (IIa)-(IIh). All references to compounds of Formula (II) are intended to include compounds of Formulae (IIa) to (IIh).

The compounds of Formula (I) may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds for Formula (I) may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art.

Salt forms of the compounds may be advantageous for improving the compound dissolution rate and oral bioavailability. For select compounds of Formula (I), mesylate and/or bisulfate salts were successfully obtained (see, e.g., Example 125 herein). Both mesylate and bisulfate salts were found to be non-hygroscopic, highly water soluble, and stable in solid state In addition, zwitterions ("inner salts") may be formed.

All stereoisomers of the compounds of the instant invention are contemplated, either in admixture or in pure or substantially pure form. The definition of compounds according to the invention embraces all the possible stereoisomers and their mixtures. It embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

Compounds of the Formula (I) may also have prodrug forms. Any compound that will be converted in vivo to provide the bioactive agent (i.e., the compound for formula I) is a prodrug within the scope and spirit of the invention.

Various forms of prodrugs are well known in the art. For examples of such prodrug derivatives, see:

a) *Design of Prodrugs,* edited by H. Bundgaard, (Elsevier, 1985) and Methods in Enzymology, Vol.42, p. 309–396, edited by K. Widder, et al. (Acamedic Press, 1985);

b) *A Textbook of Drug Design and Development,* edited by Krosgaard-Larsen and H. Bundgaard, Chapter 5, "Design and Application of Prodrugs," by H. Bundgaard, p. 113–191 (1991); and c) H. Bundgaard, *Advanced Drug Delivery Reviews,* 8, 1–38 (1992), each of which is incorporated herein by reference.

It should further be understood that solvates (e.g., hydrates) of the compounds of Formula (I) are also with the scope of the present invention. Methods of solvation are generally known in the art.

Preferred Compounds

Preferred embodiments of the invention comprise preferred compounds of Formulae (I) and (II), and methods of treating conditions associated with p38 kinase activity comprising administering preferred compounds of Formulae (I) and (II). Preferred compounds are those having Formula (I),

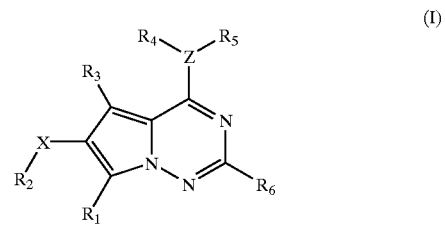

and pharmaceutically acceptable salts, prodrugs, or solvates thereof, wherein:

$R_3$ is methyl, $-CF_3$, or $-OCF_3$,

X is selected from $-C(=O)-$, $-CO_2-$, $-NR_{10}C(=O)-$, and $-C(=O)NR_{10}-$, or X is absent;

Z is N;

$R_1$ is hydrogen, $-CH_3$, $-OH$, $-OCH_3$, $-SH$, $-SCH_3$, $-OC(=O)R_{21}$, $-S(=O)R_{22}$, $-SO_2R_{22}$, $-SO_2NR_{24}R_{25}$, $-CO_2R_{21}$, $-C(=O)NR_{24}R_{25}$, $-NH_2$, $-NR_{21}SO_2NR_{24}R_{25}$, $-NR_{21}SO_2R_{22}$, $-NR_{24}C(=O)R_{25}$, $-NR_{24}CO_2R_{25}$, $-NR_{21}C(=O)NR_{24}R_{25}$, halogen, nitro, or cyano;

$R_2$ is hydrogen, $C_{2-6}$ alkyl, substituted $C_{1-4}$alkyl, aryl, aralkyl, substituted aryl, substituted aralkyl, cycloalkyl, substituted cycloalkyl, heterocycle, or substituted heterocycle, or optionally-substituted cycloalkylalkyl or heterocycloalkyl;

$R_4$ is aryl or heteroaryl substituted with one $R_{12}$ and zero to three $R_{13}$;

$R_5$ and $R_{10}$ independently are selected from hydrogen and lower alkyl;

$R_6$ is hydrogen, alkyl, substituted alkyl, aryl, substituted aryl, heterocyclo, substituted heterocyclo, $-NR_7R_8$, $-OR_7$, or halogen;

$R_{12}$ is carbamyl, sulfonamido, arylsulfonylamine, or ureido, each of which is optionally substituted with up to two of hydroxy, alkyl, substituted alkyl, alkoxy, aryl, substituted aryl, and aralkyl, or $R_{12}$ is alkylsulfonylamine;

$R_{13}$ at each occurrence is independently selected from alkyl, substituted alkyl, halo, trifluoromethoxy, trifluoromethyl, —$OR_{14}$, —C(=O)alkyl, —OC(=O)alkyl, —$NR_{15}R_{16}$, —$SR_{15}$, —$NO_2$, —CN, —$CO_2R_{15}$, —$CONH_2$, —$SO_3H$, —S(=O)alkyl, —S(=O)aryl, —$NHSO_2$-aryl-$R_{17}$, —$NHSO_2$-alkyl, —$SO_2NHR_{17}$, —$CONHR_{17}$, and —NHC(=O)$NHR_{17}$;

$R_{14}$ is hydrogen, alkyl, or aryl;

$R_{15}$ is hydrogen or alkyl;

$R_{16}$ is hydrogen, alkyl, aralkyl, or alkanoyl;

$R_{17}$ is hydrogen, hydroxy, alkyl, substituted alkyl, alkoxy, aryl, substituted aryl, or aralkyl;

$R_7$, $R_8$, $R_{10}$, $R_{11}$, $R_{21}$, $R_{24}$, and $R_{25}$ are independently selected from hydrogen and alkyl; and $R_{22}$ is alkyl or substituted alkyl.

In compounds of Formula (I), preferably the group $R_3$ is methyl, trifluoromethyl, or methoxy, most preferably methyl; X is preferably —$CO_2$—, —$NR_{10}$C(=O)—, or —C(=O)$NR_{10}$—, more preferably —C(=O)NH—; Z is preferably N; $R_4$ is preferably substituted aryl or substituted heteroaryl, more preferably phenyl substituted with at least one of carbamyl, substituted carbamyl, arylsulfonylamido, substituted arylsulfonylamido, ureido, or substituted ureido, and optionally substituted with one or two $C_{1-4}$alkyl or halogen. Most preferably $R_4$ is phenyl substituted with at least one of —C(=O)NHO($C_{1-4}$alkyl) or —C(=O)NH (optionally substituted phenyl), and also is optionally substituted with $C_{1-4}$alkyl. $R_5$ is preferably hydrogen or lower alkyl, more preferably hydrogen.

In preferred compounds, $R_1$ and $R_6$ may be selected from groups of substituents as defined herein; however, advantageously they are selected from hydrogen, $CH_3$, —OH, —$OCH_3$, halogen, nitro, and cyano, and most preferably $R_1$ and $R_6$ are hydrogen. $R_2$ preferably is alkyl, aryl, substituted aryl, aralkyl, substituted aralkyl, heteroaryl, or substituted heteroaryl, more preferably straight or branched $C_{2-6}$alkyl or optionally-substituted benzyl. The mesylate salt is the preferred form of salt.

Accordingly, preferred compounds further comprise those having the Formula (II),

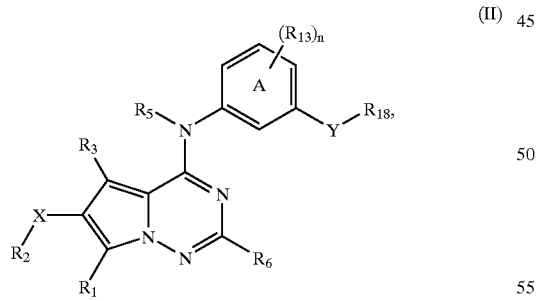

and pharmaceutically acceptable salts, prodrugs, or solvates thereof, wherein:

$R_3$ is methyl, —$CF_3$, or —$OCH_3$;

X is —C(=O)$NR_{10}$—, —$NR_{10}$C(=O)—, —C(=O)—, or —$CO_2$—;

Y is —C(=O)NH—, —NHC(=O)NH—, or —$NHSO_2$—;

$R_{10}$ is hydrogen or lower alkyl;

$R_{18}$ is selected from hydrogen, alkyl, alkoxy, aryl, and aryl substituted with one to three $R_{19}$, except that when Y is —$NHSO_2$—, $R_{18}$ is —$C_{1-4}$alkyl, aryl or aryl substituted with $R_{19}$;

$R_{13}$ is attached to any available carbon atom of phenyl ring A and at each occurrence is independently selected from alkyl, substituted alkyl, halo, trifluoromethoxy, trifluoromethyl, —$OR_{14}$, —C(=O)alkyl, —OC(=O)alkyl, —$NR_{15}R_{16}$, —$SR_{15}$, —$NO_2$, —CN, —$CO_2R_{15}$, —$CONH_2$, —$SO_3H$, —S(=O)alkyl, —S(=O)aryl, —$NHSO_2$—aryl-$R_{17}$, —$SO_2NHR_{17}$, —$CONHR_{17}$, and —NHC(=O)$NHR_{17}$;

$R_{14}$, $R_{15}$, $R_{16}$ and $R_{17}$ are hydrogen or alkyl;

$R_{19}$ at each occurrence is selected from alkyl, halo, trifluoromethoxy, trifluoromethyl, hydroxy, alkoxy, alkanoyl, alkanoyloxy, thiol, alkylthio, ureido, nitro, cyano, carboxy, carboxyalkyl, carbamyl, alkoxycarbonyl, alkylthiono, arylthiono, arylsulfonylamine, sulfonic acid, alkysulfonyl, sulfonamido, and aryloxy, wherein each group $R_{19}$ may be further substituted by hydroxy, alkyl, alkoxy, aryl, or aralkyl;

n is 0, 1 or 2, and $R_1$, $R_2$ and $R_6$ are as defined above for compounds of Formula (I).

More preferred are compounds having the Formula (IIa) or (IIb):

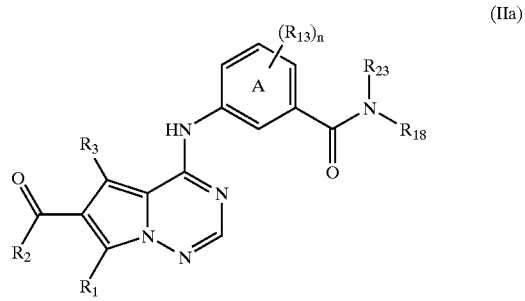

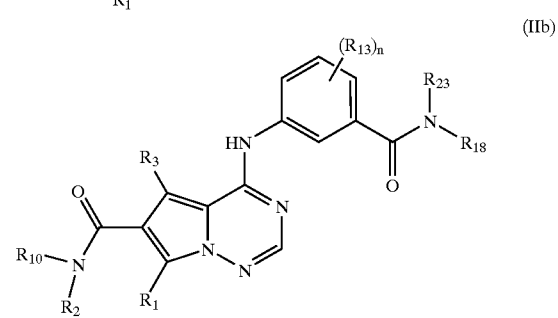

and pharmaceutically acceptable salts, prodrugs, or solvates thereof, wherein:

$R_3$ is methyl;

$R_1$ and $R_{10}$ are hydrogen or —$CH_3$;

$R_2$ is selected from hydrogen; straight or branched $C_{2-6}$alkyl; cycloalkyl optionally substituted with keto and/or up to two $R_{27}$; phenyl optionally substituted with up to two $R_{27}$; heterocycle optionally substituted with keto and/or up to two $R_{27}$; and $C_{1-4}$alkyl substituted with up to three of halogen, trifluoromethyl, cyano, $OR_{28}$, $NR_{28}R_{29}$, $CO_2R_{28}$, aryl, heterocycle, and/or cycloalkyl, wherein the aryl, heterocycle, and/or cycloalkyl in turn are optionally substituted with up to two of halogen, hydroxy, alkoxy, haloalkyl, haloalkoxy, nitro, cyano and alkyl;

$R_{18}$ is hydroxy, $C_{1-4}$alkoxy, phenyl, or phenyl substituted with one or two $R_{19}$;

$R_{13}$ and $R_{19}$ are selected from lower alkyl, halogen, trifluoromethoxy, trifluoromethyl, hydroxy, $C_{1-4}$alkoxy, nitro, and cyano;

$R_{27}$ at each occurrence is independently selected from hydrogen, alkyl, trifluoromethyl, trifluoromethoxy, halogen, cyano, nitro, amino, hydroxy, alkoxy, phenyl, benzyl, phenyloxy, and benzyloxy;

$R_{28}$ and $R_{29}$ at each occurrence are independently selected from hydrogen, alkyl, alkenyl, phenyl, and benzyl; and n is 0, 1 or 2.

When $R_2$ is a heterocyclo, advantageously it is selected from diazepinyl, morpholinyl, piperidinyl, and pyrrolidinyl, said heterocycle being optionally substituted with $C_{1-4}$alkyl, phenyl, and/or benzyl.

Most preferred are compounds having the formula,

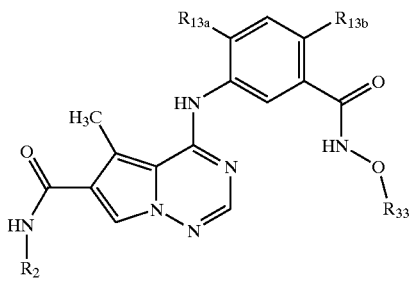

in which $R_{13a}$ and $R_{13b}$ are hydrogen, $CH_3$, OH, $OCH_3$, $CF_3$, cyano, or halogen, $R_2$ is $C_{2-6}$alkyl or optionally substituted benzyl, $R_{33}$ is lower alkyl, and n is 0 or 1.

Utility

The compounds of the invention are selective inhibitors of p38 kinase activity, and in particular, isoforms p38α and p38β. Accordingly, compounds of formula (I) have utility in treating conditions associated with p38 kinase activity. Such conditions include diseases in which cytokine levels are modulated as a consequence of intracellular signaling via p38, and in particular, diseases that are associated with an overproduction of cytokines IL-1, IL-4, IL-8, and TNF-α. As used herein, the terms "treating" or "treatment" encompass either or both responsive and prophylaxis measures, e.g., designed to inhibit or delay the onset of the disease or disorder, achieve a full or partial reduction of the symptoms or disease state, and/or to alleviate, ameliorate, lessen, or cure the disease or disorder and/or its symptoms. When reference is made herein to inhibition of "p-38α/β kinase," this means that either p38α and/or p38β kinase are inhibited. Thus, reference to an $IC_{50}$ value for inhibiting p-38α/β kinase means that the compound has such effectiveness for inhibiting at least one of, or both of, p38α and p38β kinases.

In view of their activity as inhibitors of p-38α/β kinase, compounds of Formula (I) are useful in treating p-38 associated conditions including, but not limited to, inflammatory diseases, autoimmune diseases, destructive bone disorders, proliferative disorders, angiogenic disorders, infectious diseases, neurodegenerative diseases, and viral diseases.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, scleroderma, chronic thyroiditis, Grave's disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoisosis, bone resorption disease, allograft rejections, fever and myalgias due to infection, cachexia secondary to infection, meloid formation, scar tissue formation, ulcerative colitis, pyresis, influenza, osteoporosis, osteoarthritis and multiple myeloma-related bone disorder, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovascularization, and infantile haemangiomas; viral diseases including acute hepatitis infection (including hepatitis A, hepatitis B and hepatitis C), HIV infection and CMV retinitis, AIDS<ARC or malignancy, and herpes; stroke, myocardial ischemia, ischemia in stroke heart attacks, organ hyposia, vascular hyperplasia, cardiac and renal reperfusion injury, thrombosis, cardiac hypertrophy, thrombin-induced platelet aggregation, endotoxemia and/or toxic shock syndrome, and conditions associated with prostaglandin endoperoxidase syndase-2.

In addition, p38 inhibitors of this invention inhibit the expression of inducible pro-inflammatory proteins such as prostaglandin endoperoxide synthase-2 (PGHS-2), also referred to as cyclooxygenase-2 (COX-2). Accordingly, additional p38-associated conditions include edema, analgesia, fever and pain, such as neuromuscular pain, headache, pain caused by cancer, dental pain and arthritis pain. The inventive compounds also may be used to treat veterinary viral infections, such as lentivirus infections, including, but not limited to equine infectious anemia virus; or retro virus infections, including feline immunodeficiency virus, bovine immunodeficiency virus, and canine immunodeficiency virus.

When the terms "p38 associated condition" or "p38 associated disease or disorder" are used herein, each is intended to encompass all of the conditions identified above as if repeated at length, as well as any other condition that is affected by p38 kinase activity.

The present invention thus provides methods for treating such conditions, comprising administering to a subject in need thereof an effective amount of at least one compound of Formula (I) or a salt thereof. The methods of treating p38 kinase-associated conditions may comprise administering compounds of Formula (I) alone or in combination with each other and/or other suitable therapeutic agents useful in treating such conditions. Exemplary of such other therapeutic agents include corticosteroids, rolipram, calphostin, CSAIDs, 4-substituted imidazo [1,2-A]quinoxalines as disclosed in U.S. Pat. No. 4,200,750 and in S. Ceccarelli et al, "*Imidazo*[1, 2-*a*]quinoxalin-4-*amines: A Novel Class of Nonxanthine $A_1$-Adenosine Receptor Antagonists,*" European Journal of Medicinal Chemistry* Vol. 33, (1998), at pp.

943–955; Interleukin-10, glucocorticoids, salicylates, nitric oxide, and other immunosuppressants; nuclear translocation inhibitors, such as deoxyspergualin (DSG); non-steroidal antiinflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, Prograf); cytotoxic drugs such as azathiprine and cyclophosphamide; TNF-α inhibitors such as tenidap, anti-TNF antibodies or soluble TNF receptor, and rapamycin (sirolimus or Rapamune) or derivatives thereof.

The above other therapeutic agents, when employed in combination with the compounds of the present invention, may be used, for example, in those amounts indicated in the Physicians'Desk Reference (PDR) or as otherwise determined by one of ordinary skill in the art. In the methods of the present invention, such other therapeutic agent(s) may be administered prior to, simultaneously with, or following the administration of the inventive compounds.

The present invention also provides pharmaceutical compositions capable of treating p38-kinase associated conditions, including TNF-α, IL-1, and/or IL-8 mediated conditions, as described above. The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

The compounds of Formula (I) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The effective amount of a compound of the present invention may be determined by one of ordinary skill in the art, and includes exemplary dosage amounts for a mammal of from about 0.05 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of p38 enzyme levels.

Compounds of formula (I), including the compounds described in the examples hereof, have been tested in one or more of the assays described below and have shown activity as inhibitors of p38α/β enzymes and TNF-α.

Biological Assays

Generation of p38 Kinases cDNAs of human p38α, β and γ isozymes were cloned by PCR. These cDNAs were subcloned in the pGEX expression vector (Pharmacia). GST-p38 fusion protein was expressed in *E. Coli* and purified from bacterial pellets by affinity chromatography using glutathione agarose. p38 fusion protein was activated by incubating with constitutively active MKK6. Active p38 was separated from MKK6 by affinity chromatography. Constitutively active MKK6 was generated according to Raingeaud et al. [*Mol. Cell. Biol.*, 1247–1255 (1996)].

TNF-α Production by LPS-Stimulated PBMCs

Heparinized human whole blood was obtained from healthy volunteers. Peripheral blood mononuclear cells (PBMCs) were purified from human whole blood by Ficoll-Hypaque density gradient centrifugation and resuspended at a concentration of $5 \times 10^6$ ml in assay medium (RPMI medium containing 10% fetal bovine serum). 50 ul of cell suspension was incubated with 50 ul of test compound (4×concentration in assay medium containing 0.2% DMSO) in 96-well tissue culture plates for 5 minutes at RT. 100 ul of LPS (200 ng/ml stock) was then added to the cell suspension and the plate was incubated for 6 hours at 37° C. Following incubation, the culture medium was collected and stored at −20° C. TNF-α concentration in the medium was quantified using a standard ELISA kit (Pharmingen-San Diego, Calif.). Concentrations of TNF-α and $IC_{50}$ values for test compounds (concentration of compound that inhibited LPS-stimulated TNF-α production by 50%) were calculated by linear regression analysis.

p38 Assay

The assays were performed in V-bottomed 96-well plates. The final assay volume was 60 µl prepared from three 20 µl additions of enzyme, substrates (MBP and ATP) and test compounds in assay buffer (50 mM Tris pH 7.5, 10 mM $MgCl_2$, 50 mM NaCl and 1 mM DTT). Bacterially expressed, activated p38 was pre-incubated with test compounds for 10 min. prior to initiation of reaction with substrates. The reaction was incubated at 25° C. for 45 min. and terminated by adding 5 µl of 0.5 M EDTA to each sample. The reaction mixture was aspirated onto a pre-wet filtermat using a Skatron Micro96 Cell Harvester (Skatron, Inc.), then washed with PBS. The filtermat was then dried in a microwave oven for 1 min., treated with MeltilLex A scintillation wax (Wallac), and counted on a Microbeta scintillation counter Model 1450 (Wallac). Inhibition data were analyzed by nonlinear least-squares regression using Prizm (GraphPadSoftware). The final concentration of reagents in the assays are ATP, 1 µM; [γ-$^{33}$P]ATP, 3 nM,; MBP (Sigma, #M1891), 2 µg/well; p38, 10 nM; and DMSO, 0.3%.

TNF-α Production by LPS-Stimulated Mice

Mice (Balb/c female, 6–8 weeks of age, Harlan Labs; n=8/treatment group) were injected intraperitoneally with 50 ug/kg lipopolysaccharide (LPS; *E coli* strain 0111:B4, Sigma) suspended in sterile saline. Ninety minutes later, mice were sedated by $CO_2$:$O_2$ inhalation and a blood sample was obtained. Serum was separated and analyzed for TNF-alpha concentrations by commercial ELISA assay per the manufacturer's instructions (R&D Systems, Minneapolis, Minn.).

Test compounds were administered orally at various times before LPS injection. The compounds were dosed either as suspensions or as solutions in various vehicles or solubilizing agents.

Abbreviations

For ease of reference, the following abbreviations are employed herein, including the methods of preparation and Examples that follow:

Ph=phenyl
Bz=benzyl
t-Bu=tertiary butyl
Me=methyl
Et=ethyl
Pr=propyl
Iso-P=isopropyl
MeOH=methanol
EtOH=ethanol
EtOAc=ethyl acetate
Boc=tert-butyloxycarbonyl
CBZ=carbobenzyloxy or carbobenzoxy or benzyloxycarbonyl
DCM=dichloromethane
DCE=1,2-dichloroethane
DMF=dimethyl formamide
DMSO=dimethyl sulfoxide
TFA=trifluoroacetic acid
THF=tetrahydrofuran
HATU=O-(7-Azabenzotriazol-1-yl-N,N,N',N'-tetramethyluronim hexafluorophosphate
KOH=potassium hydroxide
$K_2CO_3$=potassium carbonate
$POCl_3$=phosphorous oxychloride
KOtBu=potassium t-butoxide
EDC or EDCI=1-(3-Dimethylaminopropyl)-3-ethylcarbodiimide hydrochloride
DIPEA=diisopropylethylamine
HOBt=1-hydroxybenzotriazole hydrate
m-CPBA=m-chloroperbenzoic acid
NaH=sodium hydride
NaOH=sodium hydroxide
$Na_2S_2O_3$=sodium thiosulfate
Pd=palladium
Pd/C=palladium on carbon
min=minute(s)
L=liter
mL=milliliter
µL=microliter
g=gram(s)
mg=milligram(s)
mol=moles
mmol=millimole(s)
meq=milliequivalent
RT or rt=room temperature
ret. t.=HPLC retention time (minutes)
sat or sat'd=saturated
aq.=aqueous
TLC=thin layer chromatography
HPLC=high performance liquid chromatography
RP HPLC=reverse phase HPLC
LC/MS=high performance liquid chromatography/mass spectrometry
MS=mass spectrometry
NMR=nuclear magnetic resonance
mp=melting point In the Examples, "HPLC Condition A" refers to YMC S5 ODS 4.6×50 mm Ballistic column, 4 mL/min flow rate, 4 min linear gradient elution (Start solvent %B=0; Final solvent %B=100), solvent A=10% MeOH/90% $H_2O$/0.2% $H_3PO_4$.

Methods of Preparation

Compounds of formula I may generally be prepared according to the following schemes and the knowledge of one skilled in the art. In the schemes, the groups $R_1$–$R_6$, $R_{10}$, $R_{13}$, $R_{18}$, $R_{23}$, X and Z are as described herein for compounds of Formula (I).

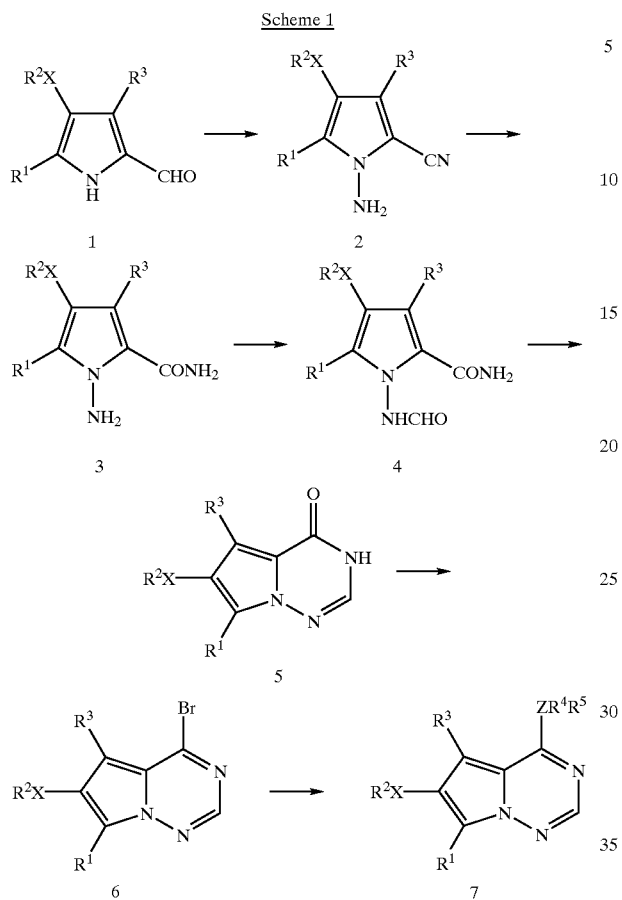

Scheme 1

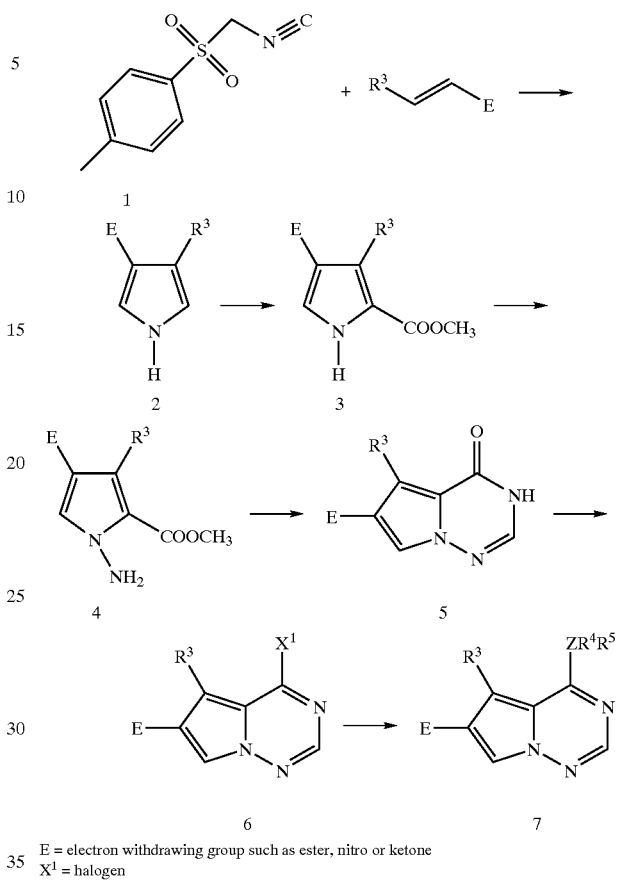

Scheme 2

E = electron withdrawing group such as ester, nitro or ketone
$X^1$ = halogen

An optionally substituted 2-formylpyrrole (1) is reacted with an aminating reagent, such as hydroxylamine-O-sulfonic acid, in an aq. solvent at rt, followed by treatment under cooling with a base such as KOH, to form compound (2).

Compound (2) is reacted with an aq. base such as KOH at rt to form compound (3). Compound (3) is reacted with an acylating agent, such as formic acid, in an aq. solvent, to form compound (4). Compound (4) is cyclized with a base such as sodium methoxide in MeOH with heating to form compound (5). Compound (5) is halogenated, e.g., with phosphorus oxybromide at elevated temperature, to form compound (6). Compound (6) is reacted with an amine such as an aniline in an organic solvent, such as acetonitrile, to form product (7) of Scheme 1.

Compound (7) of Scheme 1 where $R_1$=halogen can be prepared from compound (7) of Scheme 1 where $R_1$=hydrogen by reaction with a halogenating agent such as bromine in a suitable solvent such as acetic acid.

Compounds (1) may be obtained from substituted pyrroles by formylation, e.g., by reaction with phosphorus oxychloride and DMF. A methylpyrrole may be obtained by reduction of a formylpyrrole, e.g., by reaction with lithium aluminum hydride.

Reacting an anion of tosylmethyl isocyanide (TosMIC) (1) with a Michael acceptor such as ethyl crotonate provides disubstituted pyrrole (2). Treatment of pyrrole (2) with an acylating agent such as trichloroacetyl chloride in the presence of a Lewis acid such as aluminum chloride at from rt to 50° C., followed by treatment with sodium methoxide, affords trisubstituted pyrrole (3). Compound (3) can be obtained by warming an aldehyde, such as acetaldehyde, with 2 equivalents of ethyl isocyanoacetate in the presence of a base, such as DBU, in an organic solvent, such as THF. Alternatively, compound (3) can be obtained following the procedure of M. Suzuki, M. Miyoshi, and K. Matsumoto *J. Org. Chem.* 1974, 39 (1980).

Pyrrole (3) can be aminated by an aminating reagent, such as diphenyl phosphoryl hydroxylamine, in the presence of a base, such as NaH, at rt in organic solvents, such as DMF, to form N-aminated pyrrole (4). Compound (4) is cyclized by heating at from 120 to 195° C. with formamide to afford 1,2,4-triazine (5). Treatment of compound (5) with a halogenating agent, such as phosphorous oxybromide, at from 60 to 115° C., in the presence or absence of a co-solvent such as DCE, affords compound (6).

Compound (6) is reacted with an amine, such as an aniline in an organic solvent, such as DMF, to obtain compound (7). Alternatively, compound (7) can be obtained by treating (6) with an anion of a heterocyclic compound, such as oxindole, in an organic solvent such as THF.

An anion of TosMIC (1) can be made by treating a solution of it in DMSO with a base such as NaH at rt or a solution of it in THF with lithium hexamethyldisilazane at −78° C.

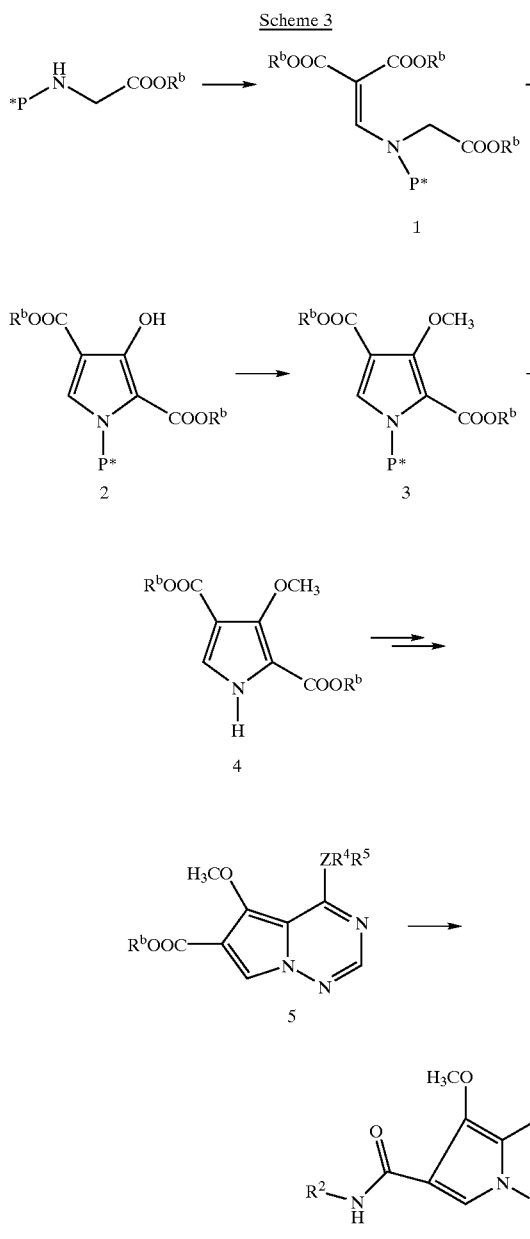

wherein P* protecting group, Rb=R⁶ described hereinbefore

A suitably N-protected ester of glycine, such as with benzyl group, can be added to dialkyl methylene malonate at from rt to 80° C. to obtain compound (1). Compound (1) is cyclized to form pyrrole (2) upon treatment with a strong base, such as lithium hexamethyldisilazane, at from −78° C. to rt in an organic solvent such as THF. Pyrrole (2) is alkylated by treatment with an alkylating agent, such as iodomethane or dimethyl sulfate, in the presence of a base, such as $K_2CO_3$, in an organic solvent, such as acetone or DMF to yield compound (3).

Deprotection of compound (3) can be achieved, when optionally protected by groups such as benzyl, by hydrogenation over a catalyst, such as Pd, in the presence of ammonium formate. Compound (4) is converted to compound (5) via cyclization as described for compound (5) of Scheme 2.

Hydrolysis of the ester group in compound (5) can be achieved by treatment with a base such as aq. KOH. The resulting acid can be coupled with an amine in the presence of a coupling agent, such as DCC or PyBrop.

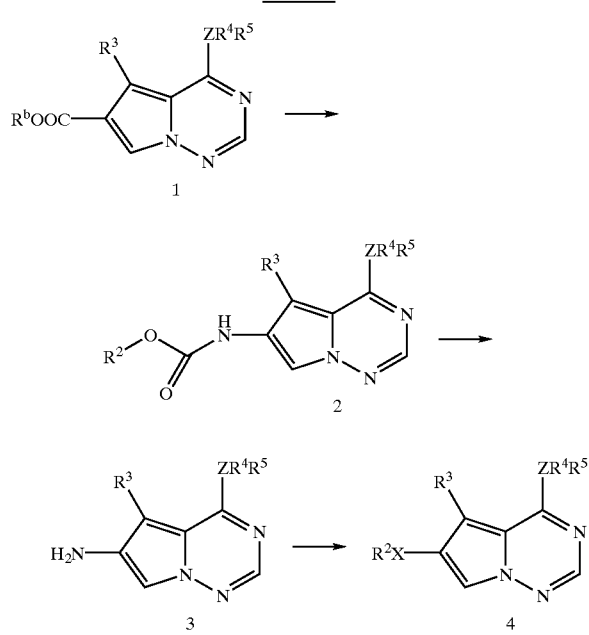

wherein X=$NR^{10}$, $NR^{10}CO$, $NR^{10}CO$, $NR^{10}CONR11$, $NR^1COO$, $NR^{10}SO_2$, $NR^{10}SO_2NR^{11}$, as described hereinbefore.

Compound (5) from Scheme 3 can be converted to carboxylic acid (1) (wherein $R_3$ is methoxy or is as otherwise defined herein) by treatment with a base such as aq. KOH. This acid undergoes Curtis rearrangement by treatment with diphenyl phosphoryl azide in the presence of an alcohol, such as benzyl alcohol, in an organic solvent, such as 1,4-dioxane, to afford compound (2).

The carbamate group of compound (2) can be deprotected, when optionally protected by groups such as CBZ, by hydrogenation over a catalyst, such as Pd, to obtain compound (3). The amino group of compound (3) can be acylated to form compound (4), e.g., by treatment with a carboxylic acid in the presence of a coupling agent such as DCC, or sulfonylated, e.g., by treatment with a sulfonyl chloride. Alternatively, the amino group of compound (3) may be alkylated with alkyl halides or may undergo reductive anation with aldehydes in the presence of a reducing agent, such as sodium cyanoborohydride.

Scheme 5

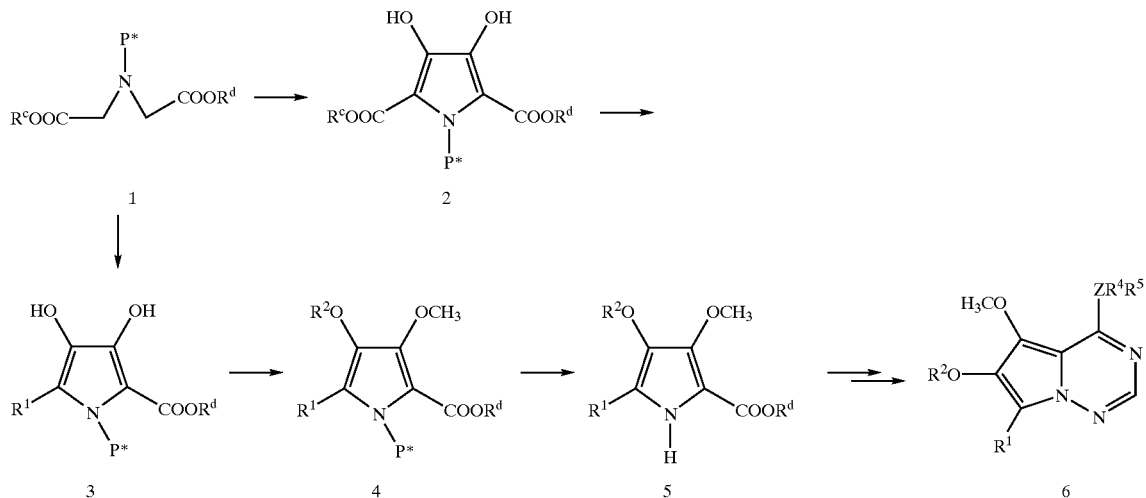

wherein P*=protecting group; $R^c$, $R^d=R^6$; and $R^1$=H or $COOR^{21}$ as described hereinbefore.

Suitably protected compound (1) (imino dicarboxylate) can be cyclized by treatment with dialkyl oxalate in the presence of a base, such as sodium methoxide, in an organic solvent, such as MeOH. Compound (2) upon selective deprotection, such as with TFA when optionally protected by tert-butyl ester, undergoes decarboxylation to afford compound (3) where $R^1$=H. This step is omitted to form compound (3) where $R^1=COOR^{21}$.

The hydroxy group of compound (3) can be etherified by reaction with an alkylating agent, such as dimethyl sulfate. Compound (4) can be deprotected by hydrogenation, when optionally protected such as with a benzyl group, to obtain compound (5). Compound (5) is then converted to compound (6) in an analogous manner to that described for compound (4) of Scheme 3 and compounds (4) through (7) of Scheme 2.

Scheme 6

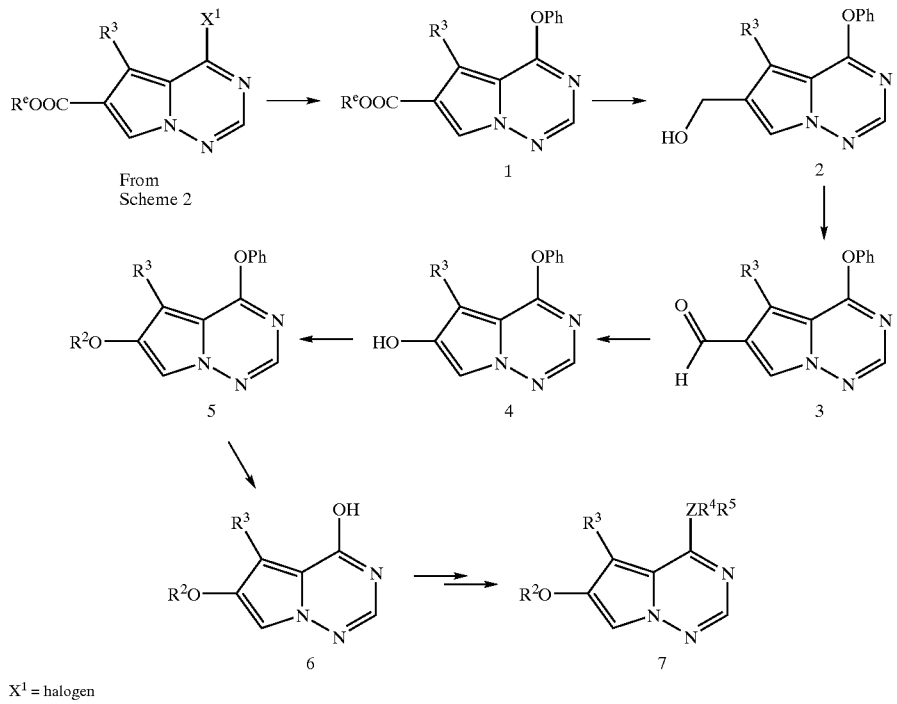

$X^1$ = halogen

Compound (6) of Scheme 2 can be etherified at the 4-position, e.g., by treatment with phenoxide anion to form compound (1). Reduction of compound (1) with a reducing agent, such as DIBAL, in an organic solvent, such as toluene, affords alcohol (2). Oxidation of the alcohol (2) can be achieved by treatment with MnO$_2$ at an elevated temperature in an organic solvent, such as toluene, to form (3). Treatment of compound (3) with an oxidant, such as m-CPBA in an organic solvent, such as DCM, followed by aq. hydrolysis with a base, such as potassium bicarbonate, affords the hydroxy compound (4).

Alkylation of the phenolic group of compound (4) with an agent, such as iodomethane, in the presence of a base, such as NaH, at from rt to 100° C., affords compound (5). Hydrolysis of compound (5) can be achieved by treatment with an acid, such as aq. HCl, at an elevated temperature to afford (6). Compound (6) can be converted to compound (7) with procedures analogous to those described in Scheme 2.

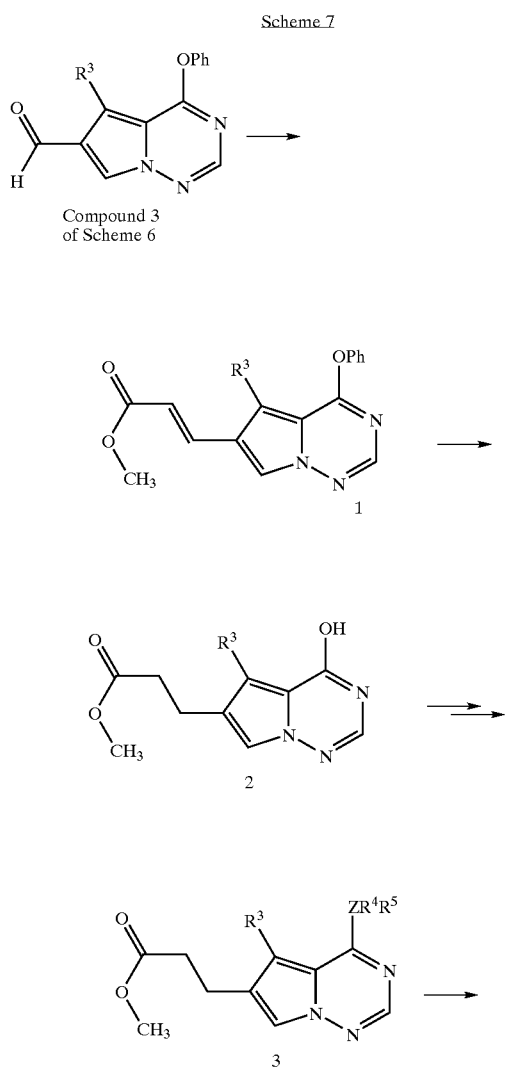

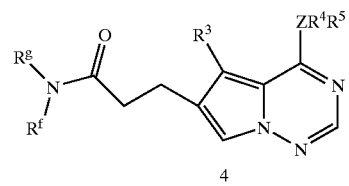

wherein $R^f$, $R^g = R^2$ as described hereinbefore

Compound (3) from Scheme 6 can undergo a Wittig reaction, e.g., with phosphonates such as methyl diethylphosphonoacetate, in an organic solvent, such as DCE, in the presence of a base, such as NaH, to afford compound (1). The double bond of compound (1) can be hydrogenated by treatment with hydrogen in the presence of a catalyst, such as Pd. Compound (2) can be converted to (3) by procedures described in Scheme 2.

Hydrolysis of the ester, as described hereinbefore, followed by coupling of the resulting acid with an amine in the presence of a coupling agent, such as DCC, affords compound (4).

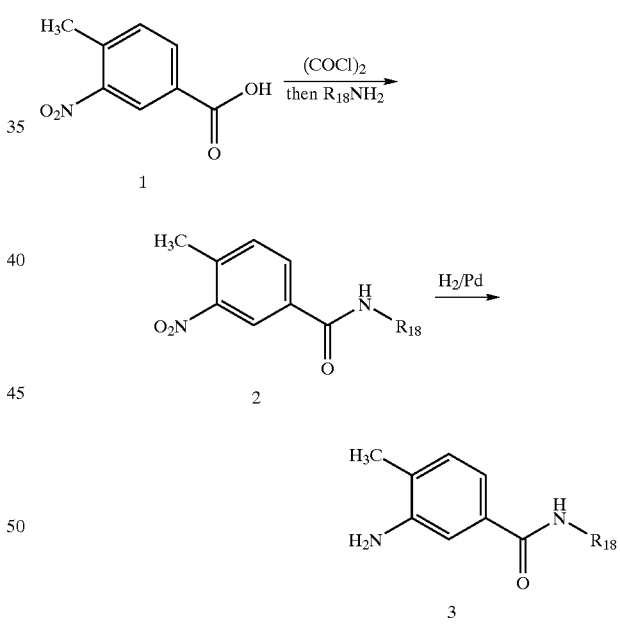

Commercially-available compound (1) can be reacted with oxalyl chloride with heating and then concentrated in vacuo and reacted with an amine $R_{18}NH_2$ in the presence of a base, such as diisopropylamine, in an organic solvent, such as DCM to yield compound (2). Compound (2) can be reacted with hydrogen in the presence of a catalyst, such as Pd, in an alcoholic solvent, such as EtOH, at rt to afford compound (3). Compound (3) can then be used as in Scheme 9 to produce compounds (6) of Scheme 9.

Scheme 9

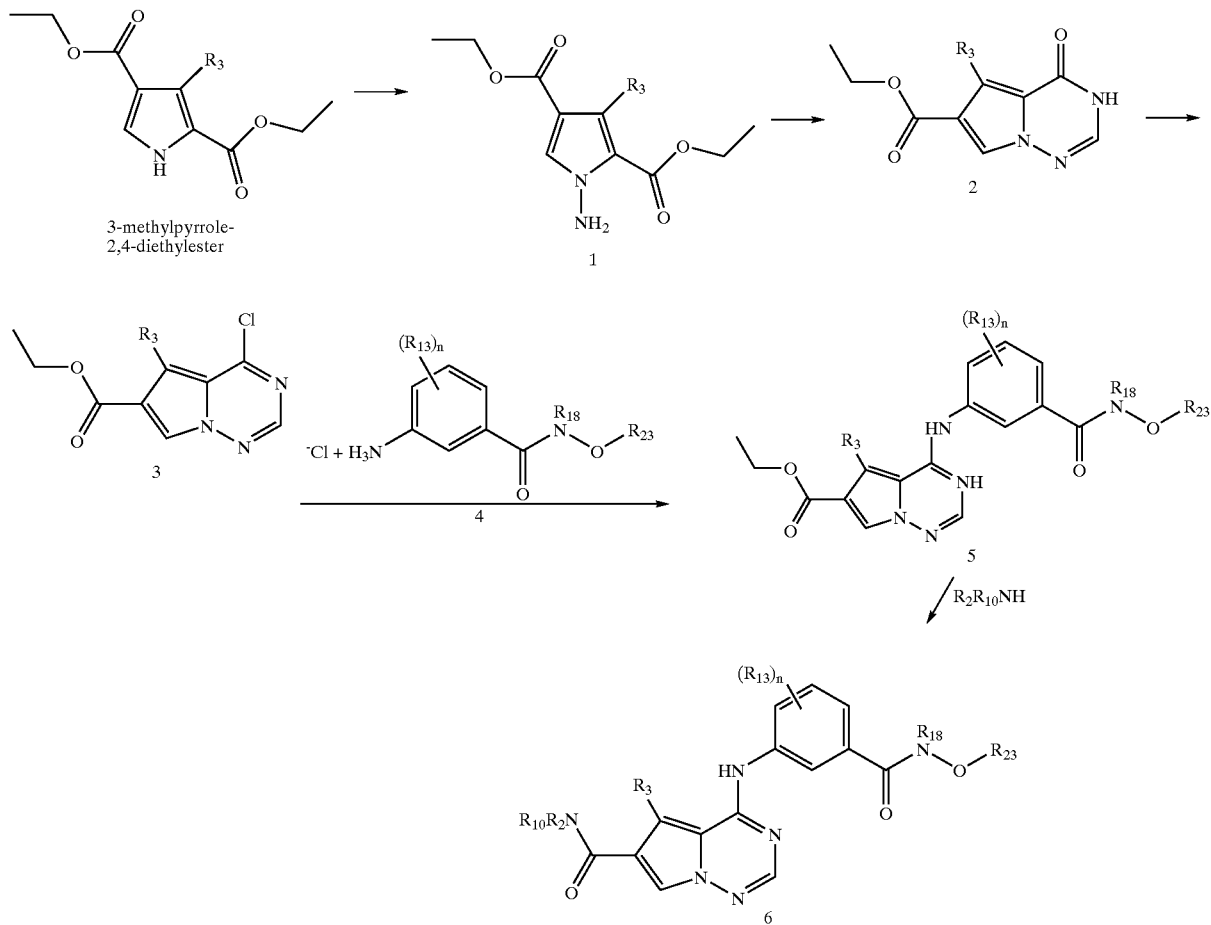

3-methyl-1-pyrrole-2,4-diethyl ester can be reacted with chloramine in ether to produce compound (1). Reacting compound (1) in formamide with acetic acid produces compound (2). Compound (2) can be reacted with DIPEA and POCl$_3$ in toluene to produce compound (3). Compound (3) can be reacted with DIPEA and compound (4) in DMF to produce compound (5). Compound (5) can be reacted in THF with NaOH to produce an acid intermediate which upon treatment with HOBt, EDCI and the appropriate amine (NR$_2$R$_{10}$) in DMF produces compounds (6).

Compound (4) can be prepared by 1) reacting commercially-available 4-amino-3-methylbenzoic acid and N-(tert-butoxycarbonyl)anhydride in THF to produce a BOC-protected aniline intermediate; 2) reacting the aniline intermediate with -(3-dimethylaminopropyl)-3-ethylcarbodiimide hydrochloride, HOBt, and DMF, followed by addition of methoxyamine hydrochloride and DIPEA to produce a BOC-protected N-methoxyamide intermediate; and 3) reacting that methoxyamide intermediate in a solution of HCl in dioxane to produce compound (4) as a hydrochloride salt. Alternatively, compound (4) can be prepared as shown in Scheme 8.

Scheme 10

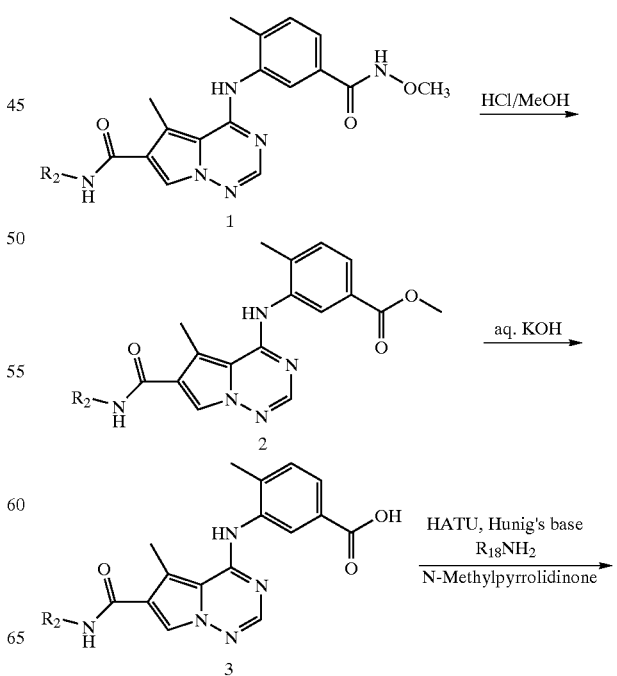

-continued

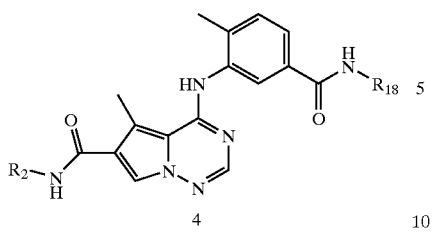

A substituted hydroxamate (1) can be reacted with acid, such as HCl, in anhydrous MeOH, to afford compound (2). Compound (2) can be reacted with an aq. base such KOH with heating to form compound (3). Compound (3) is reacted with an amine $R_{18}NH_2$ in the presence of a coupling reagent, such as HATU, and a base such as diisopropylamine, in an organic solvent, such as N-methylpyrrolidinone to afford compounds (4). Alternatively, compounds (4) may generally be prepared as outlined in Schemes 8 and 9.

Scheme 11

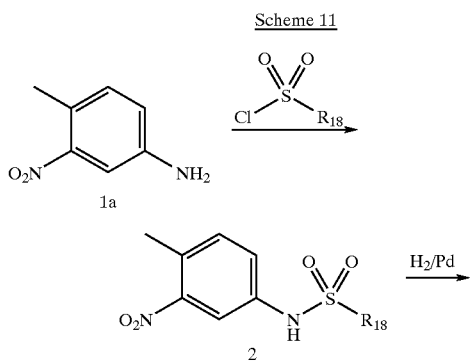

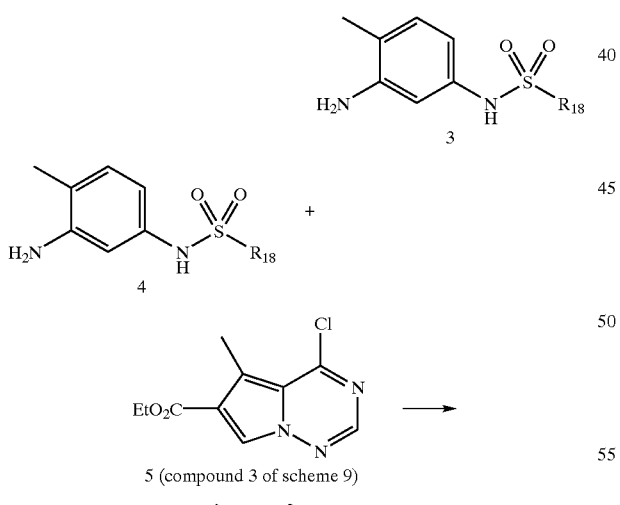

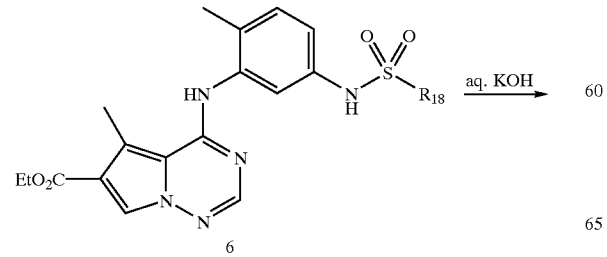

-continued

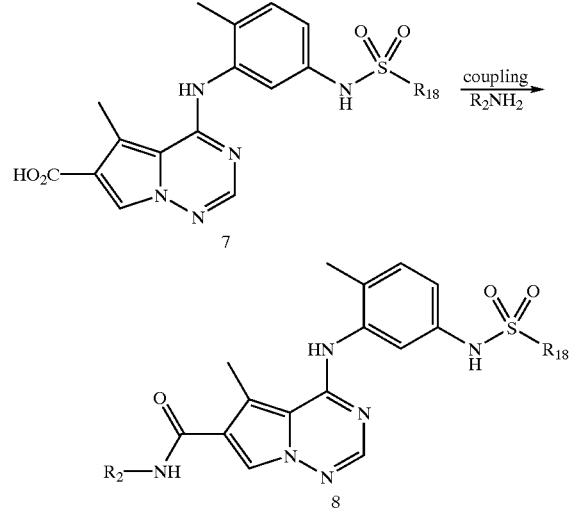

Commercially-available compound (1a) can be reacted with a sulfonyl chloride in the presence of a base, such as TEA, in an organic solvent, such as DCM to yield compound (2). Reaction of compound (2) with hydrogen in the presence of a catalyst, such as Pd in a solvent, such as MeOH, yields compound (3). Reaction of compound (3) with chloride (5) (compound 3 of scheme 9) in an organic solvent, such as DMF, at rt affords compound (6).

Reaction of compound (6) with aq. KOH with heating affords compound (7). Compound (7) can be reacted with an amine $R_2NH_2$ in the presence of a coupling reagent, such as EDCI, and a base such as diisopropylamine, in an organic solvent, such as DMF to afford compound (8).

Scheme 12

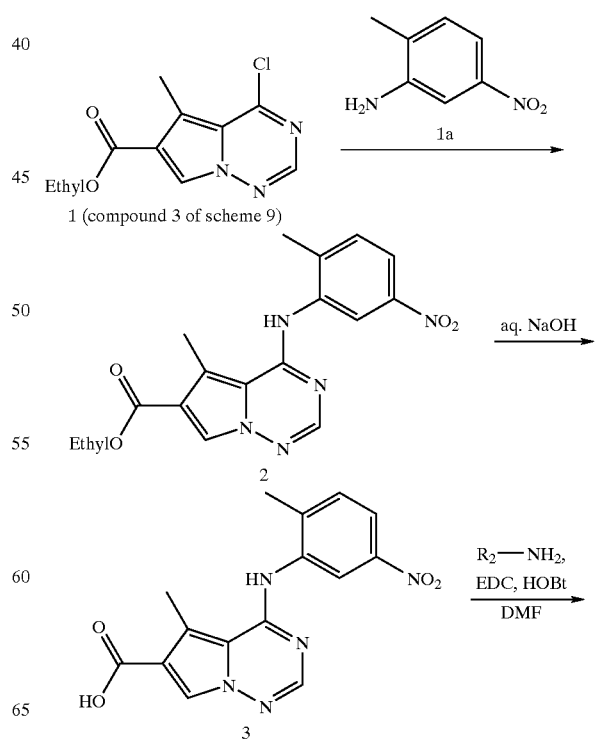

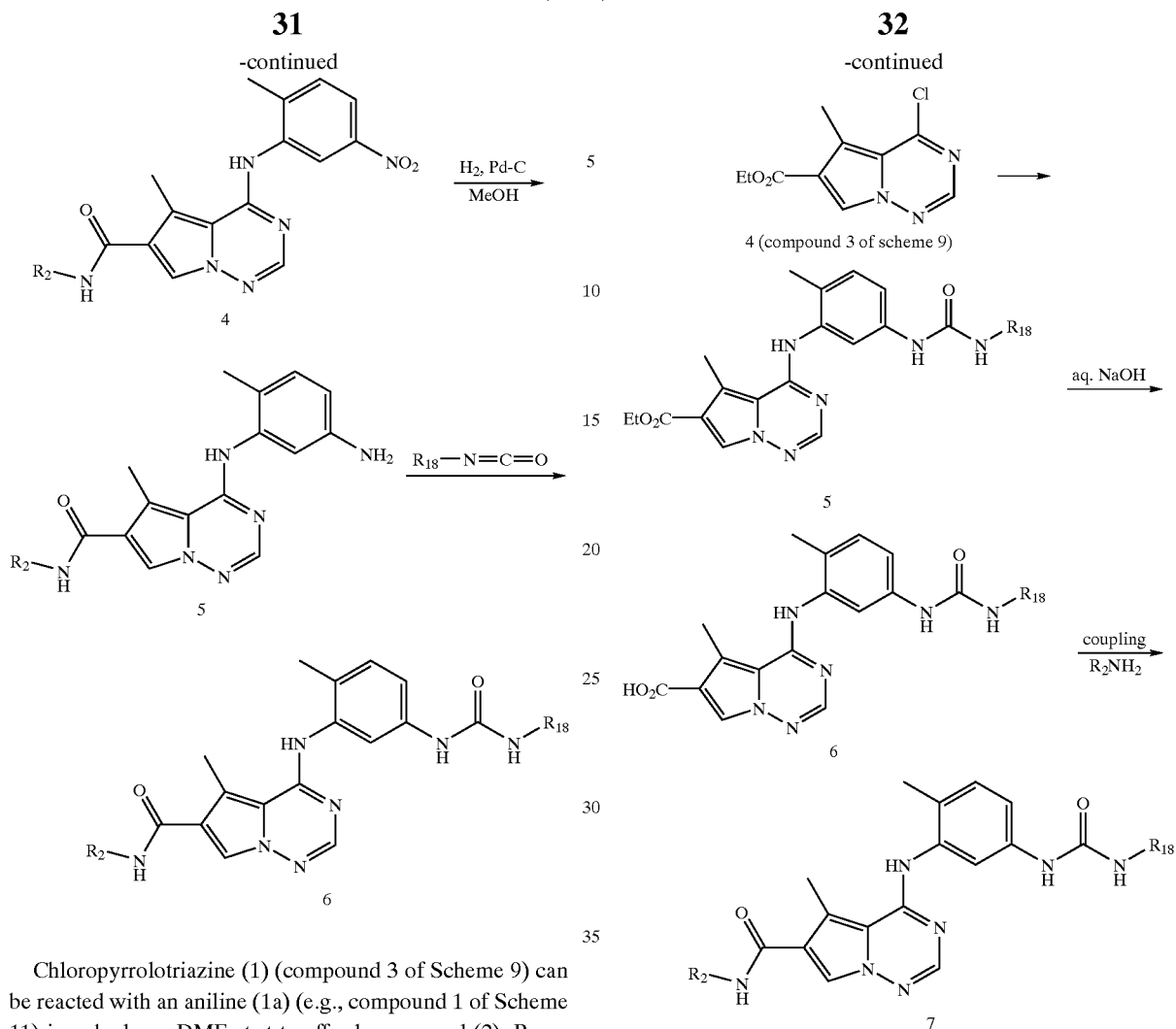

Chloropyrrolotriazine (1) (compound 3 of Scheme 9) can be reacted with an aniline (1a) (e.g., compound 1 of Scheme 11) in anhydrous DMF at rt to afford compound (2). Reaction of compound (2) with an aq. base such as NaOH with heating affords compound (3). Compound (3) can be reacted with an amine $R_2NH_2$ in the presence of a coupling reagent, such as HOBt, with or without a base such as diisopropylamine, in an organic solvent, such as DMF to afford compound (4). Compound (4) can be reacted with hydrogen in the presence of a catalyst, such as Pd/C, in an organic solvent, such as MeOH to afford compound (5). Reaction of compound (5) with an isocyanate in an organic solvent, such as DCE affords compound (6).

Commercially-available compound (1a) (compound 1a of Schemes 11 and 12), can be reacted with carbonyl diimidazole and with an amine $R_{18}NH_2$ in an organic solvent, such as DCE, to yield compound (8). Reaction of compound (8) with hydrogen in the presence of a catalyst, such as Pd, in an alcoholic solvent such as EtOH affords compound (9). Reaction of (9) with chloride (1) in an organic solvent, such as DMF, affords compound (10). Reaction of (10) with aq. NaOH with heating affords product (11). Product (11) can be reacted with an amine $R_2NH_2$ in the presence of a coupling reagent, such as EDCI, and a base such as diisopropylamine, in an organic solvent, such as DMF to afford compound (7).

Scheme 13

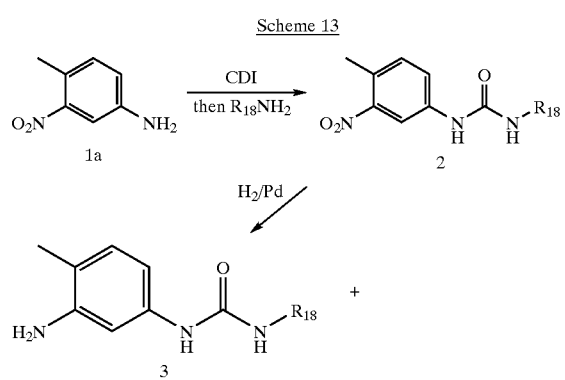

Scheme 14

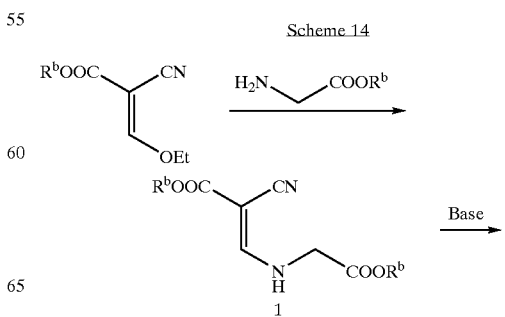

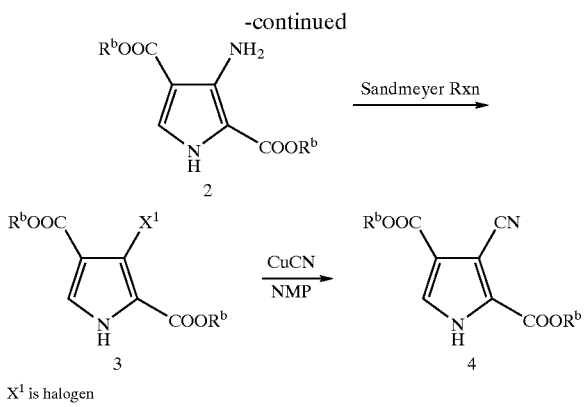

X¹ is halogen

Glycine ethyl ester can be added to an alkyl alkoxy methylene cyanoacetate at from rt to 80° C. to obtain compound (1). Compound (1) is cyclized to form pyrrole (2) upon treatment with a strong base, such as lithium hexamethyldisilazane, at from −78° C. to rt in an organic solvent such as THF. Pyrrole (2) is converted to a halide using sodium nitrite in an organic solvent, such as DMF, and a halide source, such as CuBr to yield compound (3). Compound (3) can be converted to compound (4) using CuCN in an organic solvent such as NMP at elevated temperatures. Alternatively, compound (2) can be directly converted to compound (4) using sodium nitrite in an organic solvent, such as DMF, and a cyanide source such as CuCN. Compounds (3) and (4) can then be used as described in previous schemes (e.g., as compound 3 of Scheme 2), to form compounds of Formula (I) wherein $R_3$ is halogen or cyano.

In addition, other compounds of formula I may be prepared using procedures generally known to those skilled in the art. In particular, the following examples provide additional methods for the preparation of the compounds of this invention.

The invention will now be further described by the following working examples, which are preferred embodiments of the invention. HPLC purifications were done on C18 reverse phase (RP) columns using water MeOH mixtures and TFA as buffer solution. These examples are illustrative rather than limiting. There may be other embodiments that fall within the spirit and scope of the invention as defined by the appended claims.

EXAMPLE 1

1-[2,3-Dihydro-6-(pyrrolo[2,1-f][1,2,4]triazin-4-ylamino)-1H-indol-1-yl]ethanone

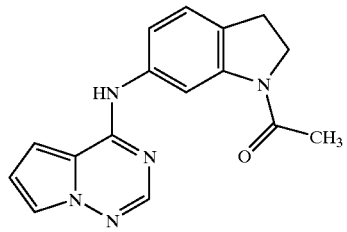

A. 4-Bromo-pyrrolo[2,1-f][1,2,4]triazine

A mixture of 50 mg (0.37 mmol) of pyrrolo[2,1-f][1,2,4]triazin-4(3H)-one [prepared as described in S. A. Patil, B. A. Otter and R. S. Klein, *J. Het. Chem.*, 31, 781–786 (1994)] and 0.5 g of phosphorus oxybromide was heated and kept at 60° C. for 20 min. under argon. A clear orange melt was initially obtained which solidified to a yellow solid on continued heating. Ice was added with vigorous stirring. The mixture was extracted twice with EtOAc. The combined extracts were washed with sat. NaHCO$_3$ and brine, dried (MgSO$_4$), and the solvent removed to afford 63 mg of crude Compound A as an orange oil which crystallized on standing. (M+H)$^+$=198$^+$, 200$^+$.

B. Example 1

A solution of 60 mg (0.3 mmol) of Compound A and 1-acetyl-6-aminoindoline in 1.5 ml of acetonitrile was stirred overnight at rt under argon. A white precipitate was obtained which was removed by filtration. The filter cake was suspended in 10% isopropanol/methylene chloride for extraction. Sat'd NaHCO$_3$ was added and the mixture stirred until a solution was obtained. The organic layer was separated and washed with brine, dried (MgSO$_4$), and the solvent removed. Purification by chromatography on silica gel with EtOAc yielded 4% of Example 1 as a white solid. (M+H)$^+$=294.

EXAMPLE 2

4-(2,3-Dihydro-1H-indol-1-yl)-5-methylpyrrolo[2,1-f][1,2,4]triazine-6-carboxylic acid methyl ester

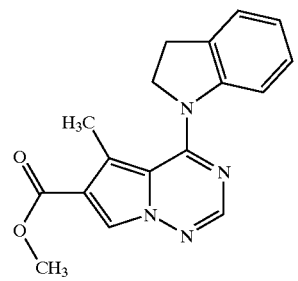

A. Methylpyrrole-3-carboxylic acid methyl ester

To a 1.0 M solution of lithium hexamethyldisilazide in THF (41 mL, 41 mmol) at −78° C. was added dropwise over 45 min. a solution of tosylmethyl isocyanide (8.1 g, 41 mmol) in THF. After the reaction was stirred for an additional 45 min., a solution of methyl crotonate in THF was added over 40 min. The reaction was warmed to 25° C. and stirred for 5 h. The reaction was diluted with EtOAc and washed with sat. aq. NaHCO$_3$. The aqueous layer was extracted three times with EtOAc, dried (Na$_2$SO$_4$), concentrated, and purified by chromatography on silica gel eluting with a gradient of 20–30% EtOAc in hexanes to provide Compound A.

B. 3-Methylpyrrole-2,4-dicarboxylic acid dimethyl ester

To a suspension of aluminum chloride (106.4 g, 798 mmol) in DCE (700 mL) at −40° C. under nitrogen was added dropwise trichloroacetyl chloride (89 mL, 798 mmol). A solution of Compound A (37 g, 266 mmol) in DCE (200 mL) was added. The reaction mixture was gradually warmed to rt and stirred over the weekend (65 hr). A cold and pre-prepared mixture of aluminum chloride (53.2 g) and trichloroacetyl chloride (44.6 g) in DCE (450 mL) was added to the reaction mixture. After an additional 24 hr, the mixture was carefully poured into an ice-water bath (2 L) and the pH of the solution adjusted to 2.0. The organic layer was separated and the aqueous layer extracted with DCM.

The combined organic extracts were washed with 3 N HCl, brine, dried (Na₂SO₄), and concentrated in vacuo to give a dark oil. This oil was dissolved in MeOH (400 mL), and the resulting solution was cooled to 0° C. under nitrogen. To this solution was added sodium methoxide (25% in MeOH) until the pH of the solution was 10. After 1 hr, the mixture was concentrated and then diluted with ice water (1 L) and the pH of the mixture was adjusted to 6. The mixture was extracted with DCM (3×1 L). The combined extracts were washed with NaHCO₃, brine, dried (Na₂SO₄), and concentrated in vacuo. The brown solid obtained was purified by chromatography on silica gel eluting with EtOAc in hexanes to provide 44.3 g (84%) of Compound B. MS: [M+H]⁻=196.

C. 1-Amino-3-methylpyrrole-2,4-dicarboxylic Acid dimethyl ester

To a suspension of NaH (60% in oil, 33 mg, 0.83 mmol) in DMF (5 mL) at 0° C. was added Compound B (46 g, 213 mmol) in DMF (3 mL). After 10 min. at 0° C., diphenyl phosphoryl hydroxylamine (0.19 g, 0.83 mmol) was added neat followed by DMF (31 mL). The reaction mixture was stirred for 2 hrs at 25° C. and then quenched with pH 7 phosphate buffer (15 mL). The mixture was extracted with EtOAc (4×20 mL). The combined extracts were dried (Na₂SO₄) and after purification by chromatography on silica gel eluting with 25–30% EtOAc in hexanes, 38 g (84%) of Compound C was obtained as white solid. ESI [M+H]⁻=213.1.

D. 5-Methylpyrrolo[2,1-f][1,2,4]triazin-4(3H)-one-6-carboxylic acid methyl ester Compound C (38 g, 179 mmol) was combined with formamide (400 mL) and heated to 165° C. for 6 hr. The reaction was diluted with water (5 mL), extracted with EtOAc (3×10 mL), dried (Na₂SO₄), and concentrated. The crude material was purified by washing with ether/hexanes (7/3) to provide 33.4 g (90%) of Compound D as a white solid. ESI MS: [M–H]⁻=206.0

E. 4-Chloro-5-methyl-6-carbomethoxypyrrolo[2,1-f][1,2,4]triazine

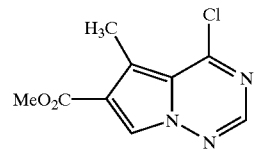

Phosphorous oxychloride (2.5 mL) was combined with Compound D (100 mg, 0.483 mmol) and heated at 100° C. overnight. The melt was allowed to cool to rt and dissolved in EtOAc. The mixture was neutralized with aq. NaHCO₃ and extracted twice with EtOAc. The combined organic washes were dried (Na₂SO₄), and concentrated to provide 101 mg (93%) of Compound E. MS: (M+H)⁺=226.6.

F. Example 2

A mixture of Compound E (20 mg, 0.09 mmol) and indoline (21 mg, 0.177 mmol) in CH₃CN (1 mL) was shaken for 4 hrs. Then DMF (0.2 mL) was added, and the crude mixture was purified by preparative HPLC to provide 12.2 mg (45%) of Example 2 as a white solid. [M+H]⁺=309.2; ¹H NMR (CDCl₃): δ8.06 (s, 1H), 7.91 (s, 1H), 7.20 (m, 1H), 7.01 (m, 1H), 6.93–6.91 (m, 2H), 4.15 (t, J=7.8 Hz, 2H), 3.18 (s, 3H), 3.09 (t, J=7.8 Hz, 2H), 2.35 (s, 3H).

EXAMPLES 3–6

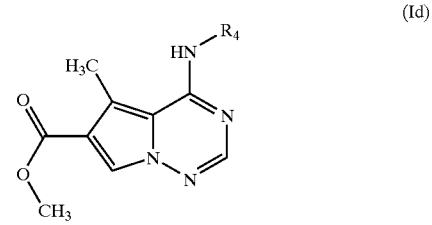

(Id)

Compounds having the formula (Id), wherein the group R₄ has the values listed in Table 1, were prepared following the method of Example 2, using an appropriately-selected amine compound in place of indoline in step F.

TABLE 1

| Ex. | R₄ | Compound Name | Data |
|---|---|---|---|
| 3 | (3-hydrazinocarbonylphenyl-amino group) | 4-[[3-(Hydrazinocarbonyl)phenyl]amino]-5-methylpyrrolo[2,1-f][1,2,4]triazine-6-carboxylic acid methyl ester | MS: [M+H]⁺=341.2; ¹H NMR (d-DMSO): δ 7.79(s, 1H), 7.58(s, 1H), 7.11–7.05(m, 3H), 6.72(d, J=8.1Hz, 1H), 5.23(br s, 2H), 3.76(s, 3H), 2.67(s, 3H) |
| 4 | (3-acetylaminophenyl group) | 4-[3-(Acetylamino)phenyl]amino]-5-methylpyrrolo[2,1-f][1,2,4]triazine-6-carboxylic acid methyl ester | MS: [M+H]⁺=340.2; ¹H NMR (CDCl₃): δ 7.81(s, 1H), 7.75(s, 1H), 7.51(s, 1H), 7.20–7.07(m, 3H), 3.80(s, 3H), 2.84(s, 3H), 1.90 (s, 3H) |
| 5 | (1-acetyl-2,3-dihydroindol-6-yl group) | 4-[(1-Acetyl-2,3-dihydro-1H-indol-6-yl)amino]-5-methylpyrrolo[2,1-f][1,2,4]triazine-6-carboxylic acid methyl ester | MS: [M+H]⁺=366.2; ¹H NMR (CDCl₃): δ 8.14(d, J=8.6Hz, 1H), 7.95(s, 1H), 7.82(s, 1H), 7.51(s, 1H), 7.12 (d, J=8.6Hz, 1H), 4.03 (t, J=7.8Hz, 2H), 3.81 (s, 3H), 3.18(t, J=7.8 Hz, 2H), 2.67(s, 3H), 2.19(s, 3H) |

TABLE 1-continued

| Ex. | R4 | Compound Name | Data |
|---|---|---|---|
| 6 | 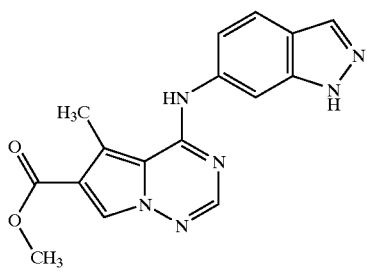 | 5-Methyl-4-[[2-methyl-5-[(methylsulfonyl)amino]phenyl]amino]pyrrolo[2,1-f][1,2,4]triazine-6-carboxylic acid methyl ester | MS: [M+H]$^+$=390.2; $^1$H NMR (CDCl$_3$): δ 8.04(br s, 1H), 7.95(s, 1H), 7.87(s, 1H), 7.09–6.99(m, 2H), 3.82(s, 3H), 3.00(s, 3H), 2.89 (s, 3H), 2.28(s, 3H) |

EXAMPLE 7

4-(1H-Indazol-6-ylamino)-5-methylpyrrolo[2,1-f][1,2,4]triazine-6-carboxylic acid methyl ester

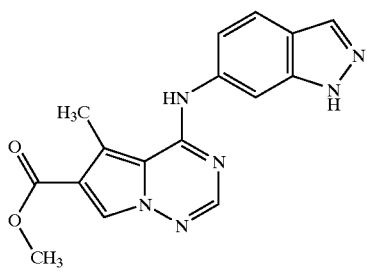

A mixture of Compound E from Example 2 (20 mg, 0.09 mmol) and 6-aminoindazole (18 mg, 0.13 mmol) in CH$_3$CN (1 mL) and DMSO (0.5 mL) was shaken for 4 hrs. The mixture was filtered, washed with CH$_3$CN, and the crude material was purified by preparative HPLC to provide Example 7 as a white solid (13 mg, 45%). [M+H]$^+$=323.1; $^1$H NMR (CDCl$_3$): δ8.37 (s, 1H), 7.99 (s, 1H), 7.94 (d, J=7.4 Hz, 1H), 7.68 (d, J=4.2 Hz, 1H), 7.00 (dd, J=7.4, 4.2 Hz, 1H), 3.83 (s, 3H), 2.91 (s, 3H).

EXAMPLE 8

5-Methyl-4-[[3-[(methylsulfonyl)amino]phenyl]amino]pyrrolo[2,1-f][1,2,4]triazine-6-carboxylic acid methyl ester

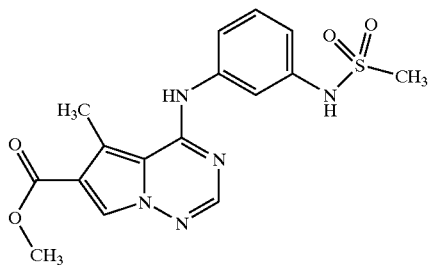

Compound E of Example 2 was dissolved in DMF (2 mL), and then 3-(methylsulfonylamino)aniline (54 mg, 0.3 mmol) was added. The reaction mixture was stirred for 4 hrs under argon at 25° C. The crude reaction mixture was purified by preparative HPLC. The material obtained appeared to be a salt of the desired compound. The material was dissolved in EtOAc and washed with sat'd NaHCO$_3$. Evaporating the solvent gave 24 mg (40%) of Example 8. MS: [M+H]$^+$376.2; $^1$H NMR (d-DMSO): δ8.89 (s, 1H), 8.14 (s, 1H), 7.95 (s, 1H), 7.55 (s, 1H), 7.38 (s, 1H), 7.34–7.32 (m, 2H), 7.01 (d, J=8.0 Hz, 1H), 3.81 (s, 3H), 3.02 (s, 3H), 2.82 (s, 3H).

EXAMPLE 9

4-[[3-(Aminosulfonyl)phenyl]amino]-5-methylpyrrolo[2,1-f][1,2,4]triazine-6-carboxylic acid methyl ester

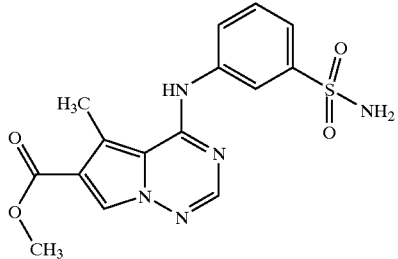

Compound E from Example 2 (20 mg, 0.09 mmol) was mixed with 3-aminobenzenesulfonamide (23 mg, 0.13 mmol) in DMF (1 mL) and shaken for 4 hrs. Evaporating the extracting solvent and purification by preparative HPLC gave 8.6 mg (58%) of Example 9 as a solid. MS: [M+H]$^+$= 362; $^1$H NMR (d-DMSO): δ9.08 (s, 1H), 8.18 (s, 2H), 7.98 (s, 1H), 7.91–7.89 (m, 1H), 7.62–7.58 (m, 2H), 7.42 (s, 2H), 3.81 (s, 3H), 2.84 (s, 3H)

EXAMPLES 10–14

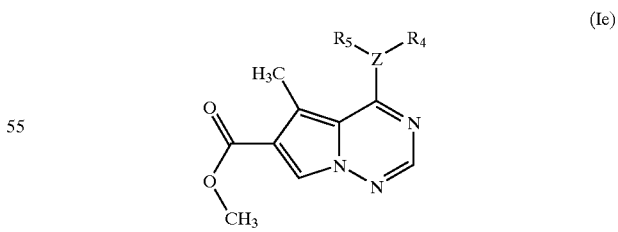

(Ie)

Compounds having the formula (Ie), wherein the groups Z, R$_4$, and R$_5$ together have the values listed in Table 2, were prepared following the method of Example 9, except instead of 3-aminobenzenesulfonamide, an appropriately-selected amino compound was used.

TABLE 2

| Ex. | —ZR4R5 | Compound Name | Data |
|---|---|---|---|
| 10 | (3-[(butylamino)sulfonyl]phenylamino- structure) | 4-[[3-[(Butylamino)sulfonyl]phenyl]amino]-5-methylpyrrolo[2,1-f][1,2,4]triazine-6-carboxylic acid methyl ester | MS: [M+H]$^+$=418.2; $^1$H NMR (CDCl$_3$): δ 8.07(s, 1H), 7.97(s, 1H), 7.85(s, 1H), 7.84–7.82(m, 1H), 7.58(d, J=8.0Hz, 1H), 7.49–7.45(m, 2H), 3.82 (s, 3H), 2.93–2.89(m, 2H), 2.81(s, 3H), 1.44–1.18(m, 4H), 0.84(t, J=7.4Hz, 3H) |
| 11 | (3-aminosulfonyl-4-methylphenylamino structure) | 4-[[3-(Aminosulfonyl)-4-methylphenyl]amino]-5-methylpyrrolo[2,1-f][1,2,4]triazine-6-carboxylic acid methyl ester | MS: [M+H]$^+$=376.2; $^1$H NMR (CDCl$_3$): δ 8.05(s, 1H), 7.91(s, 1H), 6.97(d, J=7.8Hz, 1H), 6.31(s, 1H), 6.23(d, J=7.8Hz, 1H), 4.22(t, J=7.7Hz, 2H), 3.84(s, 3H), 2.84(t, J=7.7Hz, 2H), 2.55(s, 3H). |
| 12 | (6-acetylamino-3-pyridinylamino structure) | 4-[[6-(Acetylamino)-3-pyridinyl]amino]-5-methylpyrrolo[2,1-f][1,2,4]triazine-6-carboxylic acid methyl ester | MS: [M+H]$^+$=341.2; $^1$H NMR (d-DMSO): δ 10.51 (s, 1H), 8.87(s, 1H), 8.53 (s, 1H), 8.14–8.01(m, 3H), 7.93(s, 1H), 3.80(s, 3H), 2.83(s, 3H), 2.32(s, 3H). |
| 13 | (3,4-dimethoxyphenylamino structure) | 4-[(3,4-Dimethoxyphenyl)amino]-5-methylpyrrolo[2,1-f][1,2,4]triazine-6-carboxylic acid methyl ester | MS: [M+H]$^+$=343.2; $^1$H NMR (CDCl$_3$): δ 7.91(s, 1H), 7.85(s, 1H), 7.21(s, 1H), 7.00(dd, J=8.6, 2.8 Hz, 1H), 6.82(d, J=8.6 Hz, 1H), 3.84–3.82(3s, 9H), 2.88(s, 3H) |
| 14 | (2,3-dihydro-3-oxo-1H-indazol-2-yl structure) | 4-(2,3-Dihydro-3-oxo-1H-indazol-2-yl)-5-methylpyrrolo[2,1-f][1,2,4]triazine-6-carboxylic acid methyl ester | MS: [M+H]$^+$=324.2; $^1$H NMR (CDCl$_3$): δ 9.65(s, 1H), 8.14(s, 1H), 7.85(s, 1H), 7.48(d, J=8.2Hz, 1H), 7.42–7.37(m, 2H), 7.14–7.12(m, 1H), 3.86 (s, 3H), 2.84(s, 3H) |
| 15 | (5-aminocarbonyl-2,3-dihydro-2-oxo-1H-indol-3-yl structure) | 4-[5-(Aminocarbonyl)-2,3-dihydro-2-oxo-1H-indol-3-yl]-5-methylpyrrolo[2,1-f][1,2,4]triazine-6-carboxylic acid methyl ester | MS: [M+H]$^+$=366.2; $^1$H NMR (CDCl$_3$/CD$_3$OH): δ 7.92(s, 1H), 7.76(s, 1H), 7.48(d, J=8.0Hz, 1H), 7.25(s, 1H), 7.05(d, J=8.0Hz, 1H), 3.82(s, 3H), 2.25(s, 3H) |

EXAMPLE 16

4-(2,3-Dihydro-2-oxo-1H-indol-3-yl)-5-methylpyrrolo[2,1-f][1,2,4]triazine-6-carb acid methyl ester

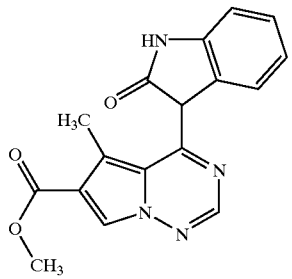

A solution of oxindole (5.32 g, 40 mmol) in THF (150 ml) and DMF (35 ml) was deoxygenated by purging with argon. This mixture was placed in an ice bath, and NaH (60% in oil, 1.7 g, 42 mmol) was added. After 30 min, 4-Chloro-5-methyl-6-carbomethoxypyrrolo[2,1-f][1,2,4]triazine (Compound E of Example 2) (3.38 g, 15 mmol) was added. After 1 hr at rt, the resulting mixture was neutralized with acetic acid. The solvent was removed in vacuo. The residue was dissolved in DCM, washed with brine, and dried (MgSO$_4$). The solution was concentrated to a solid residue which was triturated with DCM and diethyl ether to afford the title compound as an orange solid (3.5 g, 72%). MS: [M+H]$^+$=323.1; $^1$H NMR (CDCl$_3$): δ7.86 (s, 1H), 7.74 (s, 1H), 7.37 (s, 1H), 7.19 (d, J=7.6 Hz, 1H), 7.11 (t, J=7.6 Hz, 1H), 7.10 (t, J=7.6 Hz, 1H), 7.06 (d, J=7.6 Hz, 1H), 3.84 (s, 3H), 2.34 (s, 3H).

EXAMPLE 17

4-(2,3-Dihydro-3-oxo-1H-indazol-1-yl)-5-methylpyrrolo[2,1-f][1,2,4]triazine-6-ca acid methyl ester

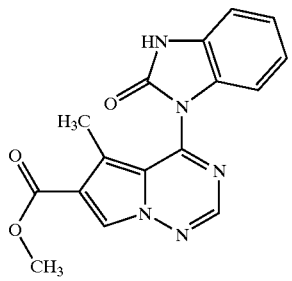

Example 17 above was prepared following the method of Example 16, except 3-indazolinone was used in place of oxindole. [M+H]$^+$=324; $^1$H NMR (CDCl$_3$): δ8.16 (s, 1H), 8.02–7.99 (m, 2H), 7.83–7.81 (m, 1H), 7.58–7.54 (m, 1H), 7.46 (s, 1H), 3.87 (s, 3H), 2.66 (s, 3H).

EXAMPLE 18

4-(2,3-Dihydro-1-methyl-2-oxo-1H-indol-3-yl)-5-methylpyrrolo[2,1-f][1,2,4]triazine-6-carboxylic acid methyl ester

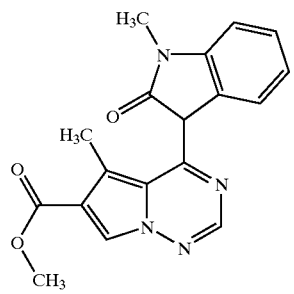

To a 0° C. mixture of NaH (60%, 5 mg, 0.106 mmol) in DMF (0.5 mL) was added N-methyloxindole (22 mg, 0.15 mmol). The reaction mixture was stirred for 10 min. at 0° C. Compound E of Example 2 (22 mg, 0.10 mmol) in DMF (1 mL) was added. The reaction mixture was stirred for 45 min. at 25° C. and then quenched with pH 7 phosphate buffer. The mixture was extracted with EtOAc. The combined extracts were dried (Na$_2$SO$_4$) and purified by preparative HPLC to provide Example 18 as a yellow solid. MS: [M+H]$^+$=337.2; $^1$H NMR (CDCl$_3$): δ7.90 (s, 1H), 7.40 (s, 1H), 7.16 (m, 2H), 7.02 (t, J=7.6 Hz, 1H), 6.90 (d, J=7.6 Hz, 1H), 5.28 (s, 1H), 3.86 (s, 3H), 3.36 (s, 3H), 2.37 (s, 3H).

EXAMPLES 19–24

(Ie)

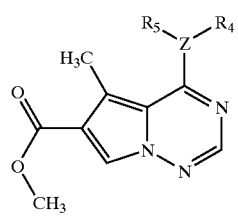

Compounds having the formula (Ie), wherein the groups Z, R$_4$, and R$_5$ together have the values listed in Table 3, were prepared following the method of Example 18, except instead of oxindole, an appropriately-substituted oxindole was used, and for Examples 19 and 20, 2,3-dihydro-2-oxo-1H-benzimidazol (40.2 mg, 0.3 mmol) and (methylsulfonyl)amino]-2-oxo-1H-indole (90 mg, 0.4 mmol) were used, respectively, in place of oxindole. After purification by preparative HPLC, the desired material can be collected, concentrated, and neutralized with aq. NaHCO$_3$ or desilylated with tetrabutylammonium fluoride.

TABLE 3

| Ex. | —ZR₄R₅ | Compound Name | Data |
|---|---|---|---|
| 19 | 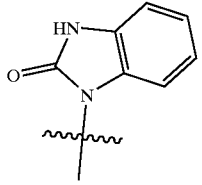 | 4-(2,3-Dihydro-2-oxo-1H-benzimidazol-1-yl)-5-methylpyrrolo[2,1-f][1,2,4]triazine-6-carboxylic acid methyl ester | $^1$H NMR (CDCl$_3$): δ 8.37 (s, 1H), 8.32(s, 1H), 7.95 (br, s, 1H), 7.21–7.10(m, 4H), 3.88(s, 3H), 2.51(s, 3H). |
| 20 | 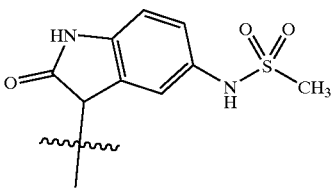 | 4-[2,3-Dihydro-5-[(methylsulfonyl)amino]-2-oxo-1H-indol-3-yl]-5-methylpyrrolo[2,1-f][1,2,4]triazine-6-carboxylic acid methyl ester | $^1$H NMR (CD$_3$OD): δ 7.99(s, 1H), 7.69(s, 1H), 7.04–7.02(m, 2H), 6.92 (d, J=8.8Hz, 1H), 3.86 (s, 3H), 2.87(s, 3H), 2.39 (s, 3H). |
| 21 | 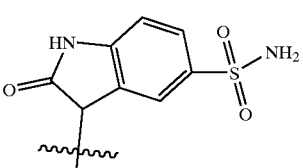 | 4-[5-(Aminosulfonyl)-2,3-dihydro-2-oxo-1H-indol-3-yl]-5-methylpyrrolo[2,1-f][1,2,4]triazine-6-carboxylic acid methyl ester | MS: [M−H]⁻=400.1; $^1$H NMR (CD$_3$OD): δ 8.05 (s, 1H), 7.83(s, 1H), 7.65 (d, J=8.2Hz, 1H), 7.07 (d, J=8.3Hz, 2H), 3.84 (s, 3H), 2.28(s, 3H). |
| 22 | 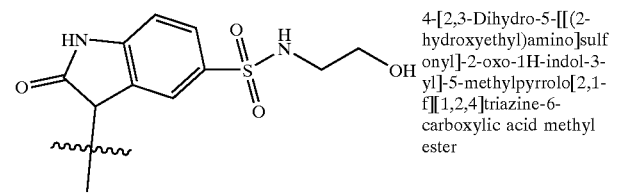 | 4-[2,3-Dihydro-5-[[(2-hydroxyethyl)amino]sulfonyl]-2-oxo-1H-indol-3-yl]-5-methylpyrrolo[2,1-f][1,2,4]triazine-6-carboxylic acid methyl ester | MS: [M+H]⁺=446.2; $^1$H NMR (CDCl$_3$/CD$_3$OH): δ 7.84(s, 1H), 7.55(s, 1H), 7.28(d, J=8.6Hz, 1H), 7.20(s, 1H), 6.78(d, J=8.6Hz, 1H), 3.78(s, 3H), 3.60(t, J=7.4Hz, 2H), 2.77(t, J=7.4Hz, 2H), 2.20(s, 3H). |
| 234 | 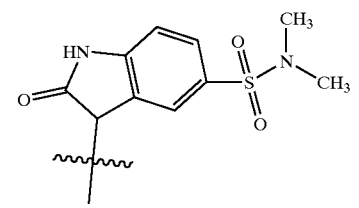 | 4-[5-[(Dimethylamino)sulfonyl]-2,3-dihydro-2-oxo-1H-indol-3-yl]-5-methylpyrrolo[2,1-f][1,2,4]triazine-6-carboxylic acid methyl ester | MS: [M+H]⁺=430. $^1$H NMR (CDCl$_3$): δ 9.56(s, 1H), 8.05(s, 1H), 7.65–7.54(m, 3H), 7.15(d, J=8.2Hz, 1H), 3.87(s, 3H), 2.73(s, 6H), 2.43 (3H, s) |
| 24 | 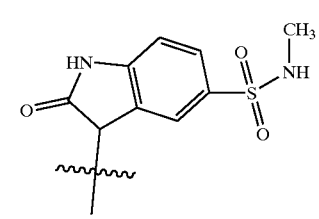 | 4-[2,3-Dihydro-5-[(methylamino)sulfonyl]-2-oxo-1H-indol-3-yl]-5-methylpyrrolo[2,1-f][1,2,4]triazine-6-carboxylic acid methyl ester | MS: [M−H]⁻=414. $^1$H NMR (CDCl$_3$/CD$_3$OH): δ 7.98(s, 1H), 7.76(s, 1H), 7.54(s, 1H), 7.31(d, J=7.6Hz, 1H), 6.85(d, J=7.6Hz, 1H), 3.82(s, 3H), 2.28(s, 3H), 2.21 (s, 3H). |

EXAMPLE 25

5-Methyl-4-(1,2,3,4-tetrahydro-3-oxo-1-quinoxalinyl)pyrrolo[2,1-f][1,2,4]triazine-6-carboxylic acid methyl ester

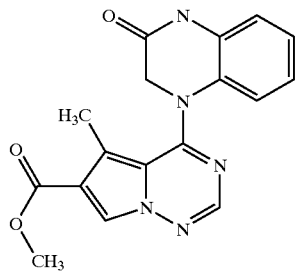

Example 2, Compound E (23 mg, 0.1 mmol) was stirred with 1,2,3,4-tetrahydroquinoxalin-2-one (44.4 mg, 0.3 mmol) in DMF (0.5 mL) for 1 hr at 50° C. Water was added, and the resulting solid material was collected, washed with water, and dried. The material was triturated with MeOH, filtered, and dried again to provide 20 mg (59%) of Example 25 as a white solid. $^1$H NMR (d-DMSO): δ8.30–8.25 (m, 2H), 7.12–7.03 (m, 2H), 6.83 (br s, 2H), 4.38 (s, 2H), 3.73 (s, 3H), 2.49 (s, 3H), 1.72 (s, 3H).

EXAMPLE 26

4-(2,3-Dihydro-2-oxo-1H-indol-3-yl)-5-methylpyrrolo[2,1-f][1,2,4]triazine-6-carboxylic acid

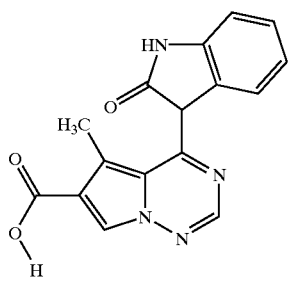

To a solution of Example 16 (3.3 g, 10.2 mmol) in MeOH (600 mL) was added KOH (1N aq. solution, 200 mL), and the mixture was deoxygenated by purging with argon. The reaction mixture was heated to 60° C. for 20 hrs, then cooled and concentrated to about 50 mL. The residue was acidified with concentrated HCl to pH 4. The yellow solid was collected, washed with water, and dried in vacuo to afford the title compound (2.9 g, 92%). MS: [M+H]$^+$=307.1; $^1$H NMR (CD$_3$OD): δ7.94 (s, 1H), 7.71 (s, 1H), 7.18–7.10 (m, 2H), 6.94–6.86 (m, 2H), 2.45 (s, 3H).

EXAMPLE 27

4-(2,3-Dihydro-2-oxo-1H-indol-3-yl)-5-methoxypyrrolo[2,1-f][1,2,4]triazine-6-carboxylic acid ethyl ester

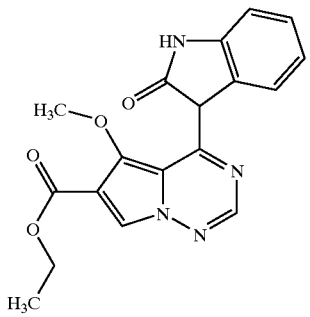

A. [[(2-Ethoxy-2-oxoethyl)(phenylmethyl)amino]methylene]propanedioic acid diethyl ester N-benzylglycine ethyl ester (5.79 g, 30 mmol) was combined with diethyl ethoxymethylene malonate (6.48 g, 30 mmol) and stirred at 120° C. for 1 hr. The crude material was used directly for the next reaction.

B. 1-Phenylmethyl-3-hydroxypyrrole-2,4-dicarboxylic acid diethyl ester

To a suspension of NaH (60% in oil, washed with hexanes, 500 mg, 12.5 mmol) in toluene (10 mL) was added Compound A (3.63 g, 10 mmol) in toluene (30 mL) dropwise at 50° C. After 2 hr, the mixture was poured into ice water and acidified with 1 N aq. HCl. The mixture was extracted three times with EtOAc. The combined organic extracts were dried (MgSO$_4$) and concentrated in vacuo. The crude material was purified by chromatography on silica gel eluting with 50% EtOAc in hexanes to provide 2.70 g (85%) of Compound B as a pink oil.

C. 1-Phenylmethyl-3-methoxypyrrole-2,4-dicarboxylic acid diethyl ester

Compound B (634 mg, 2 mmol) was stirred in acetone for 10 hrs at rt with methyl iodide (300 mg, 2.1 mmol) and K$_2$CO$_3$ (500 mg). The mixture was filtered, concentrated, and purified by chromatography on silica gel eluting with 33% EtOAc in hexanes to provide 470 mg (71%) of Compound C as a gel.

D. 3-methoxypyrrole-2,4-dicarboxylic acid diethyl

Compound C (27 g, 81.5 mmol) in EtOH (1 L) was mixed with Pd/C (10%, 4 g) and ammonium formate (28 g) and hydrogenated at 40 psi at 90° C. for 18 hrs. The reaction mixture was cooled to rt, filtered, and concentrated. The crude material (brown oil) was purified by chromatography on silica gel eluting with 25% EtOAc in hexanes to provide 13 g (66%) of tan solid.

E. 1-Amino-3-methoxypyrrole-2,4-dicarboxylic acid diethyl ester

To a stirred suspension of NaH (60% in oil, 1.76 g, 70 mmol) in DMF (350 mL) under nitrogen at 0° C. was added dropwise a solution of Compound D (13 g, 54 mmol) in DMF (200 mL). After 30 min, the mixture was diluted with DMF (750 mL), and then diphenyl phosphoryl hydroxylamine (15.7 g, 67.4 mmol) was added and the reaction mixture was allowed to warm to rt. After 6 hrs, the mixture was concentrated and the residue diluted with water (1 L) and extracted with EtOAc (3×1 L). The combined organic extracts were dried (MgSO$_4$), concentrated, and purified by chromatography on silica gel eluting with 20% EtOAc in hexanes to provide 13 g (93%) of solid.

F. 4-Hydroxy-5-methoxypyrrolo[2,1-f][1,2,4]triazine-6-carboxylic acid ethyl ester Compound E (100 mg, 0.39 mmol) was combined with formamide (1 mL) and heated at 180° C. for 6 hrs. The reaction mixture was cooled to rt and diluted with water (5 mL). The solid which formed was collected, washed with water, and dried to provide 70 mg (76%) of Compound F.

G. 4-Chloro-5-methoxypyrrolo[2,1-f][1,2,4]triazine-6-carboxylic acid ethyl ester

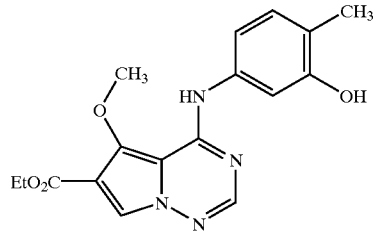

Phosphorous oxychloride (1 mL) was combined with Compound F (23.7 mg, 0.1 mmol) and heated at reflux for 2 hrs. The melt was allowed to cool to rt and phosphorous oxychloride was removed on rotary evaporator.

H. Example 27

To a suspension of NaH (60%, 44 mg, 1.1 mmol) in THF (1 mL) was added oxindole (133 mg, 1 mmol). The reaction mixture was stirred for 20 min. at rt and Compound G (0.1 mmol) was added. The reaction was stirred for 2 hrs at 25° C. The crude material was purified by preparative HPLC followed by chromatography on silica gel eluting with EtOAc to provide 5.5 mg (16%) of Example 27 as a yellow solid. MS: [M+H]$^+$=353; $^1$H NMR (CDCl$_3$): δ8.42 (s, 0.4H), 8.10 (s, 0.6H), 7.79 (s, 1H), 7.75–6.88 (m, 4H), 4.33 (m, 2H), 3.57 (s, 3H), 1.37 (m, 3H).

EXAMPLE 28

5-Methyl-4-[[4-methyl-3-[(methylsulfonyl)amino]phenyl]amino]pyrrolo[2,1-f][1,2,4]triazine-6-carboxylic acid methyl ester

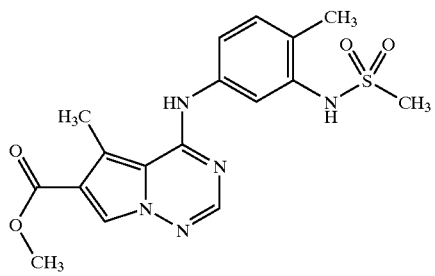

To a solution of Example 6 (16 mg, 51 μmol) in pyridine (1 mL) at 0° C. was added 4-methyl-3-[(methylsulfonyl)aniline (4.4 μL, 87 μmol). The reaction mixture was stirred for 1 hr at 0° C. and then warmed to 25° C. and stirred for 4 hrs. Water (5 mL) was added and the mixture was extracted with EtOAc (3×5 mL). The combined organic extracts were washed with water (10 mL) and brine (10 mL) and dried (Na$_2$SO$_4$). The crude material was purified by chromatography on silica gel eluting with 2% MeOH in chloroform to provide 6.9 mg (30%) of solid. MS: [M+H]$^+$=390.2; $^1$H NMR (CDCl$_3$): δ7.93 (s, 1H), 7.86 (s, 1H), 7.77 (s, 1H), 7.35 (d, J=8.2 Hz, 1H), 7.27 (s, 1H), 7.18 (d, J=8.2 Hz, 1H), 6.25 (s, 1H), 3.82 (s, 3H), 3.03 (s, 3H), 2.86 (s, 3H), 2.24 (s, 3H)

EXAMPLE 29

[4-(2,3-Dihydro-2-oxo-1H-indol-3-yl)-5-methylpyrrolo[2,1-f][1,2,4]triazin-6-yl]carbamic acid phenylmethyl ester

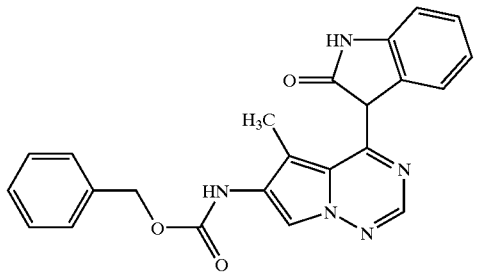

To a solution of Example 26 (29 mg, 0.09 mmol) in 1,4-dioxane (0.6 mL) under Ar with powdered 4 Å molecular sieves was added TEA (10 μL, 71 μmol), diphenylphosphoryl azide (15 μL, 71 μmol) and benzyl alcohol (12 μL, 0.12 mmol). The reaction was warmed at 50° C. for 15 hrs. The mixture was concentrated in vacuo and chromatographed directly on silica gel eluting with a gradient of 2–5% MeOH in chloroform to provide 8 mg (50%) of an intermediate product as a white solid. Phosphorous oxybromide (5 eq.) was combined with this intermediate (16 mg, 0.054 mmol) and heated to 60° C. for 20 min. The melt was poured into ice water and extracted with EtOAc (4×5 mL). The extracts were washed with aq. NaHCO$_3$, dried (Na$_2$SO$_4$), and concentrated in vacuo. The residue was dissolved in a mixture of CH$_3$CN (0.5 mL) and DMF (0.1 mL), and then 5-amino-o-cresol (10 mg, 0.081 mmol) was added. The reaction mixture was stirred overnight under argon at 25° C. Solvent was removed in vacuo, and the crude material was purified by rotary chromatography on a 1 mm silica gel plate eluting with 2% MeOH in chloroform to afford the title compound as yellow oil (5 mg, 13%). MS: [M+H]$^+$=414; $^1$H NMR (CDCl$_3$): δ7.94 (s, 1H), 7.82 (s, 1H), 7.41–7.34 (m, 5H), 7.17–7.14 (m, 1H), 7.04–7.02 (m, 1H), 6.93–6.90 (m, 2H), 6.44 (s, 1H), 5.23 (s, 2H), 2.12 (s, 3H).

EXAMPLE 30

4-(2,3-Dihydro-6-methyl-2-oxo-1H-pyrazolo[2,3-d]pyrimidin-3-yl)-5-methylpyrrolo[2,1-f][1,2,4]triazine-6-carboxylic acid methyl ester

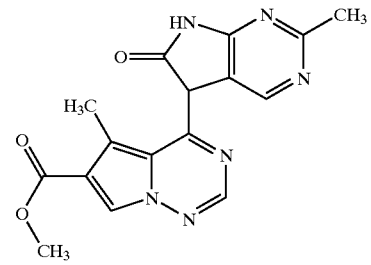

A. 6-Methyl-5,7-diazaoxindole

To a solution of ethyl (4-amino-2-methylpyrimidin-5-yl)acetate (WO 99/10349, 0.975 g, 5 mmol) in THF (30 ml), was slowly added potassium t-butoxide (1 M in THF, 5 mL). After one hour, the mixture was neutralized with acetic acid to pH 5. The volatiles were removed in vacuo and the residue purified by flash column chromatography (silica gel, 5–8% MeOH in DCM) to afford a yellow solid (680 mg, 91%).

49

B. Methylpyrrolo[2,1-f][1,2,4]triazine-6-carboxylic acid methyl ester

To a solution of 6-methyl-5,7-diazaoxindole (67 mg, 0.45 mmol) in DMF (2 ml) and THF (1 ml) was added NaH (60% in oil, 20 mg, 0.5 mmol). After stirring for 20 min, Compound E of Example 2 (34 mg, 0.15 mmol) was added. The mixture was stirred at rt overnight and then neutralized with acetic acid. DCM (10 ml) was added and the resulting precipitate was collected and washed with small amounts of DCM and water and then dried in vacuo to give the title compound as an orange solid (32 mg,63%). MS: (M+H)= 359

EXAMPLE 31

4-(2,3-Dihydro-2-oxo-1H-pyrazolo[2,3-b]pyridin-3-yl)-5-methylpyrrolo[2,1-f][1,2,4]triazine-6-carboxylic acid methyl ester

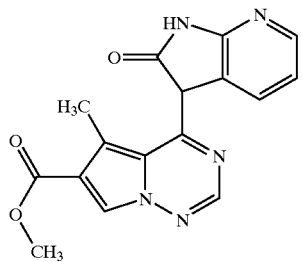

To a solution of 7-azaoxindole (see *Tetrahedron.Lett.*, Vol. 28 (1987), at p. 4027) (60 mg, 0.45 mmol) in DMF (2 mL) and THF (1 mL) was added NaH (60% in oil, 20 mg, 0.5 mmol). After stirring for 20 min, Compound E of Example 2 (34 mg, 0.15 mmol) was added, and the mixture was stirred at rt overnight. The solution was neutralized with acetic acid, and then DCM (10 ml) was added to the mixture. The resulting solid was collected, washed with small amounts of DCM and water and dried in vacuo to give a yellow solid (35 mg, 72%). LC-MS: (M+H)$^+$=324.

EXAMPLE 32

4-(2,3-Dihydro-2-oxo-1H-indol-3-yl)pyrrolo[2,1-f][1,2,4]triazine-6-carboxylic acid methyl ester

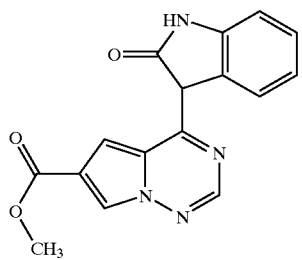

Example 2 was following using 2-methoxycarbonyl pyrrole as the starting pyrrole to afford 4-chloro-6-carbomethoxypyrrolo[2-f][1,2,4]triazine, which was then converted to Example 32 using the same or similar procedure of Example 31.

50

EXAMPLES 33–36

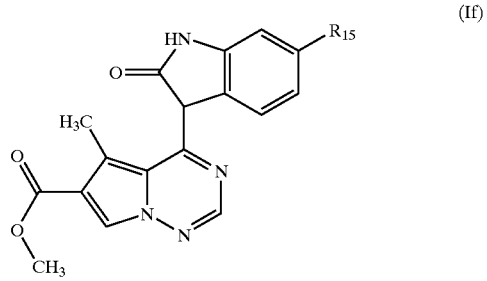

(If)

Compounds having the formula (If), wherein $R_{15}$ has the values listed in Table prepared by following the procedure of Example 32 using appropriate reagents in the literature (see, WO 97/42187).

TABLE 4

| Ex. | $R_{15}$ | Compound name |
|---|---|---|
| 33 | F | 4-[6-Fluoro-2-hydroxy-1H-indol-3-yl]-5-methylpyrrolo[2,1-f][1,2,4]triazine-6-carboxylic acid methyl ester |
| 34 | Br | 4-[6-Bromo-2-hydroxy-1H-indol-3-yl]-5-methylpyrrolo[2,1-f][1,2,4]triazine-6-carboxylic acid methyl ester |
| 35 | CF$_3$ | 4-[2,3-Dihydro-2-oxo-6-(trifluoromethyl)-1H-indol-3-yl]-5-methylpyrrolo[2,1-f][1,2,4]triazine-6-carboxylic acid methyl ester |
| 36 | SO$_2$Me | 4-[2,3-Dihydro-6-(methylsulfonyl)-2-oxo-1H-indol-3-yl]-5-methylpyrrolo[2,1-f][1,2,4]triazine-6-carboxylic acid methyl ester |

EXAMPLES 37–49

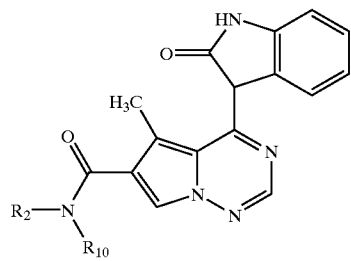

(Ig)

To Example 26 (50 mg, 0.16 mmol) in DMF (1 mL) and DCM (0.5 mL) were added PyBrop (113 mg, 0.24 mmol) and DIPEA (0.08 mL, 0.5 mL). After 10 min, an appropriate amine was added. After 15 h, the reaction mixture was purified by preparative RP HPLC to provide the compounds of formula (Ig), above, wherein $R_2$ and $R_{10}$ have the values listed in Table 5.

TABLE 5

| EX. | R₂ | R₁₀ | Compound Name |
|---|---|---|---|
| 37 | pyrrolidinyl-ethyl | CH₃ | 4-(2,3-Dihydro-2-oxo-1H-indol-3-yl)-N,5-dimethyl-N-[2-(1-pyrrolidinyl)ethyl]pyrrolo[2,1-f][1,2,4]triazine-6-carboxamide |
| 38 | pyrrolidinyl-ethyl | H | 4-(2,3-Dihydro-2-oxo-1H-indol-3-yl)-5-methyl-N-[2-(1-pyrrolidinyl)ethyl]pyrrolo[2,1-f][1,2,4]triazine-6-carboxamide |
| 39 | morpholinyl-propyl | H | 4-(2,3-Dihydro-2-oxo-1H-indol-3-yl)-5-methyl-N-[3-(4-morpholinyl)propyl]pyrrolo[2,1-f][1,2,4]triazine-6-carboxamide |
| 40 | morpholinyl-ethyl | H | 4-(2,3-Dihydro-2-oxo-1H-indol-3-yl)-5-methyl-N-[2-(4-morpholinyl)ethyl]pyrrolo[2,1-f][1,2,4]triazine-6-carboxamide |
| 41 | 4-methylpiperazinyl-propyl | H | 4-(2,3-Dihydro-2-oxo-1H-indol-3-yl)-5-methyl-N-[3-(4-methyl-1-piperazinyl)propyl]pyrrolo[2,1-f][1,2,4]triazine-6-carboxamide |
| 42 | 1,2,3-triazol-1-yl-propyl | H | 4-(2,3-Dihydro-2-oxo-1H-indol-3-yl)-5-methyl-N-[3-(1H-1,2,3-triazol-1-yl)propyl]pyrrolo[2,1-f][1,2,4]triazine-6-carboxamide |
| 43 | 1,2,3-triazol-2-yl-propyl | H | 4-(2,3-Dihydro-2-oxo-1H-indol-3-yl)-5-methyl-N-[3-(2H-1,2,3-triazol-2-yl)propyl]pyrrolo[2,1-f][1,2,4]triazine-6-carboxamide |
| 44 | 1,2,4-triazol-1-yl-propyl | H | 4-(2,3-Dihydro-2-oxo-1H-indol-3-yl)-5-methyl-N-[3-(1H-1,2,4-triazol-1-yl)propyl]pyrrolo[2,1-f][1,2,4]triazine-6-carboxamide |
| 45 | 2-methylimidazol-1-yl-propyl | H | 4-(2,3-Dihydro-2-oxo-1H-indol-3-yl)-5-methyl-N-[3-(2-methyl-1H-imidazol-1-yl)propyl]pyrrolo[2,1-f][1,2,4]triazine-6-carboxamide |
| 46 | morpholinyl-butyl | H | 4-(2,3-Dihydro-2-oxo-1H-indol-3-yl)-5-methyl-N-[4-(4-morpholinyl)butyl]pyrrolo[2,1-f][1,2,4]triazine-6-carboxamide |
| 47 | morpholinyl-propyl | CH₃ | 4-(2,3-Dihydro-2-oxo-1H-indol-3-yl)-N,5-dimethyl-N-[3-(4-morpholinyl)propyl]pyrrolo[2,1-f][1,2,4]triazine-6-carboxamide |
| 48 | H | H | 4-(2,3-Dihydro-2-oxo-1H-indol-3-yl)-5-methylpyrrolo[2,1-f][1,2,4]triazine-6-carboxamide |
| 49 | H | CH₃ | 4-(2,3-Dihydro-2-oxo-1H-indol-3-yl)-N,5-dimethylpyrrolo[2,1-f][1,2,4]triazine-6-carboxamide |

EXAMPLES 50–52

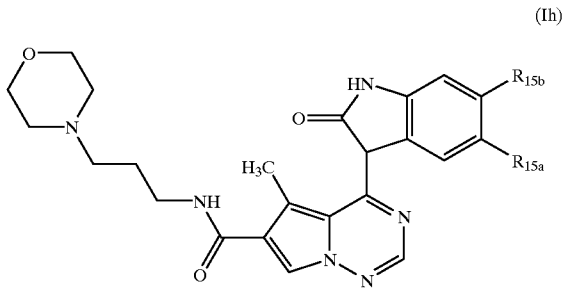

(Ih)

Compounds having formula (Ih), wherein $R_{15a}$ and $R_{15b}$ have the values listed in Table 6 below, were prepared by the following process, using the appropriately substituted oxindole in step C.

A. 5-Methylpyrrolo[2,1-f][1,2,4]triazin-4(3H)-one-6-carboxylic acid

To a solution of 5-Methylpyrrolo[2,1-[1,2,4]triazin-4 (3H)-one-6-carboxylic acid methyl ester (Compound D from Example 2, 1.035 g, 5.00 mmol) in a mixture of THF/MeOH/water (50 mL, 3:1:1) was added lithium hydroxide (2.062 g, 49.1 mmol). The reaction mixture was stirred at 55° C. for 12 h, then cooled to 0° C. and neutralized by 3N HCl. The organic solvents were removed and the aqueous solution brought to pH 4 with 1 N HCl. The resulting precipitate was filtered, rinsed with cold water, and air dried to afford Compound A as an off-white solid (0.965 g, 100%).

B. 4-Chloro-5-methyl-N-[3-(4-morpholinyl)propyl]pyrrolo [2,1-f][1,2,4]triazine-6-carboxamide A suspension of Compound A (2.00 g, 10.4 mmol) in phosphorous oxychloride (8 mL) was stirred at 100° C. over 4 h. The solvent was removed in vacuo using toluene to assist in the removal. The resulting green solid was suspended in acetonitrile (20 mL) at 0° C. and treated with sufficient TEA (5 mL) to bring the solution to pH 10.4-(3-aminopropyl)morpholine (1.5 mL, 10.3 mmol) was added, and the solution was allowed to stir at rt over 1 h. The reaction mixture was poured into saturated sodium bicarbonate solution and extracted with EtOAc. The organic layer was dried (MgSO$_4$) and the volatiles were removed in vacuo to afford Compound B as a yellow solid (1.75 g, 50%).

C. EXAMPLES 50–52

To a solution of an appropriately substituted oxindole, i.e., 5-fluoro oxindole for Example 50 (36 mg, 0.24 mmol) in DMF (1 mL) was added NaH (5.9 mg, 0.23 mmol). After 30 min at rt, a solution of Compound B (24 mg, 0.072 mmol) in DMF (1 mL) was added and the resulting mixture was stirred at rt over 1 h. The solvent was removed in vacuo and the mixture purified by RP HPLC. MeOH in the desired HPLC fractions was removed in vacuo and the resulting aq. solution neutralized using sat'd sodium bicarbonate solution, then extracted with EtOAc. The organic layer was dried (MgSO$_4$) and the volatiles were removed in vacuo. The solid obtained was dissolved in acetonitrile/MeOH and treated with 1 N HCl in diethyl ether. The mixture was stirred at rt over 1 h and the solvents removed in vacuo. The HCl salt of the title compound was obtained as an orange solid (18 mg, 51%).

TABLE 6

| Ex. | $R_{15a}$ | $R_{15b}$ | Compound Name | Data |
|---|---|---|---|---|
| 50 | F | H | 4-(5-Fluoro-2,3-dihydro-2-oxo-1H-indol-3-yl)-5-methyl-N-[3-(4-morpholinyl)propyl]-pyrrolo[2,1-f][1,2,4]triazine-6-carboxamide | MS: (M+H)$^+$= 453. |
| 51 | H | F | 4-(6-Fluoro-2,3-dihydro-2-oxo-1H-indol-3-yl)-5-methyl-N-[3-(4-morpholinyl)propyl]-pyrrolo[2,1-f][1,2,4]triazine-6-carboxamide; | — |
| 52 | —SO$_2$NH$_2$ | H | 4-[5-(Aminosulfonyl)-2,3-dihydro-2-oxo-1H-indol-3-yl]-5-methyl-N-[3-(4-morpholinyl)propyl]-pyrrolo[2,1-f][1,2,4]triazine-6-carboxamide | — |

EXAMPLE 53

4-(2,3-Dihydro-2-oxo-1H-indol-3-yl)-5-methylpyrrolo[2,1-f][1,2,4]triazine-6-propanoic acid methyl ester

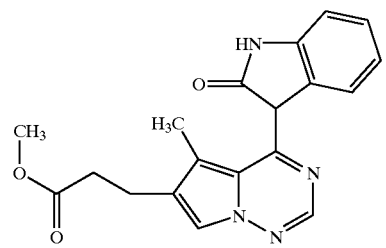

A. 4-Phenoxy-5-methyl-6-carbomethoxypyrrolo[2,1-f][1,2,4]triazine

To a solution of phenol (705 mg, 7.5 mmol) in a mixture of THF (10 mL) and DMF (10 mL) was added NaH (60% in oil, 300 mg, 7.5 mmol). After 30 min, 4-chloro-5-methyl-6-carbomethoxypyrrolo[2,1-f][1,2,4]triazine (675 mg, 3.0 mmol—Compound E from Example 2) was added. After 1 h, the solvent was removed and the residue poured into 5% aq. K$_2$CO$_3$ solution. The precipitate was collected, washed with water, and dried in vacuo to afford Compound A as white solid (800 mg, 94%). MS: (M+H)$^+$=284.

B. 4-Phenoxy-5-methyl-6-hydroxymethylpyrrolo[2,1-f][1,2,4]triazine

To a solution of Compound A (700 mg, 2.47 mmol) in toluene (20 mL) at −60° C., was added DIBAL (1.5 M in toluene, 6 mmol). After stirring at 0° C. for 1 h, aq. 1N HCl (30 mL) was added and the mixture stirred for 30 min. The mixture was then diluted with DCM. The organic layer was separated, dried (MgSO$_4$), and concentrated. The residue was purified by flash column chromatography (silica gel, 2% MeOH in DCM) to afford Compound B as a solid (610 mg, 96%). MS: (M+H)$^+$=256.

C. 4-Phenoxy-5-methylpyrrolo[2,1-f][1,2,4]triazine-6-carboxaldehyde

A mixture of Compound B (500 mg, 1.96 mmol) and MnO$_2$ (3.0 g) in toluene (30 mL) was heated at 60° C. for 1 h. After cooling to rt, the mixture was filtered through a pad of silica gel and washed with EtOAc. After concentration in vacuo, Compound C was obtained as a white solid (420 mg, 85%). MS: (M+H)$^+$=254

D. 4-Phenoxy-5-methylpyrrolo[2,1-f][1,2,4]triazine-6-propenoic acid methyl ester DBU (1.42 mL, 9.49 mmol) was added to a solution of Compound C (600 mg, 2.37 mmol) and methyl diethylphosphonoacetate (1.74 mL, 9.49 mmol) in DCE (20 mL). After stirring at rt overnight, the reaction mixture was diluted with DCM and washed with aq. 2% citric acid, brine, dried (MgSO$_4$), and concentrated. The organic extract was concentrated and the residue purified by chromatography on silica gel and elution with 20% EtOAc/DCM to afford a white solid (710 mg, 97%). MS: (M+H)$^+$=310.

E. 4-Hydroxy-5-methylpyrrolo[2,1-f][1,2,4]triazine-6-propanoic acid methyl ester Pd/C (10%, 70 mg) was added to a solution of Compound D (710 mg, 2.30 mmol) in a solvent mixture EtOAc/MeOH/THF/AcOH (100 mL/100 mL/20 mL/2 mL). The suspension was stirred under hydrogen for 2 h. The reaction mixture was passed through Celite, the Celite was washed with MeOH, and the filtrate was concentrated in vacuo to give crude product. Trituration with hexanes afforded Compound E as a white solid (430 mg, 88%). MS:(M+H)$^+$=236.

F. 4-Chloro-5-methylpyrrolo[2,1-f][1,2,4]triazine-6-propanoic acid methyl ester

A mixture of DIPEA (0.24 mL, 1.4 mmol), Compound E (220 mg, 0.94 mmol) and POCl$_3$ (3 mL) was heated in a sealed bottle at 80° C. After 2 h, the mixture was cooled down to rt and concentrated in vacuo to give a residue. The residue was partitioned between DCM and aq. NaHCO$_3$ solution. The DCM layer was separated, dried (MgSO$_4$), and concentrated in vacuo to give a dark green solid. Purification by chromatography on silica gel and elution with 20% EtOAc/DCM afforded Compound F as a yellow solid (220 mg, 92%). MS: (M+H)$^+$=254.

G. 4-(2,3-Dihydro-2-oxo-1H-indol-3-yl)-5-methylpyrrolo[2,1-f][1,2,4]triazine-6-propanoic acid methyl ester NaH (60% in oil, 28 mg, 0.71 mmol) was added to a solution of oxindole (94 mg, 0.71 mmol) in DMF (2 mL) under argon. The mixture was stirred for 10 min. and Compound F (60 mg, 0.24 mmol) was added. After 1 h at RT, the reaction was quenched by the addition of acetic acid and diluted with DCM. The organic solution was washed with water, dried (MgSO$_4$), and concentrated in vacuo to give crude product. Purification by chromatography on silica gel and elution with 20% EtOAc/DCM afforded the title compound as a pure yellow solid (78 mg, 94%). MS: (M+H)$^+$=351.

EXAMPLE 54

1,3-Dihydro-3-[5-methoxy-6-(phenylmethoxy)pyrrolo[2,1-f][1,2,4]triazin-4-yl]-2H-indol-2-one

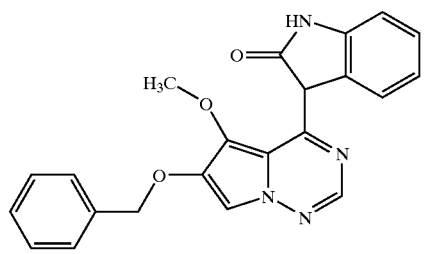

A. 4-Hydroxy-5-methoxypyrrolo[2,1-f][1,2,4]triazine-6-methanol

4-Hydroxy-5-methoxypyrrolo[2, 1-f][1,2,4]triazine-6-carboxylic acid ethyl ester (Compound F of Example 27–3.56 g, 15 mmol) was combined with lithium tri-tert-butoxyaluminohydride (1 M solution in THF, 60 mL, 60 mmol) and heated at reflux overnight. The reaction mixture was allowed to cool to rt and quenched with 1 N aq. HCl. The mixture was concentrated to remove volatiles and the remaining material was combined with 100 g of silica gel and applied to a flash silica gel column which was eluted with EtOAc to provide 2.65 g (90%) of Compound A. MS: [M+H]$^+$=196.

B. 2,2-Dimethylpropanoic acid [6-(hydroxymethyl)-5-methoxy-4-oxopyrrolo[2,1-f][1,2,4]triazin-3(4H)-yl]methyl ester Compound A (195 mg, 1 mmol) was dissolved in 1.5 mL of DMF. NaH (60% in oil, 48 mg, 1.2 mmol) was added and the reaction mixture was stirred at rt for 0.5 hr. Chloromethyl pivalate (181 mg, 1.2 mmol) was added and the mixture was stirred for 1 hr. Water was added and the mixture was extracted with EtOAc (3×10 mL). The combined extracts were dried (Na$_2$SO$_4$), concentrated in vacuo and purified by flash column chromatography on silica gel eluting with 33% EtOAc in hexanes to provide 260 mg (84%) of Compound B as a solid. MS: [M+H]$^+$=310.

C. 2,2-Dimethylpropanoic acid [6-formyl-5-methoxy-4-oxopyrrolo[2,1-f][1,2,4]triazin-3(4H)-yl]methyl ester Compound B (740 mg, 2.39 mmol) was suspended in toluene (10 mL) with manganese dioxide (835 mg, 9.6 mmol) and heated at 100° C. for 3 hr. The reaction mixture was cooled to rt, filtered, and the precipitate was washed with EtOAc. The filtrate was concentrated in vacuo to provide 660 mg (90%) of Compound C as a solid. MS: [M+H]$^+$=308.

D. 2,2-Dimethylpropanoic acid [6-formyloxy-5-methoxy-4-oxopyrrolo[2,1-f][1,2,4]triazin-3(4H)-yl]methyl ester

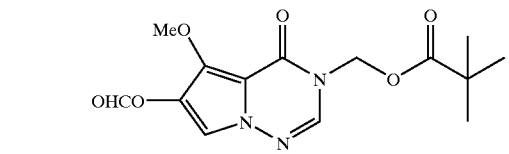

Compound C (660 mg, 2.15 mmol) was dissolved in CH$_2$Cl$_2$ (10 mL). M-chloroperoxybenzoic acid (57%, 745 mg, 2.46 mmol) was added with MgSO$_4$ (2.0 g), and the reaction mixture was stirred at rt for 5 hr. The mixture was filtered and the filtrate washed with aq. NaHCO$_3$ solution twice, dried (MgSO$_4$), and concentrated to provide 680 mg (98%) of Compound D as a solid. MS: [M+H]$^+$=324.

E. 2,2-Dimethylpropanoic acid [5-methoxy-4-oxo-6-(phenylmethoxy)pyrrolo[2,1-f][1,2,4]triazin-3(4H)-yl]methyl ester Compound D (680 mg, 2.10 mmol, 1 eq) was dissolved in acetone (10 mL) followed by the addition of benzyl bromide (430 mg, 2.5 mmol) and K$_2$CO$_3$ (1.0 g, 7.25 mmol). The reaction mixture was stirred at 60° C. for 10 hr, cooled to rt, and filtered. The filtrate was concentrated and purified by flash silica gel chromatography eluting with 25% EtOAc in hexanes to provide 485 mg (60%) of Compound E as a gel. MS: [M+H]$^+$=386;

F. 5-Methoxy-6-(phenylmethoxy)pyrrolo[2,1-f][1,2,4]triazin-4(3H)-one

Compound E (65 mg, 0.17 mmol) was stirred at rt in a mixture of MeOH (1 mL) and ammonium hydroxide (0.2 mL) for 6 hrs. The mixture was concentrated in vacuo, dissolved in CH$_2$Cl$_2$, and purified by flash silica gel chromatography eluting with 33% EtOAc in hexanes to provide 45 mg (97%) of compound F as a solid. MS: [M+H]$^+$=272.

G. 4-Chloro-5-methoxy-6-(phenylmethoxy)pyrrolo[2,1-f][1,2,4]triazine

Compound F (44 mg, 0.16 mmol) was stirred with POCl$_3$ (0.5 mL) at 60° C. for 3 hr. The mixture was concentrated in vacuo, dissolved in CH$_2$Cl$_2$ (2 mL), and stirred with solid NaHCO$_3$ for 10 min. The mixture was filtered and concentrated to provide 46 mg (99%) of Compound G as a solid. MS: [M+H]$^+$=286. (The Cl substituent may be replaced with OCH$_3$ upon standing in MeOH); R.T.=3.265 min (YMC S5 ODS column 4.6×50 mm, 10–90% aq. MeOH over 4 minutes containing 0.2% phosphoric acid, 4 mL/min, monitoring at 220 nm); $^1$H NMR (CDCl$_3$): δ8.01 (s, 1H), 7.45–7.30 (m, 6 H), 5.15 (s, 2H), 4.03 (s, 3H).

H. 1,3-Dihydro-3-[5-methoxy-6-(phenylmethoxy)pyrrolo[2,1-f][1,2,4]triazin-4-yl]-2H-indol-2-one To a suspension of NaH (60% in oil, 19.2 mg, 0.48 mmol) in DMF (0.5 mL) was added oxindole (63.4 mg, 0.48 mmol). The reaction mixture was stirred for 1 hr at RT. Compound G (38 mg, 0.16 mmol, 1 eq) was added, and the mixture was stirred for 1 hr. The mixture was diluted with water and filtered. The resulting solid was triturated with MeOH and dried to provide 38 mg (62%) of the titled compound. MS: [M+H]$^+$=387; $^1$H NMR (d-DMSO): δ12.83 (br s, 1H), 10.64 (br s, 1H), 7.78 (s, 1H), 7.60 (s, 1H), 7.50–7.31 (m, 6H), 7.02–6.94 (m, 1H), 6.89–6.82 (m, 2H), 5.10 (s, 2H), 3.55 (s, 3H).

EXAMPLES 55–60

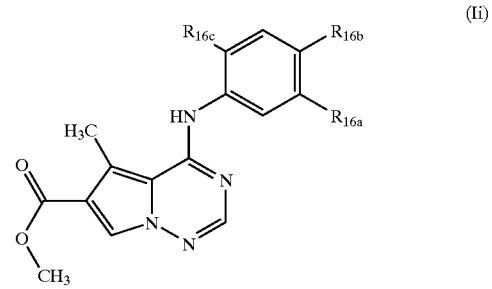

(Ii)

Compounds having the formula (Ii), wherein $R_{16a}$, $R_{16b}$, and $R_{16c}$ have the values listed in Table 7, below, were prepared following the procedure described for Example 54, except using a different phenylamine.

TABLE 7

| Ex | $R_{16a}$ | $R_{16b}$ | $R_{16c}$ | Compound Name | Data |
|---|---|---|---|---|---|
| 55 | F | H | CH$_3$ | 4-[(5-Fluoro-2-methylphenyl)amino]-5-methylpyrrolo[2,1-f][1,2,4]triazine-6-carboxylic acid methyl ester | [M+H]$^+$=315.2; $^1$H NMR (CDCl3) δ 7.97(br s, 1H), 7.94 (s, 1H), 7.88(s, 1H), 7.13(t, J=8.2Hz, 1H), 6.77(dt, J=2.7, 8.3Hz, 1H), 3.87(s, 3H), 2.82(s, 3H), 2.27(s, 3H) |
| 56 | ![structure] | H | CH$_3$ | 4-[[5-[(Ethylamino)carbonyl]-2-methylphenyl]amino]-5-methylpyrrolo[2,1-f][1,2,4]triazine-6-carboxylic acid methyl ester | [M+H]$^+$=368.23; $^1$H NMR (CDCl3) δ 8.17(br s, 1H), 7.92 (s, 1H), 7.83(s, 1H), 7.46(d, J=7.8Hz, 1H), 7.23(d, J=7.7 Hz, 1H), 3.82(s, 3H), 3.40(M, 2H), 2.88(s, 3H), 2.30(s, 3H), 1.85(m, 3H). |
| 57 | H | F | CH$_3$ | 4-[(4-Fluoro-2-methylphenyl)amino]-5-methylpyrrolo[2,1-f][1,2,4]triazine-6-carboxylic acid methyl ester | [M+H]$^+$=315.1; $^1$H NMR (CDCl3) δ 7.99(s, 1H), 7.87(s, 1H), 7.68(br s, 1H), 6.99(m, 2H), 3.88 (s, 3H), 2.85(s, 3H), 2.31(s, 3H). |
| 58 | H | F | H | 4-[(4-Fluorophenyl)amino]-5-methylpyrrolo[2,1-f][1,2,4]triazine-6-carboxylic acid methyl ester | [M+H]$^+$=301.1; $^1$H NMR (CDCl3) δ 7.94(s, 1H), 7.85(s, 1H), 7.54(m, 2H), 7.05(t, J=8.8Hz, 2H), 3.82(s, 3H), 2.82(s, 3H). |
| 59 | ![structure] | H | CH$_3$ | 4-[[5-[[(3-Methoxyphenyl)amino]carbonyl]-2-methylphenyl]amino]-5-methylpyrrolo[2,1-f][1,2,4]triazine-6-carboxylic acid methyl ester | [M+H]$^+$=446.2. |

TABLE 7-continued

| Ex | R$_{16a}$ | R$_{16b}$ | R$_{16c}$ | Compound Name | Data |
|---|---|---|---|---|---|
| 60 | 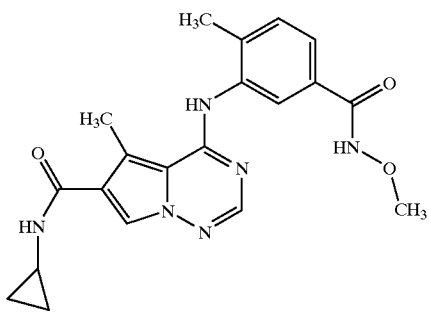 | H | CH$_3$ | 5-Methyl-4-[2-methyl-5-[(methylamino)carbonyl]phenoxy]pyrrolo[2,1-f][1,2,4]triazine-6-carboxylic acid methyl ester | [M+H]$^+$=355.1. |

EXAMPLE 61

N-Cyclobutyl-4-[[5-[(methoxyamino)carbonyl]-2-methylphenyl]amino]-5-methylpyrrolo[2,1-f][1,2,4]triazine-6-carboxamide

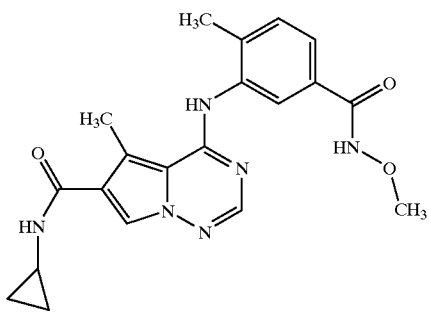

The compound of Example 61 was prepared as set forth below, using the Scheme 9 described above, wherein Compounds (A)–(E) have the structures indicated below.

A.

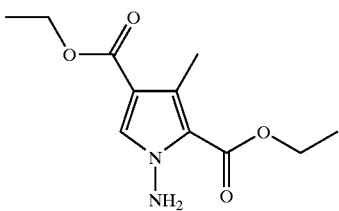

To a solution of the 3-methyl-1-pyrrole-2,4-diethyl ester (100 mg) (*J. Heterocyclic Chem* Vol. 34 (1997), at pp. 177–193; *Heterocycles*, Vol. 50 (1999), at pp. 853–866; *Synthesis* (1999), at pp. 479–482) in DMF (0.44M) was added either NaH or KOtBu (1.2 equiv) at rt. This solution was stirred for 30–45 minutes. Chloramine in ether (ca. 0.15M, 1 eq.) was added via syringe. The solution was stirred for 1.5 h or until starting material was converted to product as judged by HPLC analysis. The reaction was then quenched with aq. Na$_2$S$_2$O$_3$ and extracted with EtOAc or Et$_2$O. The organic extracts were washed with water and brine and then dried over sodium sulfate. Compound A was obtained in >90% yield. NH$_2$Cl in ether was prepared according to the procedure of Nunn, *J. Chem. Soc. (C)*, (1971) at p. 823.

B.

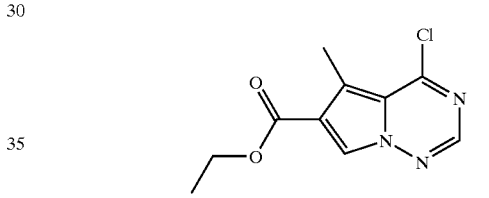

To a solution of Compound A (2 g) in formamide (8 mL) was added acetic acid (20% by weight), and the mixture was heated at 120° C. for 24 h. The reaction mixture was cooled and water added (32 mL) to precipitate the product. The solids were collected by filtration and washed with EtOAc to furnish Compound B as a yellow solid (90%).

C.

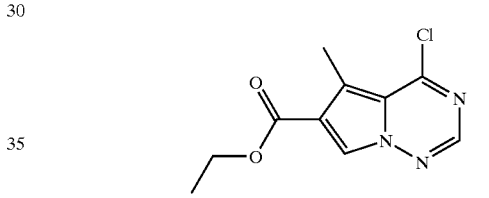

To a solution of Compound B (10 g, 45.2 mmol) in toluene (150 mL) was added DIPEA (6.31 mL, 36.2 mmol, 0.8 equiv) and POCl$_3$ (5.05 mL, 54.2 mmol, 1.2 equiv) and the reaction mixture heated at 120–125° C. (oil bath temp) for 20 h. The reaction mixture was cooled and poured into ice cold sat. NaHCO$_3$-water-toluene (450 mL-450 mL-150 mL) and stirred rapidly to assure quenching of the excess POCl$_3$. The layers were separated (filtered through celite if a suspension forms) and the organic layer was washed again with sat. NaHCO$_3$. The organic layer was dried over Na$_2$SO$_4$, filtered and concentrated in vacuo to afford Compound C as a tan yellow solid (9.9 g, 95%).

D.

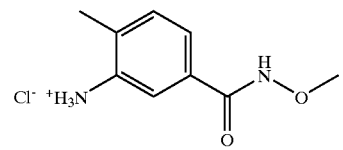

A mixture of commercially-available 4-amino-3-methylbenzoic acid (100 g, 0.66 mol) and N-(tert-butoxycarbonyl)anhydride (150 g, 0.68 mol) in THF (1000 mL) was slowly heated to 50° C. overnight. The resulting mixture was cooled to rt and the solvent was removed on a rotary evaporator. The resulting solids were triturated with hexanes and dried in vacuo to afford 151 g (91%) of the crude BOC-protected aniline intermediate as a light pink solid.

To the above, light-pink solid was added EDCI (127 g, 0.66 mol), HOBt (90 g, 0.66 mol), and DMF (1000 ml), and the resulting mixture was stirred at rt for 30 minutes followed by addition of methoxyamine hydrochloride (55 g, 0.66 mol) in one portion. After stirring for 10 min, the mixture was cooled using an ice bath. DIPEA (250 ml, 1.4 mol) was added at such a rate so as to maintain the internal reaction temperature below 25° C. After the addition was complete, the ice bath was removed and the reaction was stirred overnight at rt. The reaction mixture was partitioned between 0.5 L of water and 1.5 L of EtOAc and the resulting layers were separated. The aqueous portion was extracted with additional EtOAc (400 mL×3), and the combined organic extracts were washed with water (300 mL×3), cold 0.5 N aq. HCl (400 mL×2), and water (500 mL). The product was then extracted with cold 0.5 N aq. NaOH (300 mL×3) and the combined basic aqueous extracts were neutralized to pH=8 by a slow addition of cold 0.5 N aq. HCl. The resulting solid which precipitated was collected by filtration and washed with cold water. The wet solid was decolorized in hot EtOH with active charcoal to give 106 g of white solid as the BOC-protected N-methoxyamide intermediate.

To a slurry of the above solid (91 g, 0.32 mol) in 1,4-dioxane (400 mL) at rt was added a 4M solution of HCl in dioxane (400 mL), and the resulting mixture was stirred at rt overnight. Diethyl ether (1000 mL) was added and the precipitated solid was collected by filtration and triturated with a hot EtOH/H$_2$O mixture (4:1 v/v). Drying the resulting solid in vacuo afforded 53 g of the pure hydrochloride salt (Compound D) as a white solid. $_1$H NMR (d$_6$-DMSO): δ9.5–9.9 (br. s, 1H), 7.75 (s, 1H), 7.55 (d, 1H), 7.36 (d, 1H), 3.70 (s, 3H), 2.38 (s, 3H).

E.

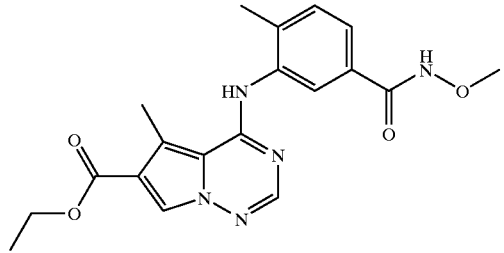

To a solution of the Compound D (41.2 g, 190 mmol) in DMF (230 mL) was added DIPEA (33.1 mL, 180.7 mmol, 0.95 equiv), and the reaction vessel was heated to 55° C. (oil bath temp). Solid Compound C (45.6 g, 190 mmol) was added in several portions over 10 minutes and the flask was rinsed with DMF (150 mL) and added to the reaction. The reaction was heated for 10 hours at 55° C. and cooled to rt. The mixture was then poured into 1.5 L water diluted to 2.2 L with ice slowly over 10 minutes. The pH was adjusted to 6 and the solids were stirred for 1 h. The solids were filtered, washed with water (2×200 mL) and dried on the filter to give 71.9 g crude ester. The solid was then suspended in acetonitrile (450 mL) and heated with stirring at 50° C. for 1 h. The mixture was cooled and filtered to give 64.2 g product (>99% purity). These solids were then dissolved in hot EtOH (2.8 L) and decolorizing carbon (6.4 g) was added followed by heating at reflux for 15 min. The mixture was then filtered through a pad of celite and the reaction flask rinsed with hot EtOH (1 L). The hot filtrate was then concentrated to ~1 L of EtOH by distillation upon which the product started to crystallize out of solution at a volume of 2.5 L. The solution was cooled and placed in a cold room with stirring for 40 h. The solids were filtered and rinsed with 1/1 EtOH/Et$_2$O (500 mL) to give 58.5 g of Compound E as a white solid (80%).

F. Example 61

To a solution of ester Compound E (22.5 g, 58.7 mmol) in THF (205 mL) was added 1 N NaOH (205 mL) and the reaction mixture heated to 50° C. for 16 h. The THF was removed in vacuo and the mixture was acidified to pH 4–5 with 1N aq. HCl to precipitate the product. The heterogeneous mixture was stirred for 1 h, filtered and washed with water (150 mL) and ether (150 mL). The collected solids were partially dried on the filter to give the crude acid intermediate as a moist white solid which was used without further purification.

To a solution of the moist acid in 300 mL of DMF was added HOBt (11.9 g, 88.0 mmol), EDCI (16.9 g, 88.0 mmol) and 1.3 equivalents (117 mmol) of cyclopropyl-amine as the free base or as the hydrochloride salt. The mixture was stirred for 30 min to solubilize the solids, placed in a cold water bath, and DIPEA (20.4 mL, 117 mmol) was added slowly via syringe. The reaction mixture was allowed to stir at rt for 1 h, then poured into rapidly stirred ice water (1.2 L) to precipitate the product. After stirring for 3 h, the solids were collected by suction filtration, washed with water (150 mL) and ether (2×100 mL), and allowed to air dry by suction filtration to give Example 61 (92–98%) as a white solid.

EXAMPLES 62–115

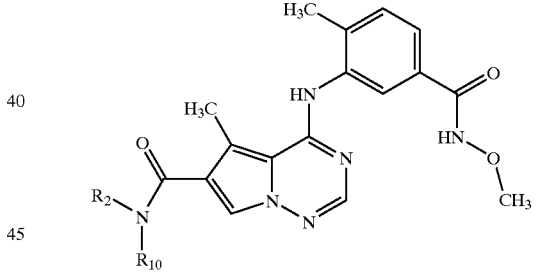

(IIc)

Compounds having the formula (IIc), wherein R$_2$ and R$_{10}$ have the values listed in Table 8 were prepared following the same methods set forth above in Scheme 9 and Example 61, using different amines (NR$_2$R$_{10}$) in the last step. Additionally, each compound can be recrystallized using a 7 to 1 EtOH/water mixture to afford analytically pure product as a white crystalline solid.

TABLE 8

| Ex. | R$_2$ | R$_{10}$ | Compound Name | Data MS/HPLC |
|---|---|---|---|---|
| 62 | —CH$_2$—C(CH$_3$)$_3$ | CH$_3$ | N-(2,2-Dimethylpropyl)-4-[[5-[(methoxyamino)carbonyl]-2-methylphenyl]amino]-N,5-dimethylpyrrolo[2,1-f][1,2,4]triazine-6-carboxamide | 439.3 3.43 min |

TABLE 8-continued

| Ex. | R₂ | R₁₀ | Compound Name | Data MS/HPLC |
|---|---|---|---|---|
| 63 | —CH—(CH₃)₂ | H | 4-[[5-[(Methoxyamino)carbonyl]-2-methylphenyl]amino]-5-methyl-N-(1-methylethyl)pyrrolo[2,1-f][1,2,4]triazine-6-carboxamide | 397.3 2.79 min |
| 64 | 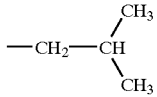 —CH₂—CH(CH₃)(CH₃) | H | 4-[[5-[(Methoxyamino)carbonyl]-2-methylphenyl]amino]-5-methyl-N-(2-methylpropyl)pyrrolo[2,1-f][1,2,4]triazine-6-carboxamide | 411.4 3.14 min |
| 65 | —CH₂—C(CH₃)₃ | H | N-(2,2-Dimethylpropyl)-4-[[5-[(methoxyamino)Carbonyl]-2-methylphenyl]amino]-5-methylpyrrolo[2,1-f][1,2,4]triazine-6-carboxamide | 425.3 3.35 min |
| 66 | —(CH₂)₂CH₃ | H | 4-[[5-[(Methoxyamino)carbonyl]-2-methylphenyl]amino]-5-methyl-N-propylpyrrolo[2,1-f][1,2,4]triazine-6-carboxamide | 397.2 2.88 min |
| 67 | —C(CH₃)₃ | H | N-(1,1-Dimethylethyl)-4-[[5-[(methoxyamino)carbonyl]-2-methylphenyl]amino]-5-methylpyrrolo[2,1-f][1,2,4]triazine-6-carboxamide | 411.2 3.11 min |
| 68 | —(CH₂)₂—OCH₃ | H | 4-[[5-[(Methoxyamino)carbonyl]-2-methylphenyl]amino]-N-(2-methoxyethyl)-5-methylpyrrolo[2,1-f][1,2,4]triazine-6-carboxamide | 413.2 1.99 min |
| 69 | 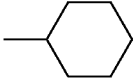 | H | N-Cyclohexyl-4-[[5-[(methoxyamino)carbonyl]-2-methylphenyl]amino]-5-methylpyrrolo[2,1-f][1,2,4]triazine-6-carboxamide | 437.4 2.88 min |
| 70 | 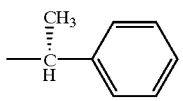 | H | 4-[[5-[(Methoxyamino)carbonyl]-2-methylphenyl]amino]-5-methyl-N-[(1R)-1-phenylethyl]pyrrolo[2,1-f][1,2,4]triazine-6-carboxamide | 459.3 2.85 min |
| 71 | 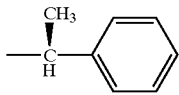 | H | 4-[[5-[(Methoxyamino)carbonyl]-2-methylphenyl]amino]-5-methyl-N-[(1S)-1-phenylethyl]pyrrolo[2,1-f][1,2,4]triazine-6-carboxamide | 459.3 2.85 min |
| 72 | 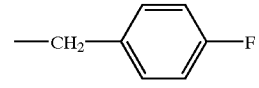 | H | N-[(4-Fluorophenyl)methyl]-4-[[5-[(methoxyamino)carbonyl]-2-methylphenyl]amino]-5-methylpyrrolo[2,1-f][1,2,4]triazine-6-carboxamide | 463.4 2.83 min |
| 73 | 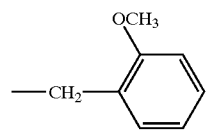 | H | 4-[[5-[(Methoxyamino)carbonyl]-2-methylphenyl]amino]-N-[(2-methoxyphenyl)methyl]-5-methylpyrrolo[2,1-f][1,2,4]triazine-6-carboxamide | 475.4 2.83 min |
| 74 | 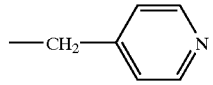 | H | 4-[[5-[(Methoxyamino)carbonyl]-2-methylphenyl]amino]-5-methyl-N-(4-pyridinylmethyl)pyrrolo[2,1-f][1,2,4]triazine-6-carboxamide | 446.2 1.45 min |
| 75 | 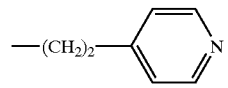 | H | 4-[[5-[(Methoxyamino)carbonyl]-2-methylphenyl]amino]-5-methyl-N-[2-(4-pyridinyl)ethyl]pyrrolo[2,1-f][1,2,4]triazine-6-carboxamide | 460.3 1.81 min |
| 76 | 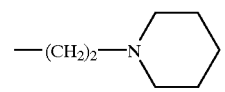 | H | 4-[[5-[(Methoxyamino)carbonyl]-2-methylphenyl]amino]-5-methyl-N-[2-(1-piperidinyl)ethyl]pyrrolo[2,1-f][1,2,4]triazine-6-carboxamide | 466.4 1.56 min |

TABLE 8-continued

| Ex. | R₂ | R₁₀ | Compound Name | Data MS/HPLC |
|---|---|---|---|---|
| 77 | —(CH₂)₂—N(morpholinyl) | H | 4-[[5-[(Methoxyamino)carbonyl]-2-methylphenyl]amino]-5-methyl-N-[2-(4-morpholinyl)ethyl]pyrrolo[2,1-f][1,2,4]triazine-6-carboxamide | 468.3 1.38 min |
| 78 | (1R,2S)-2-hydroxy-1-methylindanyl | H | N-[(1R,2S)-2,3-Dihydro-1H-inden-1-yl]-4-[[5-[(methoxyamino)carbonyl]-2-methylphenyl]amino]-5-methylpyrrolo[2,1-f][1,2,4]triazine-6-carboxamide | 487.4 2.74 min |
| 79 | (1S,2R)-2-hydroxy-1-methylindanyl | H | N-[(1S,2R)-2,3-Dihydro-1H-inden-1-yl]-4-[[5-[(methoxyamino)carbonyl]-2-methylphenyl]amino]-5-methylpyrrolo[2,1-f][1,2,4]triazine-6-carboxamide | 487.2 2.74 min |
| 80 | cyclopropyl | H | N-Cyclopropyl-4-[[5-[(methoxyamino)carbonyl]-2-methylphenyl]amino]-5-methylpyrrolo[2,1-f][1,2,4]triazine-6-carboxamide | 395.3 2.64 min |
| 81 | cyclopentyl | H | N-Cyclopentyl-4-[[5-[(methoxyamino)carbonyl]-2-methylphenyl]amino]-5-methylpyrrolo[2,1-f][1,2,4]triazine-6-carboxamide | 423.0 3.15 min |
| 82 | —(CH₂)₂—(4-fluorophenyl) | H | N-[2-(4-Fluorophenyl)ethyl]-4-[[5-[(methoxyamino)carbonyl]-2-methylphenyl]amino]-5-methylpyrrolo[2,1-f][1,2,4]triazine-6-carboxamide | 477.3 3.53 min |
| 83 | —CH₂—cyclohexyl | H | N-(Cyclohexylmethyl)-4-[[5-[(methoxyamino)carbonyl]-2-methylphenyl]amino]-5-methylpyrrolo[2,1-f][1,2,4]triazine-6-carboxamide | 451.3 3.70 min |
| 84 | —CH₂—(tetrahydro-2-furanyl) | H | 4-[[5-[(Methoxyamino)carbonyl]-2-methylphenyl]amino]-5-methyl-N-[(tetrahydro-2-furanyl)methyl]pyrrolo[2,1-f][1,2,4]triazine-6-carboxamide | 439.3 2.76 min |
| 85 | —(CH₂)₂—(1H-indol-3-yl) | H | N-(2-1H-Indol-3-ylethyl)-4-[[5-[(methoxyamino)carbonyl]-2-methylphenyl]amino]-5-methylpyrrolo[2,1-f][1,2,4]triazine-6-carboxamide | 498.3 3.39 min |
| 86 | —(CH₂)₃—CH₃ | H | N-Butyl-4-[[5-[(methoxyamino)carbonyl]-2-methylphenyl]amino]-5-methylpyrrolo[2,1-f][1,2,4]triazine-6-carboxamide | 411.2 3.16 min |

TABLE 8-continued

| Ex. | R₂ | R₁₀ | Compound Name | Data MS/HPLC |
|---|---|---|---|---|
| 87 | —CH₂-cyclopropyl | H | N-(Cyclopropylmethyl)-4-[[5-[(methoxyamino)carbonyl]-2-methylphenyl]amino]-5-methylpyrrolo[2,1-f][1,2,4]triazine-6-carboxamide | 409.1  2.90 min |
| 88 | (CH₃)(CH₃CH₂)CH—CH(CH₃) (2-methylbutyl) | H | 4-[[5-[(Methoxyamino)carbonyl]-2-methylphenyl]amino]-5-methyl-N-(2-methylbutyl)pyrrolo[2,1-f][1,2,4]triazine-6-carboxamide | 425.3  3.43 min |
| 89 | —CH₂-(2-furanyl) | H | N-(2-Furanylmethyl)-4-[[5-[(methoxyamino)carbonyl]-2-methylphenyl]amino]-5-methylpyrrolo[2,1-f][1,2,4]triazine-6-carboxamide | 435.1  2.95 min |
| 90 | —CH₂-(2-thienyl) | H | 4-[[5-[(Methoxyamino)carbonyl]-2-methylphenyl]amino]-5-methyl-N-(2-thienylmethyl)pyrrolo[2,1-f][1,2,4]triazine-6-carboxamide | 451.2  3.16 min |
| 91 | —(CH₂)₂—O-phenyl | H | 4-[[5-[(Methoxyamino)carbonyl]-2-methylphenyl]amino]-5-methyl-N-(2-phenoxyethyl)pyrrolo[2,1-f][1,2,4]triazine-6-carboxamide | 475.3  3.43 min |
| 92 | 2-methylcyclohexyl | H | 4-[[5-[(Methoxyamino)carbonyl]-2-methylphenyl]amino]-5-methyl-N-(2-methylcyclohexyl)pyrrolo[2,1-f][1,2,4]triazine-6-carboxamide | 451.2  3.56 min |
| 93 | —CH₂—CH₃ | CH₃ | N-Ethyl-4-[[5-[(methoxyamino)carbonyl]-2-methylphenyl]amino]-N,5-dimethylpyrrolo[2,1-f][1,2,4]triazine-6-carboxamide | 397.2  2.59 min |
| 94 | —CH₂—CF₃ | H | 4-[[5-[(Methoxyamino)carbonyl]-2-methylphenyl]amino]-5-methyl-N-(2,2,2-trifluoroethyl)pyrrolo[2,1-f][1,2,4]triazine-6-carboxamide | 437.1  3.01 min |
| 95 | —CH₂—CH₂—F | H | N-(2-Fluoroethyl)-4-[[5-[(methoxyamino)carbonyl]-2-methylphenyl]amino]-5-methylpyrrolo[2,1-f][1,2,4]triazine-6-carboxamide | 401.2  2.44 min |
| 96 | 2,3-dihydro-1H-inden-2-yl | H | N-(2,3-Dihydro-1H-inden-2-yl)-4-[[5-[(methoxyamino)carbonyl]-2-methylphenyl]amino]-5-methylpyrrolo[2,1-f][1,2,4]triazine-6-carboxamide | 471.2  3.56 min |
| 97 | —CH₂—CH₃ | H | N-Ethyl-4-[[5-[(methoxyamino)carbonyl]-2-methylphenyl]amino]-5-methylpyrrolo[2,1-f][1,2,4]triazine-6-carboxamide | 383.3  2.58 min |
| 98 | H₂C—CF₂—CF₃ | H | 4-[[5-[(Methoxyamino)carbonyl]-2-methylphenyl]amino]-5-methyl-N-(2,2,3,3,3-pentafluoropropyl)pyrrolo[2,1-f][1,2,4]triazine-6-carboxamide | 487.2  3.40 min |
| 99 | —(CH₂)₂—N(CH₃)₂ | H | 4-[[5-[(Methoxyamino)carbonyl]-2-methylphenyl]amino]-5,7-dimethyl-N-(1-methylethyl)pyrrolo[2,1-f][1,2,4]triazine-6-carboxamide | 426.5  1.38 min |
| 100 | 4-fluorophenyl | H | N-(4-Fluorophenyl)-4-[[5-[(methoxyamino)carbonyl]-2-methylphenyl]amino]-5-methylpyrrolo[2,1-f][1,2,4]triazine-6-carboxamide | 449.2  2.92 min |

TABLE 8-continued

| Ex. | R₂ | R₁₀ | Compound Name | Data MS/HPLC |
|---|---|---|---|---|
| 101 | 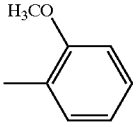 | H | 4-[[5-[(Methoxyamino)carbonyl]-2-methylphenyl]amino]-N-(2-methoxyphenyl)-5-methylpyrrolo[2,1-f][1,2,4]triazine-6-carboxamide | 461.2 2.97 min |
| 102 | 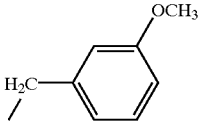 | H | 4-[[5-[(Methoxyamino)carbonyl]-2-methylphenyl]amino]-N-[(3-methoxyphenyl)methyl]-5-methylpyrrolo[2,1-f][1,2,4]triazine-6-carboxamide | 475.4 2.75 min |
| 103 | 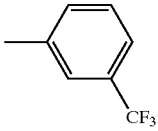 | H | 4-[[5-[(Methoxyamino)carbonyl]-2-methylphenyl]amino]-5-methyl-N-[3-(trifluoromethyl)phenyl]pyrrolo[2,1-f][1,2,4]triazine-6-carboxamide | 499.1 3.39 min |
| 104 | 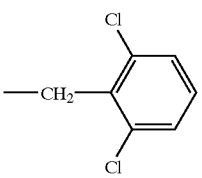 | H | N-[(2,6-Dichlorophenyl)methyl]-4-[[5-[(methoxyamino)carbonyl]-2-methylphenyl]amino]-5-methylpyrrolo[2,1-f][1,2,4]triazine-6-carboxamide | 513.1 3.10 min |
| 105 | 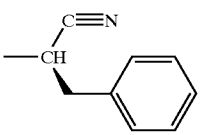 | H | N-[(1S)-1-Cyano-2-phenylethyl]-4-[[5-[(methoxyamino)carbonyl]-2-methylphenyl]amino]-5-methylpyrrolo[2,1-f][1,2,4]triazine-6-carboxamide | 484.3 2.88 min |
| 106 | 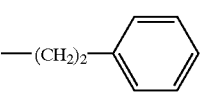 | H | 4-[[5-[(Methoxyamino)carbonyl]-2-methylphenyl]amino]-5-methyl-N-(2-phenylethyl)pyrrolo[2,1-f][1,2,4]triazine-6-carboxamide | 459.3 2.91 min |
| 107 | 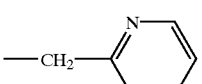 | H | 4-[[5-[(Methoxyamino)carbonyl]-2-methylphenyl]amino]-5-methyl-N-(2-pyridinylmethyl)pyrrolo[2,1-f][1,2,4]triazine-6-carboxamide | 446.2 1.51 min |
| 108 | 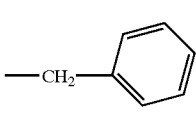 | H | 4-[[5-[(Methoxyamino)carbonyl]-2-methylphenyl]amino]-5-methyl-N-(phenylmethyl)pyrrolo[2,1-f][1,2,4]triazine-6-carboxamide | 445.2 2.69 min |
| 109 | 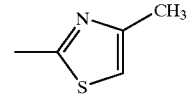 | H | 4-[[5-[(Methoxyamino)carbonyl]-2-methylphenyl]amino]-5-methyl-N-(4-methyl-2-thiazolyl)pyrrolo[2,1-f][1,2,4]triazine-6-carboxamide | 452.3 3.50 min |
| 110 | 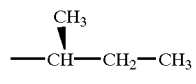 | H | 4-[[5-[(Methoxyamino)carbonyl]-2-methylphenyl]amino]-5-methyl-N-[(1R)-1-methylpropyl]pyrrolo[2,1-f][1,2,4]triazine-6-carboxamide | 411.2 3.20 min |
| 111 | 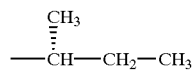 | H | 4-[[5-[(Methoxyamino)carbonyl]-2-methylphenyl]amino]-5-methyl-N-[(1S)-1-methylpropyl]pyrrolo[2,1-f][1,2,4]triazine-6-carboxamide | 411.2 3.20 min |
| 112 | 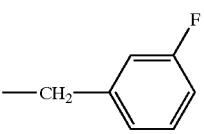 | H | N-[(3-Fluorophenyl)methyl]-4-[[5-[(methoxyamino)carbonyl]-2-methylphenyl]amino]-5-methylpyrrolo[2,1-f][1,2,4]triazine-6-carboxamide | 463.2 2.84 min |

TABLE 8-continued

| Ex. | R₂ | R₁₀ | Compound Name | Data MS/HPLC |
|---|---|---|---|---|
| 113 | 1-(4-fluorophenyl)ethyl group (CH(CH₃)-C₆H₄-F) | H | N-[1-(4-Fluorophenyl)ethyl]-4-[[5-[(methoxyamino)carbonyl]-2-methylphenyl]amino]-5-methylpyrrolo[2,1-f][1,2,4]triazine-6-carboxamide | 477.3 2.93 min |
| 114 | (2,4-difluorophenyl)methyl (-CH₂-C₆H₃(F)₂ at 2,4) | H | N-[(2,4-Difluorophenyl)methyl]-4-[[5-[(methoxyamino)carbonyl]-2-methylphenyl]amino]-5-methylpyrrolo[2,1-f][1,2,4]triazine-6-carboxamide | 481.2 2.92 min |
| 115 | (2,6-difluorophenyl)methyl (-CH₂-C₆H₃(F)₂ at 2,6) | H | N-[(2,6-Difluorophenyl)methyl]-4-[[5-[(methoxyamino)carbonyl]-2-methylphenyl]amino]-5-methylpyrrolo[2,1-f][1,2,4]triazine-6-carboxamide | 481.1 2.70 min |

EXAMPLES 116–119

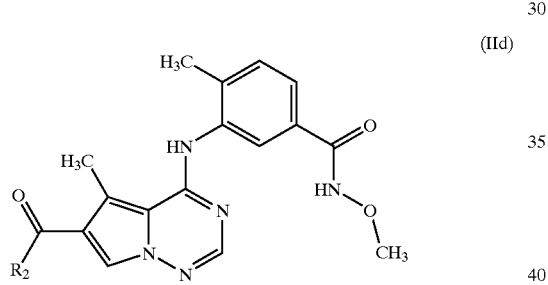

(IId)

Compounds having the formula (IId), wherein the R₂ groups have the values listed in Table 9, were prepared following the same methods set forth above in Scheme 9 and Examples 62–115.

TABLE 9

| Ex. | R₂ | Compound Name | Data |
|---|---|---|---|
| 116 | 4-methyl-1,4-diazepan-1-yl | 3-[[6-[(Hexahydro-4-methyl-1H-1,4-diazepin-1-yl)carbonyl]-5-methyl pyrrolo[2,1-f][1,2,4]triazin-4-yl]amino]-N-methoxy-4-methylbenzamide | 452.1 1.63 min |
| 117 | morpholin-4-yl | N-Methoxy-4-methyl-3-[[5-methyl-6-(4-morpholinylcarbonyl)pyrrolo[2,1-f][1,2,4]triazin-4-yl]amino]benzamide | 425.2 1.82 min |
| 118 | 4-benzylpiperidin-1-yl | N-Methoxy-4-methyl-3-[[5-methyl-6-[[4-(phenylmethyl)-1-piperidinyl]carbonyl]pyrrolo[2,1-f][1,2,4]triazin-4-yl]amino]benzamide | 513.4 3.45 min |

TABLE 9-continued

| Ex. | R₂ | Compound Name | Data |
|---|---|---|---|
| 119 | pyrrolidinyl (N-methyl) | N-Methoxy-4-methyl-3-[[5-methyl-6-(1-pyrrolidinylcarbonyl)pyrrolo[2,1-f][1,2,4]triazin-4-yl]amino]benzamide | 409.2<br>2.16 min |

EXAMPLES 120–124

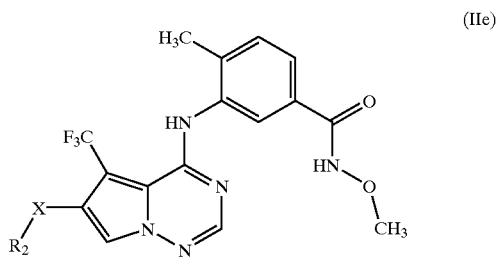

(IIe)

Compounds having the formula (IIe), wherein X and R₂ have the values listed in table 10, were prepared following the same or similar procedure as in Scheme 9 and Example 61, except in the first step, commercially available 3-trifluoromethyl-1-pyrrole-2,4-diethyl ester was used instead of 3-methyl-1-pyrrole-2,4-diethyl ester.

TABLE 10

| Ex. No. | X | R₂ | Compound Name | Data MS/HPLC |
|---|---|---|---|---|
| 120 | —C(=O)—O— (ester) | —CH₂—CH₃ | 4-[[5-[(Methoxyamino)carbonyl]-2-methylphenyl]amino]-5-(trifluoromethyl)pyrrolo[2,1-f][1,2,4]triazine-6-carboxylic acid ethyl ester | 438.2<br>3.76 min |
| 121 | —C(=O)—NH— | —CH₂—CH₃ | N-Ethyl-4-[[5-[(methoxyamino)carbonyl]-2-methylphenyl]amino]-5-(trifluoromethyl)pyrrolo[2,1-f][1,2,4]triazine-6-carboxamide | 437.2<br>2.99 min |
| 122 | —C(=O)—NH— | —CH₂—CH₂—CH₃ | 4-[[5-[(Methoxyamino)carbonyl]-2-methylphenyl]amino]-N-propyl-5-(trifluoromethyl)pyrrolo[2,1-f][1,2,4]triazine-6-carboxamide | 451.3<br>3.21 min |
| 123 | —C(=O)—NH— | —CH(CH₃)—CH₂—CH₃ | 4-[[5-[(Methoxyamino)carbonyl]-2-methylphenyl]amino]-N-[(1S)-1-methylpropyl]-5-(trifluoromethyl)pyrrolo[2,1-f][1,2,4]triazine-6-carboxamide | 465.3<br>3.36 min |
| 124 | —C(=O)—NH— | —C(CH₃)(H)—phenyl | 4-[[5-[(Methoxyamino)carbonyl]-2-methylphenyl]amino]-N-[(1S)-1-phenylethyl]-5-(trifluoromethyl)pyrrolo[2,1-f][1,2,4]triazine-6-carboxamide | 513.2<br>1.72 min |

EXAMPLE 125

N-Ethyl-4-[[5-[(methoxyamino)carbonyl]-2-methylphenyl]amino]-5-methylpyrrolo[2,1-f][1,2,4]triazine-6-carboxamide methane sulfonic acid

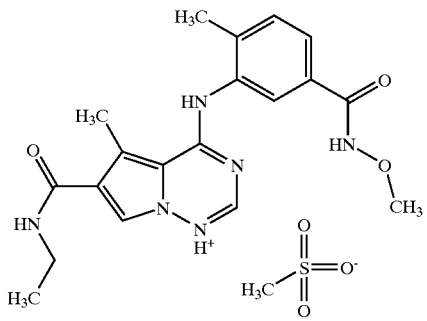

Example 97 as a free base was charged with acetone (10 ml/g Ex. 106), and the jacket was heated to 50–60° C. Reflux was started at 55–57° C., and the mixture was stirred for 30 min. at 50–60° C. Methanesulfonic acid (1.2 eq.) was added, and a slight exotherm was observed. The slurry was stirred at 50–60° C. until DSC showed in two consecutive samples the complete conversion of the free base (mp 220–222° C.) to the mesylate salt (mp 259–261° C.). The slurry was cooled to 20–25° C. over about 30 min, and then stirred for at least 30 min. with the temp. kept at 20–25° C. The slurry was then filtered, washed with acetone, and dried in vacuo at 40–50° C. to an LOD <0.5% to provide Example 125 as a white crystalline solid (yield 90–95%). $[M+H]^+ = 478.4$. The above procedure may be used to prepare mesylate salts of other compounds of Formulae (I) and (II) herein.

EXAMPLE 126

N-Ethyl-5-methyl-4-[[2-methyl-5-[[[3-(trifluoromethyl)phenyl]amino]carbonyl]phenyl]amino]pyrrolo[2,1-f][1,2,4]triazine-6-carboxamide

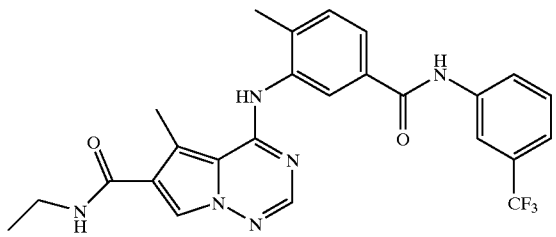

A. To a slurry of 2.0 g (4.2 mmol) of compound (1) from Scheme 10, wherein $R_2$ is ethyl, in 12 mL of anhydrous MeOH was added 18 mL of a 4 N solution of anhydrous HCl in dioxane at rt. The resulting clear solution was stirred at rt for 16 h and the reaction mixture was concentrated in vacuo. The resulting oil was dissolved in 16 mL of 1.5 N aq. KOH solution and heated to 50° C. for 3 h. After cooling to rt, the mixture was diluted with 50 mL of water and 10% aq. HCl was added until pH was approximately 3 or 4. The resulting precipitated product was collected by vacuum filtration and washed with 50 mL of water and dried in vacuo to afford 1.47 g (99%) of compound (3) from Scheme 10. An analytical sample of this product was prepared by recrystallization from 10% aq. acetonitrile. $^1$H NMR (CD$_3$OD): δ8.21 (br s, 1H), 8.11 (br s, 1H), 7.89–7.91 (m, 2H), 7.67 (br s, 1H), 7.44 (d, 1H), 3.40 (q, 2H), 2.86 (s, 3H), 2.36 (s, 3H), 1.25 (s, 3H). LCMS (M+H$^+$)=354.2. HPLC (Condition A): 2.24 min.

B. A mixture of Compound A (40 mg, 0.11 mmol), HATU (65 mg, 0.17 mmol), diisopropylamine (20 μL, 0.11 mmol), and 3-trifluoromethylaniline (36 mg, 0.22 mmol) in 0.3 mL of N-methylpyrrolidinone was heated at 80° C. for 16 h, and the reaction mixture was purified by RP preparative HPLC to afford 41 mg (74%) of Example 126 as a light tan solid. $^1$H NMR (CD$_3$OD w/TFA): δ8.28 (s, 1H), 8.19 (s, 1H), 8.16 (d, 1H), 8.11 (d, 1H), 7.84 (s, 1H), 7.71 (d, 1H), 7.58 (t, 2H), 7.47 (d, 1H), 3.44 (q, 2H), 2.94 (s, 3H), 2.47 (s, 3H), 1.26 (t, 3H). LCMS (M+H$^+$)=497.47. HPLC (Condition A): 3.30 min.

EXAMPLES 127–129

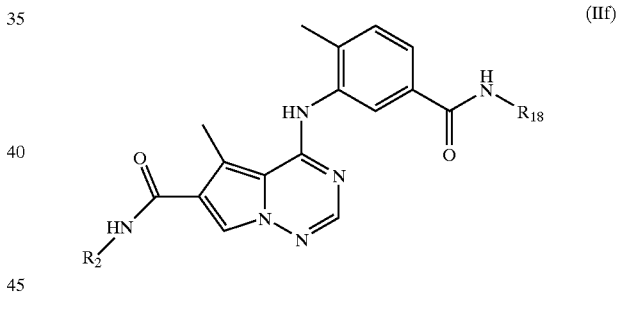

Compounds of Formula (IIf) were prepared as described for Example 126, except appropriate substrates and amines were selected to afford compounds where $R_2$ and $R_{18}$ have the values listed in Table 11.

TABLE 11

| Ex. | $R_2$ | $R_{18}$ | Compound Name | Data |
|---|---|---|---|---|
| 127 | Et | ![4-cyanophenyl] | 4-[[5-[[(4-Cyanophenyl)amino]carbonyl]-2-methylphenyl]amino]-N-ethyl-5-methyl pyrrolo[2,1-f][1,2,4]triazine-6-carboxamide | $^1$H NMR (CD$_3$OD): δ 7.93(br s, 1H), 7.84–7.86(d, 3H), 7.74(d, 1H), 7.62(d, 2H), 7.58 (s, 1H), 7.40(d, 1H), 3.30(q, 2H), 3.21(s, 3H), 2.76(s, 3H), 1.14 (t, 3H). LCMS(M+H$^+$)= 454.18. HPLC (Condition A): 2.86 min. |

TABLE 11-continued

| Ex. | R₂ | R₁₈ | Compound Name | Data |
|---|---|---|---|---|
| 128 | 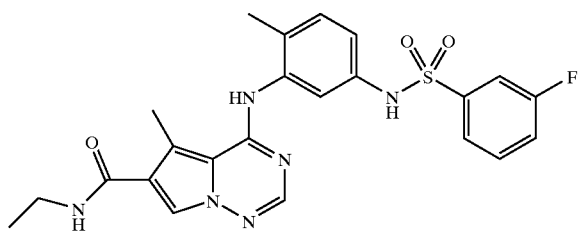 | | 5-Methyl-4-[[2-methyl-5-[(phenylamino)carbonyl]phenyl]amino]-N-[(1S)-1-phenylethyl]pyrrolo[2,1-f][1,2,4]triazine-6-carboxamide | LCMS (M+H⁺)= 505.27. HPLC (Condition A): 3.34 min. |
| 129 | | | 4-[[5-[[(4-Cyanophenyl)amino]carbonyl]-2-methylphenyl]amino]-5-methyl-N-[(1S)-1-phenylethyl]pyrrolo[2,1-f][1,2,4]triazine-6-carboxamide | LCMS (M+H⁺)= 530.23. HPLC (Condition A): 3.35 min. |

EXAMPLE 130

N-Ethyl-4-[[5-[[(3-fluorophenyl)sulfonyl]amino]-2-methylphenyl]amino]-5-methylpyrrolo[2,1-f][1,2,4]triazine-6-carboxamide

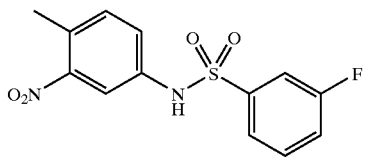

A.

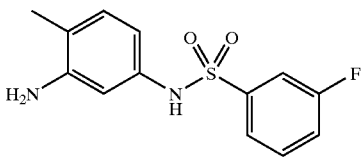

To a solution of 4-methyl-3-nitroaniline [compound (11) from Scheme 11](3.72 g, 24.5 mmol)] in 150 ml of DCM at rt was added 3-fluorobenzenesulfonyl chloride (5.00 g, 25.7 mmol), followed by TEA (7.0 ml, 50.2 mmol) via syringe. The resulting mixture was stirred for 20 h and the solvent removed in vacuo. The residue was dissolved in DCM (600 ml), washed with sat'd aq. NaHCO₃, dried over sodium sulfate, filtered, and concentrated in vacuo to give 8.00 g of dark solid which was triturated with DCM to afford 5.46 g of yellow solid. A portion of this solid (1.63 g) was dissolved in 10 ml 1N aq. NaOH and 20 ml THF, and the solution was stirred at rt for 20 h. The solvent was removed in vacuo and the residue acidified with 3N HCl to a pH of 2. The resulting precipitated solid was collected by filtration to afford 1.02 g (94%) of a light yellow solid as the desired Compound A. HPLC (Condition A)=2.99 min. ¹HNMR(CDCl₃) δ7.67 (d, 1H), 7.59 (dd, 1H), 7.49 (m, 2H), 7.32 (m, 1H), 7.28 (m, 2H), 2.54 (s, 3H).

B.

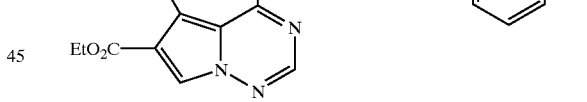

To 0.20 g (0.64 mmol) of Compound A in MeOH (10 ml) was added 10% Pd/C (20 mg) and the mixture stirred under hydrogen balloon for 6 h at rt. The solution was filtered through a pad of celite and the solvent removed in vacuo to give 0.18 g (100%) of Compound B as a colorless, glassy solid. HPLC (Conditions A): 1.77 min. LCMS M+H⁺(m/z) 281.

C.

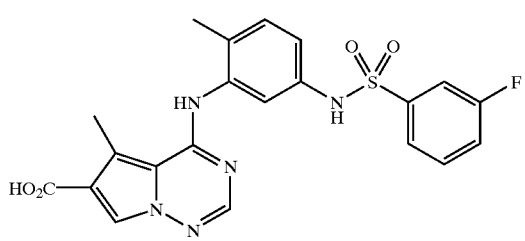

Compound B (0.18 g, 0.64 mmol) and 0.15 g (0.64 mmol) of 4-chloro-5-methylpyrrolotriazine-6-ethylcarboxylate (compound 8 of Scheme 11) in anhydrous DMF was stirred at rt for 20 h. The reaction was quenched with addition of cold water and sat'd aq. NaHCO₃. The solid was collected, washed with water, and dried in vacuo to give 0.27 g (91%) of Compound C as a light yellow solid. HPLC (Condition A: 3.49 min. LCMS M+H⁺(m/z) 484.

D.

A solution of 0.27 g (56 mmol) of Compound C in 1 ml of 1N aq. NaOH and 3 ml of MeOH was heated at 60° C. for 12 hr. The MeOH was removed in vacuo and the aqueous portion acidified with 1N aq. hydrogen chloride to pH ~2. The resulting precipitated solid was collected, washed with water, and dried in vacuo to afford 0.25 g (98%) of Compound D as a pale yellow solid. HPLC (Condition A): 2.93 min. LCMS M+H$^+$(m/z) 456.

E. Example 130

A mixture of 30 mg (66 μmol) of Compound D, EDCI (19 mg, 98 μmol), HOBt (13 mg, 98 μmol) and Hunig's base (43 μL, 0.25 mmol) was stirred at rt for 0.5 hr. Ethylamine hydrochloride (10 mg, 0.13 mmol) was added and the mixture stirred for 16 hr. The crude mixture was purified by RP preparative HPLC chromatography to give Example 130. HPLC (Conditions A): 2.83 min. LCMS M+H$^+$(m/z) 483.

EXAMPLES 131–132

Examples 131 and 132 as shown in Table 12 were prepared from Compound D of Example 130 and an appropriate amine as described in Example 130, step E.

EXAMPLES 133–141

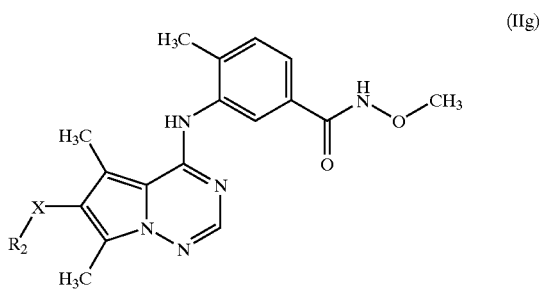

(IIg)

Compounds having the formula (IIg), wherein X and $R_2$ have the values listed in Table 13 were prepared from commercially-available diethyl-2,4-dimethylpyrrole-3,5-dicarboxylate following the same or similar procedure described above for the preparation of 5-desmethyl pyrrolotriazine.

TABLE 12

| Ex | Compound | Compound Name | Data |
|---|---|---|---|
| 131 | | 4-[[5-[[(3-Fluorophenyl)sulfonyl]amino]-2-methylphenyl]amino]-N-[(1S)-2-methoxy-1-methylethyl]-5-methylpyrrolo[2,1-f][1,2,4]triazine-6-carboxamide | HPLC (Condition A): 2.89 min. MH$^+$ (m/z) 527. |
| 132 | | 4-[[5-[[(3-Fluorophenyl)sulfonyl]amino]-2-methylphenyl]amino]-5-methyl-N-[(1S)-1-phenylethyl]pyrrolo[2,1-f][1,2,4]triazine-6-carboxamide | HPLC (Condition A): 3.23 min. MH$^+$ (m/z) 559. |

TABLE 13

| Ex | X | R₂ | Compound Name | Data |
|---|---|---|---|---|
| 133 | —CO₂— | Et | 4-[[5-[(Methoxy-amino)carbonyl]-2-methylphenyl]amino]-5,7-dimethylpyrrolo[2,1-f][1,2,4]triazine-6-carboxylic acid ethyl ester | 398.2, M+H 3.13 min, A |
| 134 | —C(=O)NH— | Et | N-Ethyl-4-[[5-[(methoxy amino)carbonyl]-2-methylphenyl]amino]-5,7-dimethylpyrrolo[2,1-f][1,2,4]triazine-6-carboxamide | 397.2, M+H 1.70 min, A |
| 135 | —C(=O)NH— | 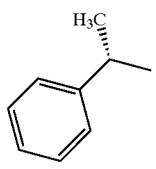 | 4-[[5-[(Methoxy-amino)carbonyl]-2-methylphenyl]amino]-5,7-dimethyl-N-[(1S)-1-phenylethyl]pyrrolo[2,1-f][1,2,4]triazine-6-carboxamide | 473.3, M+H 2.51 min, A |
| 136 | —C(=O)NH— | —CH(CH₃)₂ | 4-[[5-[(Methoxy-amino)carbonyl]-2-methylphenyl]amino]-5,7-dimethyl-N-(1-methylethyl)pyrrolo[2,1-f][1,2,4]triazine-6-carboxamide | 411.2, M+H 1.81 min, A |
| 137 | —C(=O)NH— | 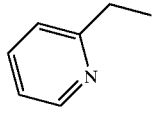 | 4-[[5-[(Methoxy-amino)carbonyl]-2-methylphenyl]amino]-5,7-dimethyl-N-(2-pyridinylmethyl)pyrrolo[2,1-f][1,2,4]triazine-6-carboxamide | 460.2, M+H 1.30 min, A |
| 138 | —CO₂— | H | 4-[[5-[(Methoxy amino)carbonyl]-2-methylphenyl]amino]-5,7-dimethylpyrrolo[2,1-f][1,2,4]triazine-6-carboxylic acid | 370.2, M+H 2.21 min, A |
| 139 | —C(=O)NH— | 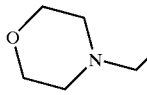 | 4-[[5-[(Methoxy-amino)carbonyl]-2-methylphenyl]amino]-5,7-dimethyl-N-[2-(4-morpholinyl)ethyl]pyrrolo[2,1-f][1,2,4]triazine-6-carboxamide | 482.1, M+H 1.21 min, A |
| 140 | —C(=O)NH— | 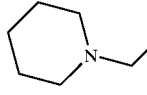 | 4-[[5-[(Methoxy-amino)carbonyl]-2-methylphenyl]amino]-5,7-dimethyl-N-[2-(1-piperidinyl)ethyl]pyrrolo[2,1-f][1,2,4]triazine-6-carboxamide | 480.2, M+H 1.39 min, A |
| 141 | —C(=O)NH— | 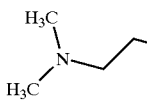 | N-[2-(Dimethylamino) ethyl]-4-[[5-[(methoxy amino)carbonyl]-2-methylphenyl]amino]-5,7-dimethylpyrrolo[2,1-f][1,2,4]triazine-6-carboxamide | 440.2, M+H 1.09 min, A |

EXAMPLE 142

4-[[5-[[(Ethylamino)carbonyl]amino]-2-methylphenyl]amino]-5-methyl-N-propyl pyrrolo[2,1-f][1,2,4]triazine-6-carboxamide

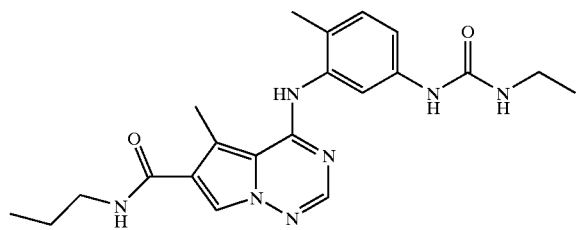

A. 5-Methyl-4-[(2-methyl-5-nitrophenyl)amino]pyrrolo[2,1-f][1,2,4]triazine-6-carboxylic acid ethyl ester

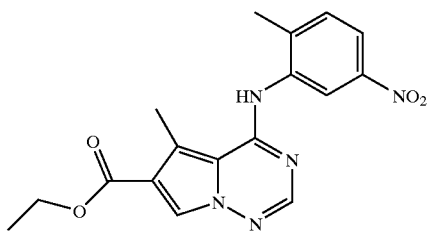

A suspension of chloropyrrolotriazine (compound 1 from Scheme 12) (2.03 g, 8.47 mmol) and 3-nitro-5-methyl aniline (1.41 g, 9.3 mmol) in DMF (25 mL) was stirred at rt for 24 h. Water (125 mL) was added over 30 min and the solution stirred for 1 h upon which the pH was adjusted to neutral with sat. aq. NaHCO$_3$. The solids were filtered, washed with water, and dried to give compound A (2.589 g, 85% yield) as a pale tan solid.

B. 5-Methyl-4-[(2-methyl-5-nitrophenyl)amino]pyrrolo[2,1-f][1,2,4]triazine-6-carboxylic acid

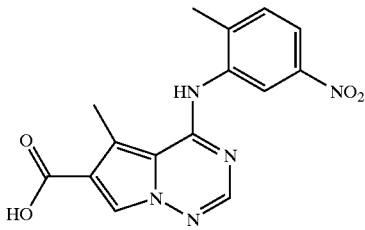

To a solution of Compound A (825 mg, 2.32 mmol) in THF (2 mL) and MeOH (1 mL) was added 1N NaOH (6 mL) and the reaction heated at 60° C. for 24 h. The reaction mixture was cooled, concentrated to remove the organic solvents, and the pH was adjusted to neutral with 1 N HCl. The solids were filtered, washed with water, and dried to give compound B. LCMS (M+H$^+$)=328.1. HPLC (Condition A): 3.40 min.

C. 5-methyl-4-[(2-methyl-5-nitrophenyl)amino]-N-propylpyrrolo[2,1-f][1,2,4]triazine-6-carboxamide

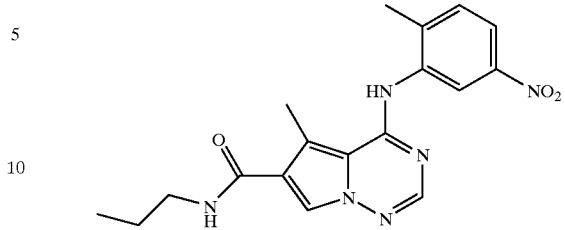

A solution of compound B (2.32 mmol), EDCI (489 mg, 2.55 mmol), and HOBt (345 mg, 2.55 mmol) in DMF (6 mL) was stirred at rt for 1 h, and then n-propyl amine (0.38 mL, 6.4 mmol) was added. The reaction was stirred for 4 h and water was added to precipitate the product. The solids were filtered and purified via column chromatography on silica (33% ethyl acetatehexanes) to give compound C (0.79 g, 93% yield) as a white solid. $^1$H NMR (CDCl$_3$): δ9.11 (s, 1H), 7.92 (m, 2H), 7.71 (s, 1H), 7.36 (d, J=8.4 Hz, 1H), 5.82 (br m, 1H), 3.34 (q, J=6.7 Hz, 2H), 2.86 (s, 3H), 2.41 (s, 3H), 1.58 (m, 2H), 1.16 (t, J=7.5 Hz, 3H). LCMS (M+H$^+$)=369.3. HPLC (Condition A): 3.42 min.

D. 4-[(5-Amino-2-methylphenyl)amino]-5-methyl-N-propylpyrrolo[2,1-f][1,2,4]triazine-6-carboxamide

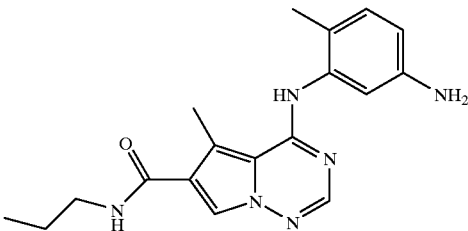

A solution of compound C (794 mg, 2.16 mmol) and 10% Pd/C (250 mg, wet) in MeOH (20 mL,) was degassed and backfilled with hydrogen three times and stirred for 2 h. The solution was filtered and concentrated to give compound D (691 mg, 95% yield). $^1$H NMR (CDCl$_3$): δ7.94 (s, 1H), 7.73 (s, 1H), 7,53 (s, 1H), 7.23 (m, 1H), 7.06 (d, J=8.1 Hz, 1H), 6.53 (dd, J=8.1, 2.2 Hz, 1H) 5.86 (br m, 1H), 3.43 (q, J=6.6 Hz, 2H), 2.91 (s, 3H), 2.27 (s, 3H), 1.68 (m, 2H), 1.02 (t, J=7.3 Hz, 3H). LCMS (M+H$^+$)=339.2. HPLC (Condition A): 2.39 min.

E. Example 142

To a suspension of 25.6 g (0.076 mmol) of compound D in 0.3 mL of DCE was added 22 μL of ethyl isocyanate at rt. The reaction mixture was heated at 50° C. for 12 h, then cooled, and isopropanol was added (1 mL). The resulting precipitated product was collected by vacuum filtration and washed with 1 mL of isopropanol and dried in vacuo to afford 19.6 mg (63%) of the titled compound as a pure product. $^1$H NMR (CD$_3$OD): δ7.94 (s, 1H), 7.70 (s, 1H), 7.60 (s, 1H), 7.23 (br s, 2H), 7.44 (d, 1H), 3.23 (q, 2H), 2.84 (s, 3H), 2.24 (s, 3H), 1.66 (m, 2H), 1.16 (t, 3H), 1.02 (t, 3H). LCMS (M+H$^+$)=410.2. HPLC (Condition A): 2.82 min.

EXAMPLES 143–148

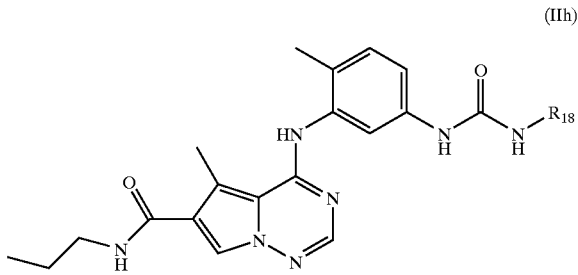

(IIh)

Compound having the formula (IIh), wherein $R_{18}$ has the values listed in Table 14 were prepared following the procedure outlined for Example 142, using different isocyanates in the last step.

EXAMPLES 149–152

The compounds named below were prepared using methods analogous to the procedures described hereinbefore:

149) 1,3-Dihydro-3-[5-methoxy-6-[[4-(4-methyl-1-piperazinyl)butyl]amino]pyrrolo[2,1-f][1,2,4]triazin-4-yl]-2H-indol-2-one;

150) 1,3-Dihydro-3-[5-methoxy-6-[[4-(4-morpholinyl)butyl]amino]pyrrolo[2,1-f][1,2,4]triazin-4-yl]-2H-indol-2-one;

151) 1-[3-[4-(2,3-Dihydro-2-oxo-1H-indol-3-yl)-5-methylpyrrolo[2,1-f][1,2,4]triazin-6-yl]-1-oxopropyl]-4-methylpiperazine; and 152) 2-Methyl-5-[[5-methyl-6-[3-(2H-1,2,3-triazol-2-yl)propoxy]pyrrolo[2,1-f][1,2,4]triazin-4-yl]amino]phenol.

TABLE 14

| Ex. | $R_{18}$ | Compound Name | Data MS/HPLC |
|---|---|---|---|
| 143 | phenyl | 5-Methyl-4-[[2-methyl-5-[[(phenylamino)carbonyl]amino]phenyl]amino]-N-propylpyrrolo[2,1-f][1,2,4]triazine-6-carboxamide | 458.2 3.40 min |
| 144 | 3-methylphenyl | 5-Methyl-4-[[2-methyl-5-[[[(3-methylphenyl)amino]carbonyl]amino]phenyl]amino]-N-propylpyrrolo[2,1-f][1,2,4]triazine-6-carboxamide | 472.5 3.60 |
| 145 | 4-cyanophenyl | 4-[[5-[[[(4-Cyanophenyl)amino]carbonyl]amino]-2-methylphenyl]amino]-5-methyl-N-propylpyrrolo[2,1-f][1,2,4]triazine-6-carboxamide | 483.3 3.48 |
| 146 | 2,3-dichlorophenyl | 4-[[5-[[[(2,3-Dichlorophenyl)amino]carbonyl]amino]-2-methylphenyl]amino]-5-methyl-N-propylpyrrolo[2,1-f][1,2,4]triazine-6-carboxamide | 526.2 3.98 |
| 147 | 4-fluorophenyl | 4-[[5-[[[(4-Fluorophenyl)amino]carbonyl]amino]-2-methylphenyl]amino]-5-methyl-N-propylpyrrolo[2,1-f][1,2,4]triazine-6-carboxamide | 476.2 3.48 |
| 148 | 3-(trifluoromethyl)phenyl | 5-Methyl-4-[[2-methyl-5-[[[[3-(trifluoromethyl)phenyl]amino]carbonyl]amino]phenyl]amino]-N-propylpyrrolo[2,1-f][1,2,4]triazine-6-carboxamide | 526.1 3.87 min |

We claim:
1. A compound having the formula (II):

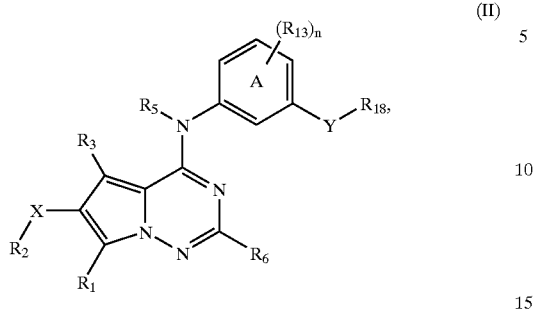

or a pharmaceutically acceptable salt, prodrug or solvate thereof, wherein:

$R_3$ is methyl, $CF_3$, or $CH_3$; $R_5$ is hydrogen or alkyl;

Y is $-C(=O)NR_{23}-$, $-NR_{23}C(=O)NR_{23}-$, $-SO_2NR_{23}$, or $-NR_{23}SO_2-$;

$R_{18}$ and $R_{23}$ are selected from hydrogen, alkyl, alkoxy, aryl, and aryl substituted with one to three $R_{19}$, except when Y is $-NR_{23}SO_2-$, $R_{18}$ is $C_{1-4}$alkyl or aryl optionally substituted with one to three $R_{19}$;

X is selected from $-O-$, $-OC(=O)-$, $-S-$, $-S(=O)-$, $-SO_2-$, $-C(=O)-$, $-CO_2-$, $-NR_{10}-$, $-NR_{10}C(=O)-$, $-NR_{10}C(=O)NR_{11}-$, $-NR_{10}CO_2-$, $-NR_{10}SO_2-$, $-NR_{10}SO_2NR_{11}-$, $-SO_2NR_{10}-$, and $-C(=O)NR_{10}-$, or X is absent;

$R_1$ is hydrogen, $-CH_3$, $-OH$, $-OCH_3$, $-SH$, $-SCH_3$, $-OC(=O)R_{21}$, $-S(=O)R_{22}$, $-SO_2R_{22}$, $-SO_2NR_{24}R_{25}$, $-CO_2R_{21}$, $-C(=O)NR_{24}R_{25}$, $-NH_2$, $-NR_{24}R_{25}$, $-NR_{21}SO_2NR_{24}R_{25}$, $-NR_{21}SO_2R_{22}$, $-NR_{24}C(=O)R_{25}$, $-NR_{24}CO_2R_{25}$, $-NR_{21}C(=O)NR_{24}R_{25}$, halogen, nitro, or cyano;

$R_2$ is selected from
  a) hydrogen, provided that $R_2$ is not hydrogen when X is $-S(=O)-$, $-SO_2-$, $-NR_{10}CO_2-$, or $-NR_{10}SO_2-$;
  b) alkyl, alkenyl, and alkynyl optionally substituted with up to four $R_{26}$, or pentafluoroalkyl;
  c) aryl and heteroaryl optionally substituted with up to three $R_{27}$; and
  d) heterocyclo and cycloalkyl optionally substituted with keto (=O), up to three $R_{27}$, and/or having a carbon-carbon bridge of 3 to 4 carbon atoms;

$R_6$ is hydrogen, alkyl, substituted alkyl, aryl, substituted aryl, heterocyclo, substituted heterocyclo, $-NR_7R_8$, $-OR_7$, or halogen;

$R_{10}$ is hydrogen or alkyl;

$R_{13}$ and $R_{19}$ at each occurrence are independently selected from alkyl, halo, trifluoromethoxy, trifluoromethyl, hydroxy, alkoxy, alkanoyl, alkanoyloxy, thiol, alkylthio, ureido, nitro, cyano, carboxy, carboxyalkyl, carbamyl, alkoxycarbonyl, alkylthiono, arylthiono, arylsulfonylamine, $C_{1-4}$alkylsulfonylamine, sulfonic acid, alkysulfonyl, sulfonamido, and aryloxy, wherein each $R_{13}$ and/or $R_{19}$ group may be further substituted by hydroxy, alkyl, substituted alkyl, alkoxy, aryl, or aralkyl;

$R_7$, $R_8$, $R_{21}$, $R_{24}$, and $R_{25}$ are independently selected from hydrogen, alkyl, substituted alkyl, aryl, substituted aryl, heterocyclo, and substituted heterocyclo;

$R_{22}$ is alkyl, substituted alkyl, aryl, substituted aryl, heterocyclo, or substituted heterocyclo;

$R_{26}$ is selected from halogen, trifluoromethyl, haloalkoxy, keto (=O), nitro, cyano, $-SR_{28}$, $-OR_{28}$, $-NR_{28}R_{29}$, $-NR_{28}SO_2$, $-NR_{28}SO_2R_{29}$, $-SO_2R_{28}$, $-SO_2NR_{28}R_{29}$, $-CO_2R_{28}$, $-C(=O)R_{28}$, $-C(=O)NR_{28}R_{29}$, $-OC(=O)R_{28}$, $-OC(=O)NR_{28}R_{29}$, $-NR_{28}C(=O)R_{29}$, $-NR_{28}CO_2R_{29}$, $=N-OH$, $=N-O$-alkyl; aryl optionally substituted with one to three $R_{27}$; cycloalkyl optionally substituted with keto (=O), one to three $R_{27}$, or having a carbon-carbon bridge of 3 to 4 carbon atoms; and heterocyclo optionally substituted with oxo (=O), one to three $R_{27}$, or having a carbon-carbon bridge of 3 to 4 carbon atoms; wherein $R_{28}$ and $R_{29}$ are each independently selected from hydrogen, alkyl, alkenyl, aryl, aralkyl, $C_{3-7}$cycloalkyl, and $C_{3-7}$heterocycle, or may be taken together to form a $C_{3-7}$heterocycle; and wherein each $R_{28}$ and $R_{29}$ in turn is optionally substituted with up to two of alkyl, alkenyl, halogen, haloalkyl, haloalkoxy, cyano, nitro, amino, hydroxy, alkoxy, alkylthio, phenyl, benzyl, phenyloxy, and benzyloxy;

$R_{27}$ is selected from alkyl, $R_{32}$, and $C_{1-4}$alkyl substituted with one to three $R_{32}$, wherein each $R_{32}$ group is independently selected from halogen, haloalkyl, haloalkoxy, nitro, cyano, $-SR_{30}$, $-OR_{30}$, $-NR_{30}R_{31}$, $-NR_{30}SO_2$, $-NR_{30}SO_2R_{31}$, $-SO_2R_{30}$, $-SO_2NR_{30}R_{31}$, $-CO_2R_{30}$, $-C(=O)R_{30}$, $-C(=O)NR_{30}R_{31}$, $-OC(=O)R_{30}$, $-OC(=O)NR_{30}R_{31}$, $-NR_{30}C(=O)R_{31}$, $-NR_{30}CO_2R_{31}$, and a 3 to 7 membered carbocyclic or heterocyclic ring optionally substituted with alkyl, halogen, hydroxy, alkoxy, haloalkyl, haloalkoxy, nitro, amino, or cyano, wherein $R_{30}$ and $R_{31}$ are each independently selected from hydrogen, alkyl, alkenyl, aryl, aralkyl, $C_{3-7}$cycloalkyl, and heterocycle, or may be taken together to form a $C_{3-7}$heterocycle; and n is 0, 1 or 2.

2. A compound according to claim 1, having the formula (IIa) or (IIb),

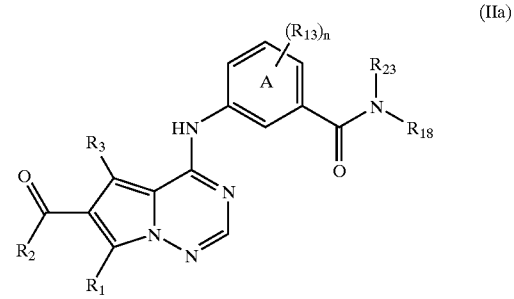

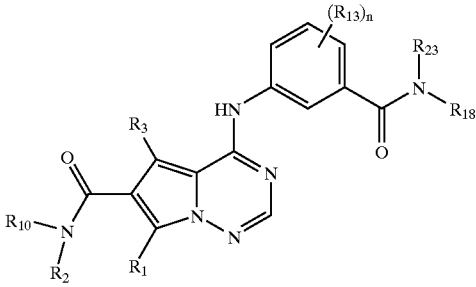

or a pharmaceutically acceptable salt, prodrug, or solvate thereof, wherein:

$R_1$ and $R_{10}$ are hydrogen or $-CH_3$;

$R_{13}$ is lower alkyl, halogen, trifluoromethoxy, trifluoromethyl, hydroxy, $C_{1-4}$alkoxy, nitro, or cyano;

$R_{18}$ is hydroxy, $C_{1-4}$alkoxy, phenyl, or phenyl substituted with one or two $R_{19}$;

$R_{23}$ is hydrogen or lower alkyl; and n is 0, 1 or 2.

3. A compound according to claim 1, or a pharmaceutically acceptable salt, prodrug or solvate thereof, wherein X is —C(=O)—, —CO$_2$—, —NR$_{10}$C(=O)—, or —C(=O)NR$_{10}$—;

Y is —C(=O)NH—, —NHC(=O)NH—, or —NHSO$_2$—;

$R_5$ and $R_{10}$ are hydrogen or —CH$_3$;

$R_{13}$ and $R_{19}$ at each occurrence are independently selected from lower alkyl, halo, trifluoromethoxy, trifluoromethyl, hydroxy, $C_{1-4}$alkoxy, nitro, and cyano;

$R_7$, $R_8$, $R_{21}$, $R_{24}$, and $R_{25}$ are independently selected from hydrogen and lower alkyl;

$R_{22}$ is lower alkyl; and n is 0 or 1.

4. A compound according to claim 1 or a pharmaceutically acceptable salt, prodrug or solvate thereof, in which X—R$_2$ are:

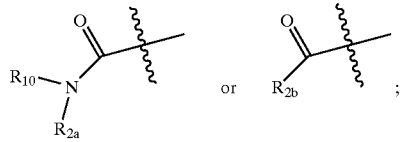

$R_{2a}$ is selected from:
a) hydrogen;
b) straight or branched $C_{2-6}$alkyl;
c) cycloalkyl optionally substituted with oxo and/or up to two $R_{27}$;
d) phenyl optionally substituted with up to two $R_{27}$; and
e) heterocycle optionally substituted with keto and/or up to two $R_{27}$;
f) pentafluoroalkyl or $C_{1-4}$alkyl substituted with up to three of halogen, trifluoromethyl, cyano, OR$_{28}$, NR$_{28}$R$_{29}$, CO$_2$R$_{28}$, aryl, heterocycle, and/or cycloalkyl, wherein the aryl, heterocycle, and/or cycloalkyl in turn are optionally optionally substituted with up to two of halogen, hydroxy, alkoxy, haloalkyl, haloalkoxy, nitro, cyano and alkyl; and $R_{2b}$ is a monocyclic or bicyclic heterocycle optionally substituted with up to two $R_{27}$;

$R_{27}$ at each occurrence is independently selected from hydrogen, alkyl, trifluoromethyl, trifluoromethoxy, halogen, cyano, nitro, amino, hydroxy, alkoxy, phenyl, benzyl, phenyloxy, and benzyloxy; and $R_{28}$ and $R_{29}$ at each occurrence are independently selected from hydrogen, alkyl, alkenyl, phenyl, and benzyl.

5. A compound according to claim 1 or a pharmaceutically acceptable salt, prodrug or solvate thereof, in which:

$R_{2a}$ is selected from:
a) straight or branched $C_{2-6}$ alkyl;
b) phenyl optionally substituted with up to two of halogen, $C_{1-4}$alkoxy, and trifluoromethyl;
c) $C_{3-6}$cycloalkyl optionally substituted with up to two $C_{1-4}$alkyl and/or hydroxy;
d) straight or branched $C_{1-4}$alkyl substituted with up to three of
 i) halogen,
 ii) trifluoromethyl,
 III) cyano,
 iv) $C_{1-4}$alkoxy,
 v) phenyloxy,
 vi) benzyloxy,
 vii) NH$_2$, NH(C$_{1-4}$alkyl), and/or N(C$_{1-4}$alkyl)$_2$,
 viii) phenyl in turn optionally substituted with up to two of halogen and/or methoxy,
 ix) heterocycle selected from pyridinyl, indolyl, thiophenyl, furanyl, thiazolyl, thienyl, morpholinyl, tetrahydrofuranyl, triazinyl, piperazinyl, indenyl, and piperidinyl; said heterocycle optionally substituted with one to two $C_{1-4}$alkyl,
 x) $C_{3-6}$cycloalkyl; and $R_{2b}$ is a five to seven membered monocyclic heterocycle selected from diazepinyl, morpholinyl, piperidinyl, and pyrrolidinyl, said heterocycle optionally substituted with $C_{1-4}$alkyl, phenyl, and/or benzyl.

6. A compound according to claim 1 or a pharmaceutically acceptable salt, prodrug or solvate thereof, in which $R_1$ and $R_{10}$ are independently hydrogen or CH$_3$.

7. A compound according to claim 1 or a pharmaceutically acceptable salt, prodrug or solvate thereof, in which $R_6$ is hydrogen.

8. A compound according to claim 1 or a pharmaceutically acceptable salt, prodrug or solvate thereof, in which Y is —NHC(=O)NH— or —NHSO$_2$—; $R_{18}$ is aryl or aryl substituted with alkyl, OCH$_3$, CF$_3$, cyano, or halogen.

9. A compound according to claim 1 or a pharmaceutically acceptable salt, prodrug or solvate thereof, in which Y is —C(=O)NR$_{23}$—, $R_{23}$ is hydrogen or lower alkyl, and $R_{18}$ is $C_{1-4}$alkoxy or aryl optionally substituted with alkyl, OCH$_3$, CF$_3$, cyano or halogen.

10. A compound according to claim 1, having the formula:

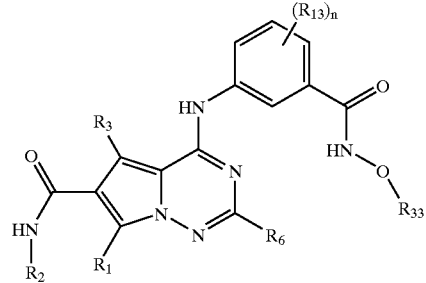

in which $R_{33}$ is lower alkyl.

11. A compound according to 10 or a pharmaceutically acceptable salt, prodrug or solvate thereof, in which $R_3$ and $R_{33}$ are methyl, $R_1$ and $R_6$ are hydrogen, and $R_2$ is a straight or branched $C_{2-6}$alkyl or optionally-substituted benzyl.

12. A compound according to claim 1, which is selected from (i) N-(2,2-Dimethylpropyl)-4-[[5-[(methoxyamino)carbonyl]-2-methylphenyl]amino]N,5-dimethylpyrrolo[2,1-f][1,2,4]triazine-6-carboxamide;

3-[[6-[(Hexahydro-4-methyl-1H-1,4-diazepin-1-yl)carbonyl]-5-methylpyrrolo[2,1-f][1,2,4]triazin-4-yl]amino]-N-methoxy-4-methylbenzamide;

4-[[5-[(Methoxyamino)carbonyl]-2-methylphenyl]amino]-5-methyl-N-(1-methylethyl)pyrrolo[2,1-f][1,2,4]triazine-6-carboxamide;

4-[[5-[(Methoxyamino)carbonyl]-2-methylphenyl]amino]-5-methyl-N-(2-methylpropyl)pyrrolo[2,1-f][1,2,4]triazine-6-carboxamide;

N-(2,2-Dimethylpropyl)-4-[[5-[(methoxyamino)carbonyl]-2-methylphenyl]amino]-5-methylpyrrolo[2,1-f][1,2,4]triazine-6-carboxamide;

4-[[5-[(Methoxyamino)carbonyl]-2-methylphenyl]
amino]-5-methyl-N-propylpyrrolo[2,1-f[]1,2,4]
triazine-6-carboxamide;

N-(1,1-Dimethylethyl)-4-[[5-[(methoxyamino)carbonyl]-
2-methylphenyl]amino]-5-methylpyrrolo[2,1-f][1,2,4]
triazine-6-carboxamide;

4-[[5-[(Methoxyamino)carbonyl]-2-methylphenyl]
amino]-N-(2-methoxyethyl)-5-methylpyrrolo[2,1-f][1,
2,4]triazine-6-carboxamide;

N-Methoxy-4-methyl-3-[[5-methyl-6-(4-
morpholinylcarbonyl)pyrrolo[2,1-f][1,2,4]triazin-4-yl]
amino]benzamide;

N-Cyclohexyl-4-[[5-[(methoxyamino)carbonyl]-2-
methylphenyl]amino]-5-methylpyrrolo[2,1-f][1,2,4]
triazine-6-carboxamide;

4-[[5-[(Methoxyamino)carbonyl]-2-methylphenyl]
amino]-5-methyl-N-[(1R)-1-phenylethyl]pyrrolo[2,1-
f][1,2,4]triazine-6-carboxamide;

4-[[5-[(Methoxyamino)carbonyl]-2-methylphenyl]
amino]-5-methyl-N-[(1S)-1-phenylethyl]pyrrolo[2,1-f]
[1,2,4]triazine-6-carboxamide;

N-[(4-Fluorophenyl)methyl]-4-[[5-[(methoxyamino)
carbonyl]-2-methylphenyl]amino]-5-methylpyrrolo[2,
1-f][1,2,4]triazine-6-carboxamide;

4-[[5-[(Methoxyamino)carbonyl]-2-methylphenyl]
amino]-N-[(2-methoxyphenyl)methyl]-5-
methylpyrrolo[2,1-f][1,2,4]triazine-6-carboxamide;

4-[[5-[(Methoxyamino)carbonyl]-2-methylphenyl]
amino]-5-methyl-N-(4-pyridinylmethyl)pyrrolo]2,1-f]
[1,2,4]triazine-6-carboxamide;

4-[[5-[(Methoxyamino)carbonyl]-2-methylphenyl]
amino]5-methyl-N-[2-(4-pyridinyl)ethyl]pyrrolo[2,1-f
[]1,2,4]triazine-6-carboxamide;

4-[[5-[(Methoxyamino)carbonyl]-2-methylphenyl]
amino]-5-methyl-N-[2-(1-piperidinyl)ethyl]pyrrolo[2,
1-f][1,2,4]triazine-6-carboxamide;

4-[[5-[(Methoxyamino)carbonyl]-2-methylphenyl]
amino]-5-methyl-N-[2-(4-morpholinyl)ethyl]pyrrolo
[2,1-f][1,2,4]triazine-6-carboxamide;

N-[(1R,2S)-2,3-Dihydro-1H-inden-1-yl]-4-[[5-
[(methoxyamino)carbonyl]-2-methylphenyl]amino]5-
methylpyrrolo[2,1-f][1,2,4]triazine-6-carboxamide;

N-[(1S,2R)-2,3-Dihydro-1H-inden-1-yl]-4-[[5-
[(methoxyamino)carbonyl]-2-methylphenyl]amino]-5-
methylpyrrolo[2,1-f][1,2,4]triazine-6-carboxamide;

N-Methoxy-4-methyl-3-[[5-methyl-6-[[4-(phenylmethyl)
1-piperidinyl]carbonyl]pyrrolo[2,1-f][1,2,4]triazin-4-
yl]amino]benzamide;

N-Cyclopropyl-4-[[5-[(methoxyamino)carbonyl]-2-
methylphenyl]amino]-5-methylpyrrolo[2,1-f][1,2,4]
triazine-6-carboxamide;

N-Cyclopentyl-4-[[5-[(methoxyamino)carbonyl]-2-
methylphenyl]amino]-5-methylpyrrolo[2,1-f][1,2,4]
triazine-6-carboxamide;

N-[2-(4-Fluorophenyl)ethyl]-4-[[5-[(methoxyamino)
carbonyl]-2-methylphenyl]amino]-5-methylpyrrolo[2,
1-f][1,2,4]triazine-6-carboxamide;

N-(Cyclohexylmethyl)-4-[[5-[(methoxyamino)carbonyl]
2-methylphenyl]amino]-5-methylpyrrolo[2,1-f][1,2,4]
triazine-6-carboxamide;

4-[[5-[(Methoxyamino)carbonyl]-2-methylphenyl]
amino]-5-methyl-N-[(tetrahydro-2-furanyl)methyl]
pyrrolo[2,1-f][1,2,4]triazine-6-carboxamide;

N-(2-1H-Indol-3-ylethyl)-4-[[5-[(methoxyamino)
carbonyl]-2-methylphenyl]amino]5-methylpyrrolo[2,
1-f][1,2,4]triazine-6-carboxamide;

N-Butyl-4-[[5-[(methoxyamino)carbonyl]-2-
methylphenyl]amino]-5-methylpyrrolo[2,1-f][1,2,4]
triazine-6-carboxamide;

N-(Cyclopropylmethyl)-4-[[5-[(methoxyamino)
carbonyl]-2-methylphenyl]amino]-5-methylpyrrolo[2,
1-f][1,2,4]triazine-6-carboxamide;

4-[[5-[(Methoxyamino)carbonyl]-2-methylphenyl]
amino]-5-methyl-N-(2-methylbutyl)pyrrolo[2,1-f][1,2,
4]triazine-6-carboxamide;

N-(2-Furanylmethyl)-4-[[5-[(methoxyamino)carbonyl]-
2-methylphenyl]amino]-5-methylpyrrolo[2,1-f][1,2,4]
triazine-6-carboxamide;

4-[[5-[(Methoxyamino)carbonyl]-2-methylphenyl]
amino]-5-methyl-N-(2-thienylmethyl)pyrrolo[2,1-f[]1,
2,4]triazine-6-carboxamide;

4-[[5-[(Methoxyamino)carbonyl]-2-methylphenyl]
amino]-5-methyl-N-(2-phenoxyethyl)pyrrolo[2,1-f][1,
2,4]triazine-6-carboxamide;

4-[[5-[(Methoxyamino)carbonyl]-2-methylphenyl]
amino]-5-methyl-N-(2-methylcyclohexyl)pyrrolo[2,1-
f][1,2,4]triazine-6-carboxamide;

N-Ethyl-4-[[5-[(methoxyamino)carbonyl]-2-
methylphenyl]amino]-N,5-dimethylpyrrolo[2,1-f][1,2,
4]triazine-6-carboxamide;

4-[[5-[(Methoxyamino)carbonyl]-2-methylphenyl]
amino]-5-methyl-N-(2,2,2-trifluoroethyl)pyrrolo[2,1-
f][1,2,4]triazine-6-carboxamide;

N-(2-Fluoroethyl)-4-[[5-[(methoxyamino)carbonyl]-2-
methylphenyl]amino]-5-methylpyrrolo[2,1-f][1,2,4]
triazine-6-carboxamide;

N-(2,3-Dihydro-1H-inden-2-yl)-4-[[5-[(methoxyamino)
carbonyl]-2-methylphenyl]amino]-5-methylpyrrolo[2,
1-f][1,2,4]triazine-6-carboxamide;

N-Ethyl-4-[[5-[(methoxyamino)carbonyl]-2-
methylphenyl]amino]-5-methylpyrrolo[2,1-f][1,2,4]
triazine-6-carboxamide;

4-[[5-[(Methoxyamino)carbonyl]-2-methylphenyl]
amino]-5-methyl-N-(2,2,3,3,3-pentafluoropropyl)
pyrrolo[2,1-f][1,2,4]triazine-6-carboxamide;

4-[[5-[(Methoxyamino)carbonyl]-2-methylphenyl]
amino]-5,7-dimethyl-N-(1-methylethyl)pyrrolo[2,1-f]
[1,2,4]triazine-6-carboxamide;

N-(4-Fluorophenyl)-4-[[5-[(methoxyamino)carbonyl]-2-
methylphenyl]amino]-5-methylpyrrolo[-2,1-f][1,2,4]
triazine-6-carboxamide;

4-[[5-[(Methoxyamino)carbonyl]-2-methylphenyl]
amino]-N-(2-methoxyphenyl)-5-methylpyrrolo[2,1-f]
[1,2,4]triazine-6-carboxamide;

4-[[5-[(Methoxyamino)carbonyl]-2-methylphenyl]
amino]-N-[(3-methoxyphenyl)methyl]-5-
methylpyrrolo[2,1-f][1,2,4]triazine-6-carboxamide;

4-[[5-[(Methoxyamino)carbonyl]-2-methylphenyl]
amino]-5-methyl-N-[3-(trifluoromethyl)phenyl]
pyrrolo[2,1-f][1,2,4]triazine-6-carboxamide;

N-[(2,6-Dichlorophenyl)methyl]-4-[[5-[(methoxyamino)
carbonyl]-2-methylphenyl]amino]-5-methylpyrrolo[2,
1-f][1,2,4]triazine-6-carboxamide;

N-[(1S)-1-Cyano-2-phenylethyl]-4-[[5-[(methoxyamino)
carbonyl]-2-methylphenyl]amino]-5-methylpyrrolo[2,
1-f][1,2,4]triazine-6-carboxamide;

4-[[5-[(Methoxyamino)carbonyl]-2-methylphenyl]
amino]-5-methyl-N-(2-phenylethyl)pyrrolo[2,1-f][1,2,
4]triazine-6-carboxamide;

N-Methoxy-4-methyl-3-[[5-methyl-6-(1-
pyrrolidinylcarbonyl)pyrrolo[2,1-f][1,2,4]triazin-4-yl]
amino]benzamide;

4-[[5-[(Methoxyamino)carbonyl]-2-methylphenyl]
amino]-5-methyl-N-(2-pyridinylmethyl)pyrrolo[2,1-f]
[1,2,4]triazine-6-carboxamide;

4-[[5-[(Methoxyamino)carbonyl]-2-methylphenyl]
amino]-5-methyl-N-(phenylmethyl)pyrrolo[2,1-f][1,2,
4]triazine-6-carboxamide;

4-[[5-[(Methoxyamino)carbonyl]-2-methylphenyl]
amino]-5-methyl-N-(4-methyl-2-thiazolyl)pyrrolo[2,1-
f][1,2,4]triazine-6-carboxamide;

4-[[5-[(Methoxyamino)carbonyl]-2-methylphenyl]
amino]-5-methyl-N-[(1R)-1-methylpropyl]pyrrolo[2,
1-f][1,2,4]triazine-6-carboxamide;

4-[[5-[(Methoxyamino)carbonyl]-2-methylphenyl]
amino]-5-methyl-N-[(1S)-1-methylpropyl]pyrrolo[2,1-
f][1,2,4]triazine-6-carboxamide;

N-[(3-Fluorophenyl)methyl]-4-[[5-[(methoxyamino)
carbonyl]-2-methylphenyl]amino]-5-methylpyrrolo[2,
1-f][1,2,4]triazine-6-carboxamide;

N-[1-(4-Fluorophenyl)ethyl]-4-[[5-[(methoxyamino)
carbonyl]-2-methylphenyl]amino]-5-methylpyrrolo[2,
1-f][1,2,4]triazine-6-carboxamide;

N-[(2,4-Difluorophenyl)methyl]-4-[[5-[(methoxyamino)
carbonyl]-2-methylphenyl]amino]-5-methylpyrrolo[2,
1-f][1,2,4]triazine-6-carboxamide; and N-[(2,6-Difluorophenyl)methyl]-4-[[5-[(methoxyamino)
carbonyl]-2-methylphenyl]amino]-5-methylpyrrolo[2,
1-f][1,2,4]triazine-6-carboxamide;

4-[[5-[[(4-Cyanophenyl)amino]carbonyl]-2-
methylphenyl]amino]-N-ethyl-5-methyl pyrrolo[2,1-f]
[1,2,4]triazine-6-carboxamide; 4-[[5-[[(4-Cyano-
phenyl)amino]carbonyl]-2-methylphenyl]amino]-5-
methyl-N-[(1S)-1-phenylethyl]pyrrolo[2,1-f][1,2,4]
triazine-6-carboxamide; 4-[[5-[[[(4-Cyanophenyl)
amino]carbonyl]amino]-2-methylphenyl]amino]-5-
methyl-N-propylpyrrolo[2,1-f][1,2,4]triazine-6-
carboxamide;

or is (ii) a pharmaceutically-acceptable salt, hydrate, or prodrug thereof.

13. A compound according to claim 1 which is selected from N-Ethyl-4-[[5-[(methoxyamino)carbonyl]-2-methylphenyl]amino]-5-methylpyrrolo[2,1-f][1,2,4] triazine-6-carboxamide; 4-[[5-[(Methoxyamino)carbonyl]-2-methylphenyl]amino]-5-methyl-N-(1-methylethyl) pyrrolo [2,1-f][1,2,4]triazine-6-carboxamide; 4-[[5-[(Methoxyamino)carbonyl]-2-methylphenyl]amino]-5-methyl-N-propylpyrrolo[2,1-f][1,2,4]triazine-6-carboxamide; 4-[[5-[(Methoxyamino)carbonyl]-2-methylphenyl]amino]-5-methyl-N-[1-phenylethyl]pyrrolo [2,1-f][1,2,4]triazine-6-carboxamide; and 4-[[5-[(Methoxyamino)carbonyl]-2-methylphenyl]amino]-5-methyl-N-[1-methylpropyl]pyrrolo[2,1-f][1,2,4]triazine-6-carboxamide; and a pharmaceutically-acceptable salt thereof.

14. A compound having the formula (II):

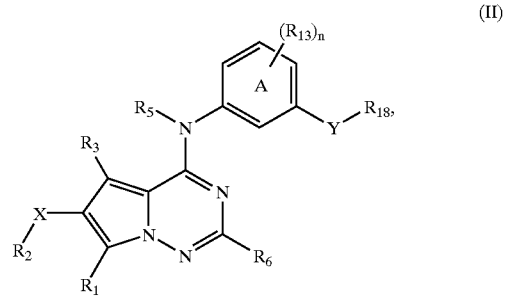

or a pharmaceutically acceptable salt, prodrug or solvate thereof, wherein $R_3$ is methyl or $CF_3$;

$R_5$ is hydrogen or lower alkyl;

Y is $-C(=O)NR_{23}-$, $-NR_{23}C(=O)NR_{23}-$, $-NR_{23}SO_2-$, or $-SO_2NH_2-$;

$R_{18}$ and $R_{23}$ are selected from hydrogen, alkyl, alkoxy, aryl, and aryl substituted with one to three $R_{19}$, except when Y is $-NR_{23}SO_2-$, $R_{18}$ is $C_{1-4}$alkyl or aryl optionally substituted with one to three $R_{19}$;

X is selected from $-O-$, $-OC(=O)-$, $-S-$, $-S(=O)-$, $-SO_2-$, $-C(=O)-$, $-CO_2-$, $-NR_{10}-$, $-NR_{10}C(=O)-$, $-NR_{10}C(=O)NR_{11}-$, $-NR_{10}CO_2-$, $-NR_{10}SO_2-$, $-NR_{10}SO_2NR_{11}-$, $-SO_2NR_{10}-$, and $-C(=O)NR_{10}-$, or X is absent;

$R_1$ is hydrogen, $-CH_3$, $-OH$, $-OCH_3$, $-SH$, $-SCH_3$, $-OC(=O)R_{21}$, $-S(=O)R_{22}$, $-SO_2R_{22}$, $-SO_2NR_{24}R_{25}$, $-CO_2R_{21}$, $-C(=O)NR_{24}R_{25}$, $-NH_2$, $-NR_{21}SO_2NR_{24}R_{25}$, $-NR_{21}SO_2R_{22}$, $-NR_{24}C(=O)R_{25}$, $-NR_{24}CO_2R_{25}$, $-NR_{21}C(=O)NR_{24}R_{25}$, halogen, nitro, or cyano;

$R_2$ is alkyl, substituted alkyl, alkenyl, substituted alkenyl, alkynyl, substituted alkynyl, aryl, substituted aryl, heterocyclo, substituted heterocyclo, aralkyl, substituted aralkyl, heterocycloalkyl, or substituted heterocycloalkyl;

$R_6$ is hydrogen, alkyl, substituted alkyl, aryl, substituted aryl, heterocyclo, substituted heterocyclo, $-NR_7R_8$, $-OR_7$, or halogen;

$R_{13}$ and $R_{19}$ at each occurrence are independently selected from alkyl, halo, trifluoromethoxy, trifluoromethyl, hydroxy, alkoxy, alkanoyl, alkanoyloxy, thiol, alkylthio, ureido, nitro, cyano, carboxy, carboxyalkyl, carbamyl, alkoxycarbonyl, alkylthiono, arylthiono, arylsulfonylamine, $C_{1-4}$alkylsulfonylamine, sulfonic acid, alkysulfonyl, sulfonamido, and aryloxy, wherein each group $R_{13}$ and $R_{19}$ may be further substituted by hydroxy, alkyl, alkoxy, aryl, or aralkyl;

$R_7$, $R_8$, $R_{21}$, $R_{24}$, and $R_{25}$ are independently selected from hydrogen, alkyl, substituted alkyl, aryl, substituted aryl, heterocyclo, and substituted heterocyclo;

$R_{22}$ is alkyl, substituted alkyl, aryl, substituted aryl, heterocyclo, or substituted heterocyclo; and n is 0, 1 or 2.

15. A compound according to claim 14, having the formula:

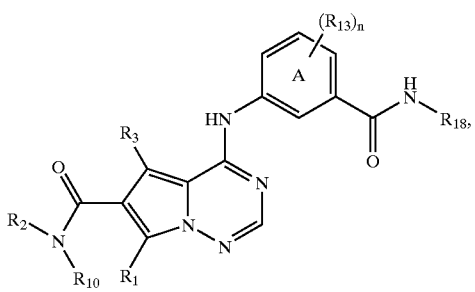

or a pharmaceutically acceptable salt, prodrug or solvate thereof; wherein:
$R_{18}$ is alkoxy, aryl, or aryl substituted with $R_{19}$;
$R_1$ and $R_{10}$ are hydrogen or —$CH_3$; and
$R_{13}$ is lower alkyl, halogen, trifluoromethoxy, trifluoromethyl, hydroxy, $C_{1-4}$alkoxy, nitro, or cyano.

16. A compound according to claim 14 having the formula:

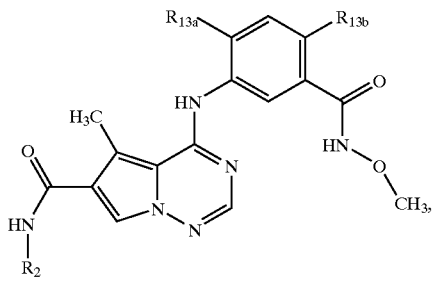

or a pharmaceutically-acceptable salt, hydrate or prodrug thereof, in which $R_2$ is a straight or branched $C_{2-6}$alkyl or optionally-substituted benzyl, and $R_{13a}$ and $R_{13b}$ are selected from hydrogen, $C_{1-4}$alkyl, hydroxy, halogen, cyano, and trifluoromethyl.

17. A compound according to claim 14 which is N-Ethyl-4-[[5-[(methoxyamino)carbonyl]-2-methylphenyl]amino]-5-methylpyrrolo[2,1-f][1,2,4]triazine-6-carboxamide; or a pharmaceutically acceptale salt comprising a methanesulfonic salt thereof.

18. A compound according to claim 14 which is 4-[[5-[(Methoxyamino)carbonyl]-2-methylphenyl]amino]-5-methyl-N-(1-methylethyl)pyrrolo [2,1-f][1,2,4]triazine-6-carboxamide; or a pharmaceutically acceptale salt thereof.

19. A compound according to claim 14 which is 4-[[5-[(Methoxyamino)carbonyl]-2-methylphenyl]amino]-5-methyl-N-propylpyrrolo[2,1-f][1,2,4]triazine-6-carboxamide; or a pharmaceutically acceptale salt thereof.

20. A compound according to claim 14 which is 4-[[5-[(Methoxyamino)carbonyl]-2-methylphenyl]amino]-5-methyl-N-[1-phenylethyl]pyrrolo[2,1-f][1,2,4]triazine-6-carboxamide; or a pharmaceutically acceptale salt thereof.

21. A compound according to claim 14 which is 4-[[5-[(Methoxyamino)carbonyl]-2-methylphenyl]amino]-5-methyl-N-[1-methylpropyl]pyrrolo[2,1-f][1,2,4]triazine-6-carboxamide; or a pharmaceutically-acceptable salt thereof.

22. A pharmaceutical composition comprising at least one compound according to claim 1 and a pharmaceutically-acceptable carrier or diluent.

23. A pharmaceutical composition comprising at least one compound according to claim 14 and a pharmaceutically-acceptable carrier or diluent.

24. A method of treating an inflammatory disorder in which the inflammatory disorder is selected from asthma, adult respiratory distress syndrome, chronic obstructive pulmonary disease, chronic pulmonary inflammatory disease, diabetes, inflammatory bowel disease, osteoporosis, psoriasis, graft vs. host rejection, atherosclerosis, rhematoid arthritis, psoriatic arthritis, traumatic arthritis, rubella arthritis, gouty arthritis and osteoarthritis.

* * * * *

UNITED STATES PATENT AND TRADEMARK OFFICE
CERTIFICATE OF CORRECTION

PATENT NO. : 6,670,357 B2
DATED : December 30, 2003
INVENTOR(S) : Leftheris et al.

It is certified that error appears in the above-identified patent and that said Letters Patent is hereby corrected as shown below:

Column 10,
Line 39, "—$OCF_3$" should read -- —$OCH_3$ --.

Column 87,
Line 19, "$CH_3;R_5$" should read -- $OCH_3; R_5$ --.

Signed and Sealed this

Twenty-first Day of June, 2005

JON W. DUDAS
*Director of the United States Patent and Trademark Office*